United States Patent [19]
Green et al.

[11] Patent Number: 5,862,972
[45] Date of Patent: Jan. 26, 1999

[54] GAS POWERED APPARATUS FOR APPLYING SURGICAL FASTENERS TO BODY TISSUE

[75] Inventors: David T. Green, Westport; Henry Bolanos; Lisa W. Heaton, both of Norwalk; Thomas A. Pelletier, Wallingford, all of Conn.

[73] Assignee: United States Surgical Corporation, Norwalk, Conn.

[21] Appl. No.: 566,251

[22] Filed: Dec. 1, 1995

Related U.S. Application Data

[63] Continuation of Ser. No. 136,653, Oct. 14, 1993, abandoned.

[51] Int. Cl.$^6$ .................................................... A61B 17/068
[52] U.S. Cl. ...................... 227/175.1; 227/19; 227/176.1
[58] Field of Search .................................. 227/19, 175.1, 227/176.1, 178.1, 180.1, 181.1

[56] References Cited

U.S. PATENT DOCUMENTS

| | | |
|---|---|---|
| 28,932 | 8/1860 | Noiles et al. . |
| 3,613,507 | 10/1971 | Smith, Jr. . |
| 3,618,842 | 11/1971 | Bryan . |
| 3,643,851 | 2/1972 | Green et al. . |
| 3,662,939 | 5/1972 | Bryan . |
| 3,717,294 | 2/1973 | Green . |
| 3,815,476 | 6/1974 | Green et al. . |
| 3,837,555 | 9/1974 | Green . |
| 4,331,277 | 5/1982 | Green . |
| 4,349,028 | 9/1982 | Green . |
| 4,407,432 | 10/1983 | Shichman . |
| 4,919,152 | 4/1990 | Ger . |
| 4,944,443 | 7/1990 | Oddsen et al. . |
| 5,018,657 | 5/1991 | Pedlick et al. . |
| 5,040,715 | 8/1991 | Green et al. . |
| 5,071,430 | 12/1991 | de Salis et al. . |
| 5,084,057 | 1/1992 | Green et al. . |
| 5,100,420 | 3/1992 | Green et al. . |
| 5,125,553 | 6/1992 | Oddsen et al. . |
| 5,163,598 | 11/1992 | Peters et al. ............................ 227/19 X |
| 5,174,487 | 12/1992 | Rothfuss et al. . |
| 5,176,692 | 1/1993 | Wilk et al. . |
| 5,220,928 | 6/1993 | Oddsen et al. . |
| 5,246,156 | 9/1993 | Rothfuss et al. . |
| 5,364,001 | 11/1994 | Bryan .................................... 227/19 X |

FOREIGN PATENT DOCUMENTS

| | | |
|---|---|---|
| 0041022 | 12/1981 | European Pat. Off. . |
| 0324637 | 7/1989 | European Pat. Off. . |
| 0541987 | 5/1993 | European Pat. Off. . |
| 0552423 | 7/1993 | European Pat. Off. . |

OTHER PUBLICATIONS

Ralph Ger MD, *Instruments and Techniques, The management of certain abdominal herniae by intra–abdominal closure of the neck of the sac*, pp. 342–344 (1982).
U.S. Surgical Corporation Information Booklet for Auto Suture®, Skin & Fascia, 1978.
U.S. Surgical Corporation Information Booklet for Auto Suture®, Multifire Premium™, 1990.
U.S. Surgical Corporation Information Booklet for Auto Suture®, Premium Surgiclip™ Titanium, 1989.

*Primary Examiner*—Rinaldi I. Rada
*Assistant Examiner*—Boyer Ashley

[57] ABSTRACT

An endoscopic surgical stapling apparatus is disclosed. The apparatus comprises a frame and a generally elongated endoscopic section connected to the frame and extending distally therefrom. The endoscopic section includes a mechanism for storing a plurality of staples, a mechanism for advancing the staples for positioning adjacent body tissue and a mechanism for at least partially closing each staple. A low pressure pneumatic system disposed in the frame provides the forces to at least partially activate the staple advancing mechanism. The apparatus has particular application in attaching mesh to body tissue as in laparoscopic hernia repair.

13 Claims, 37 Drawing Sheets

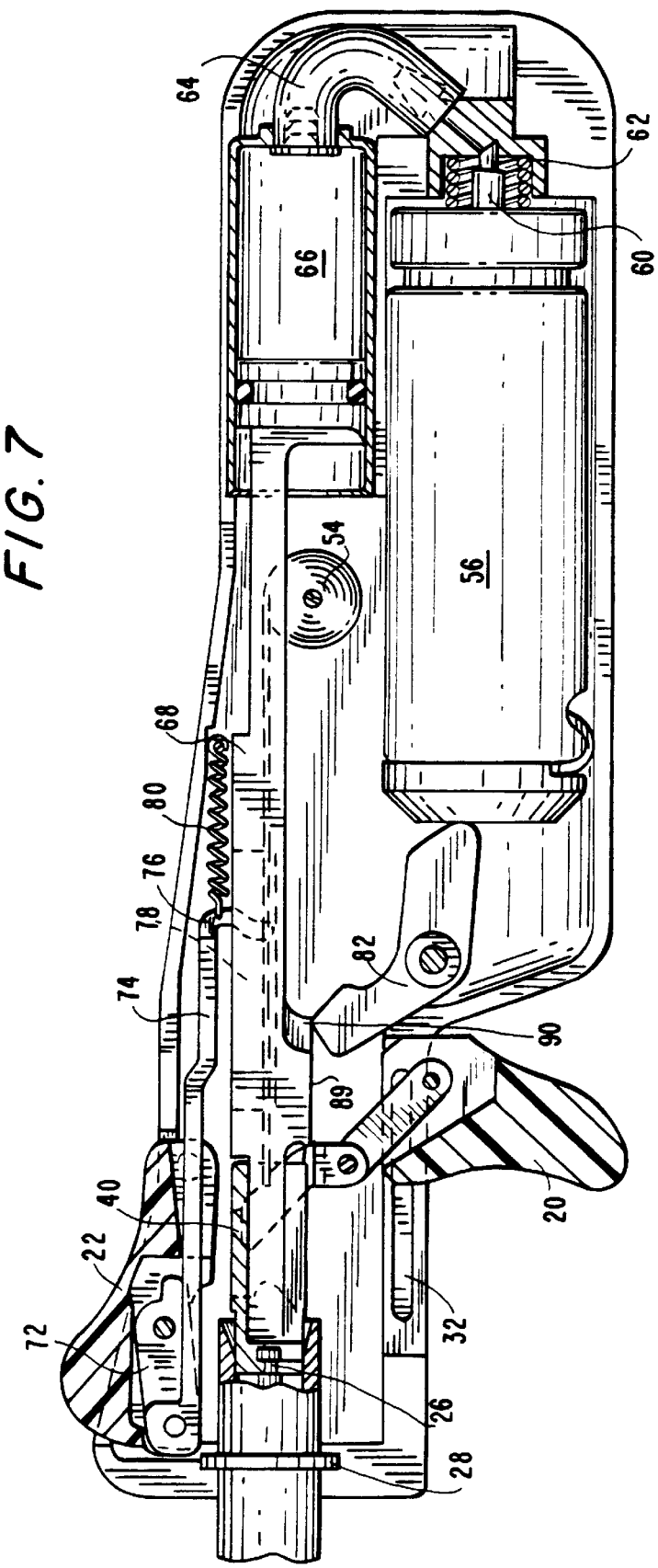

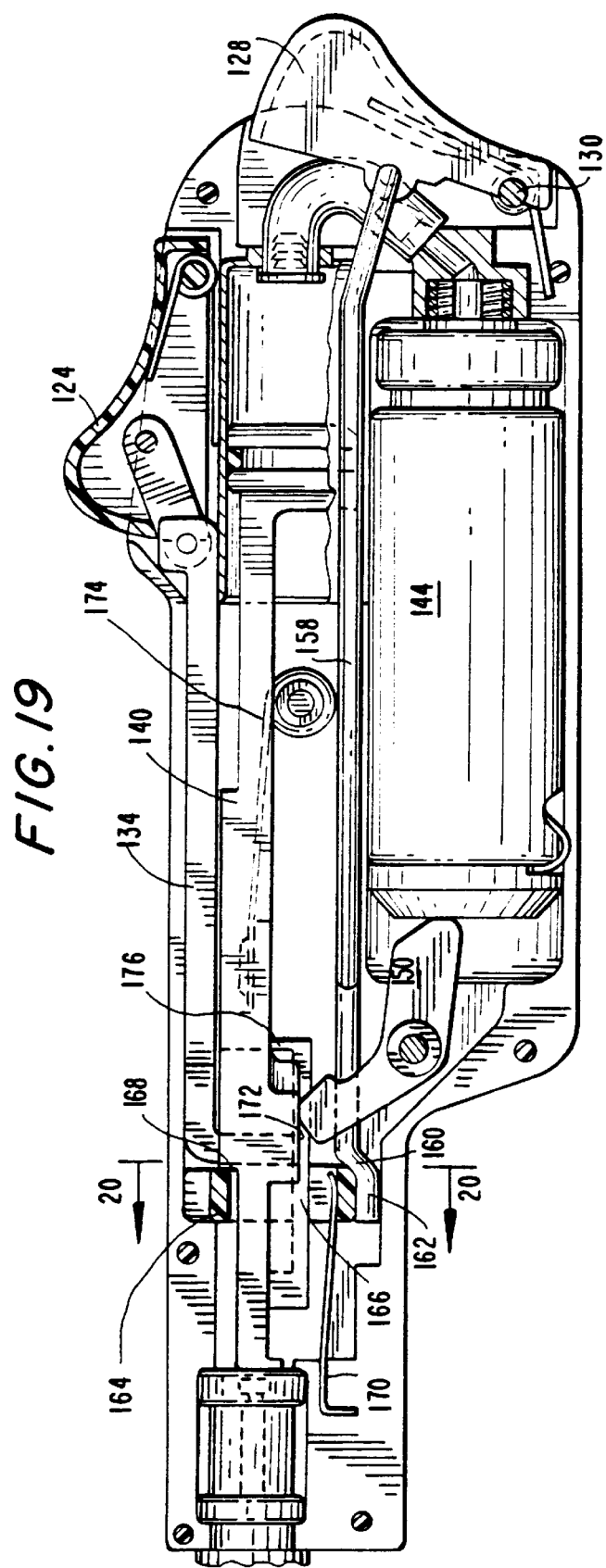

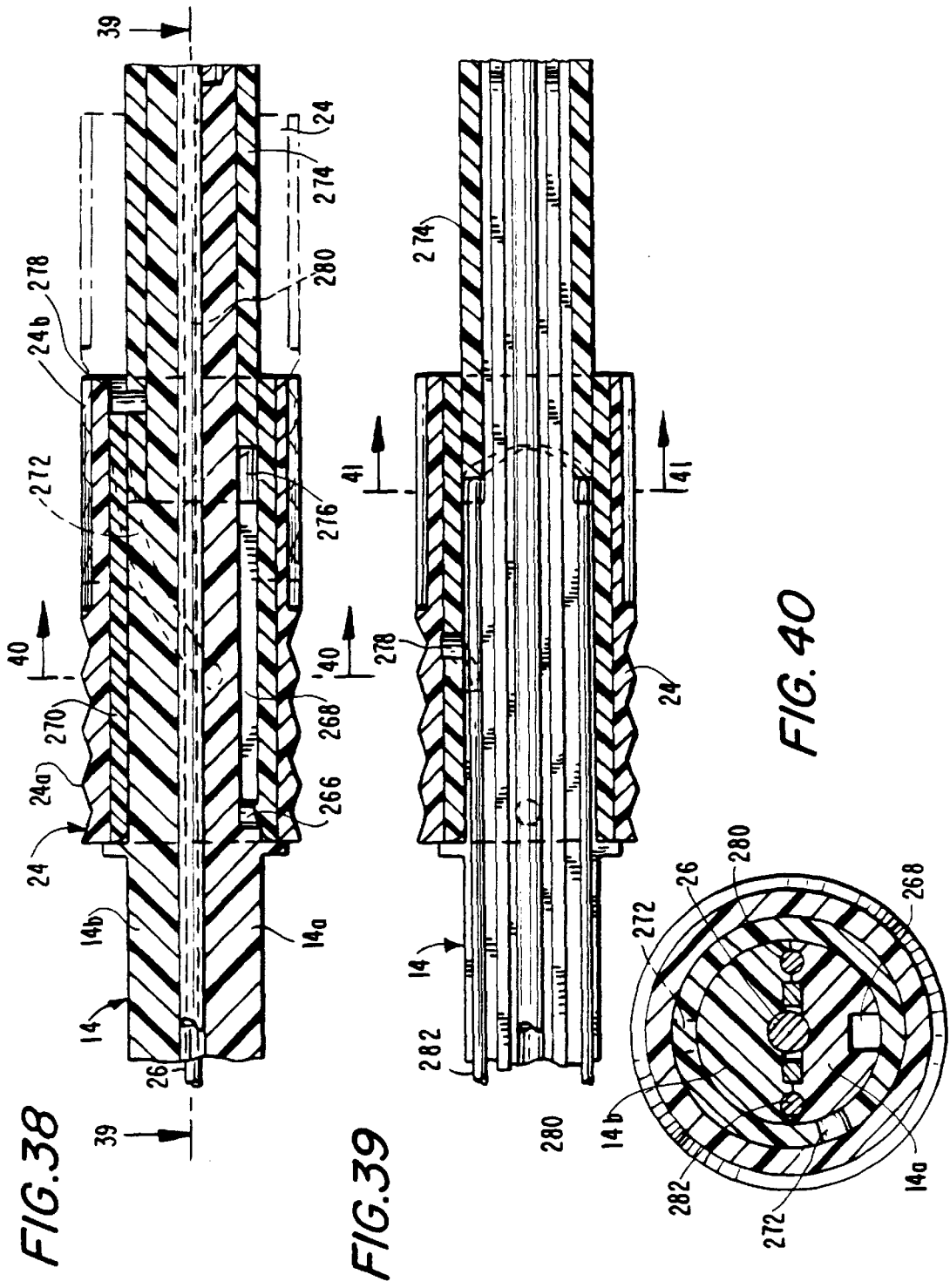

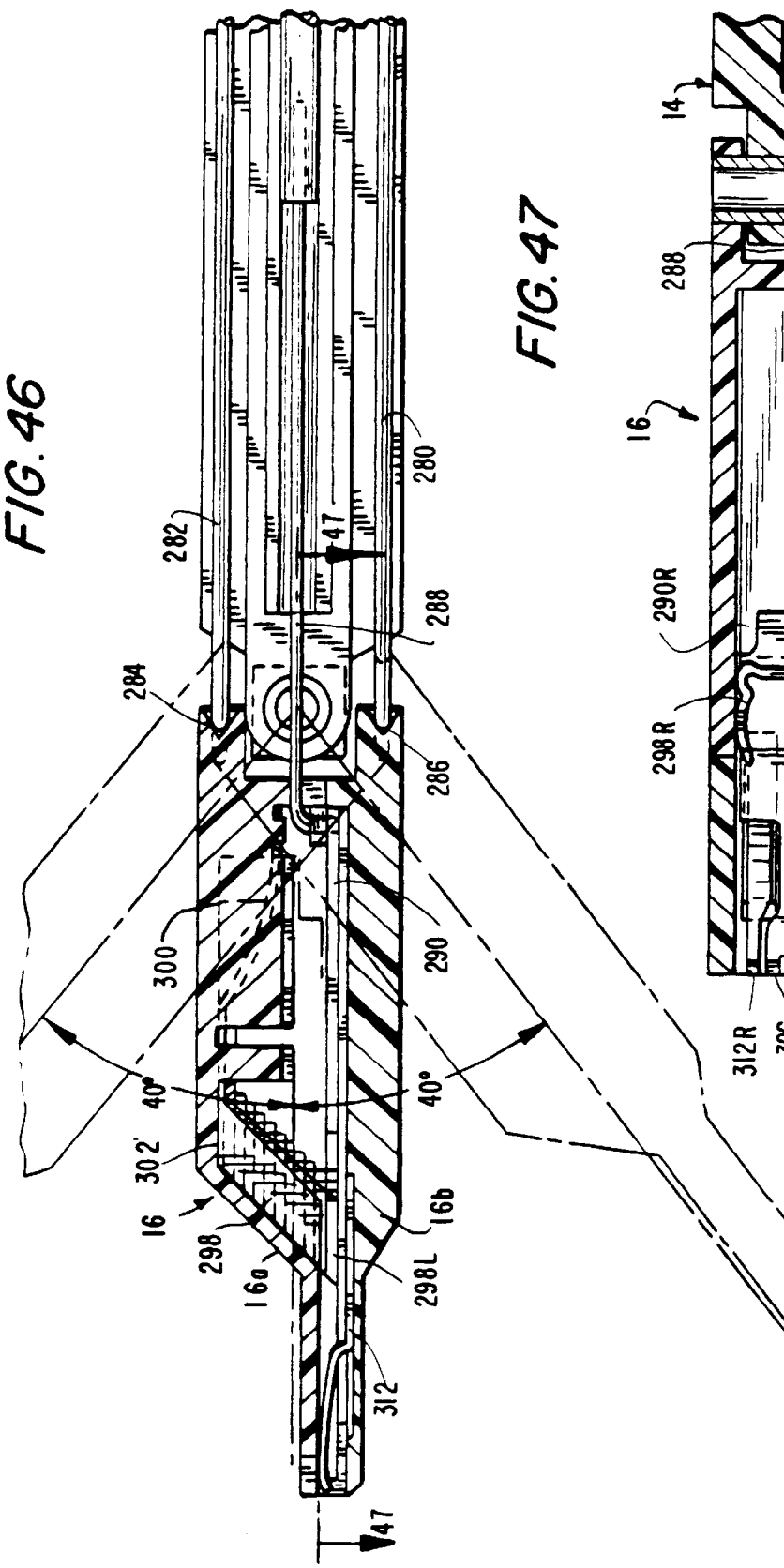

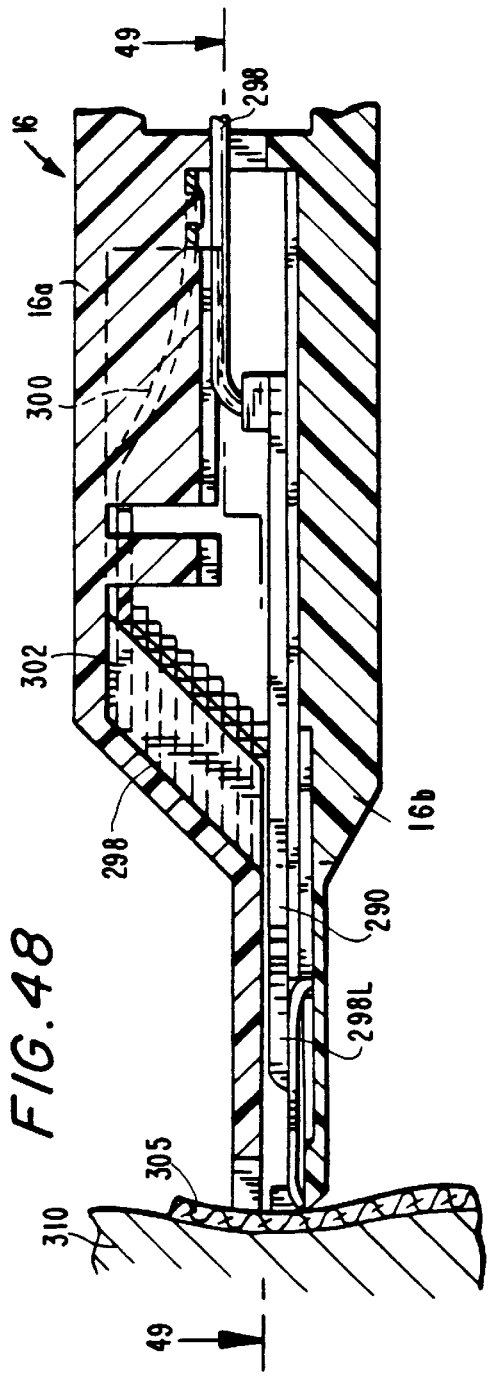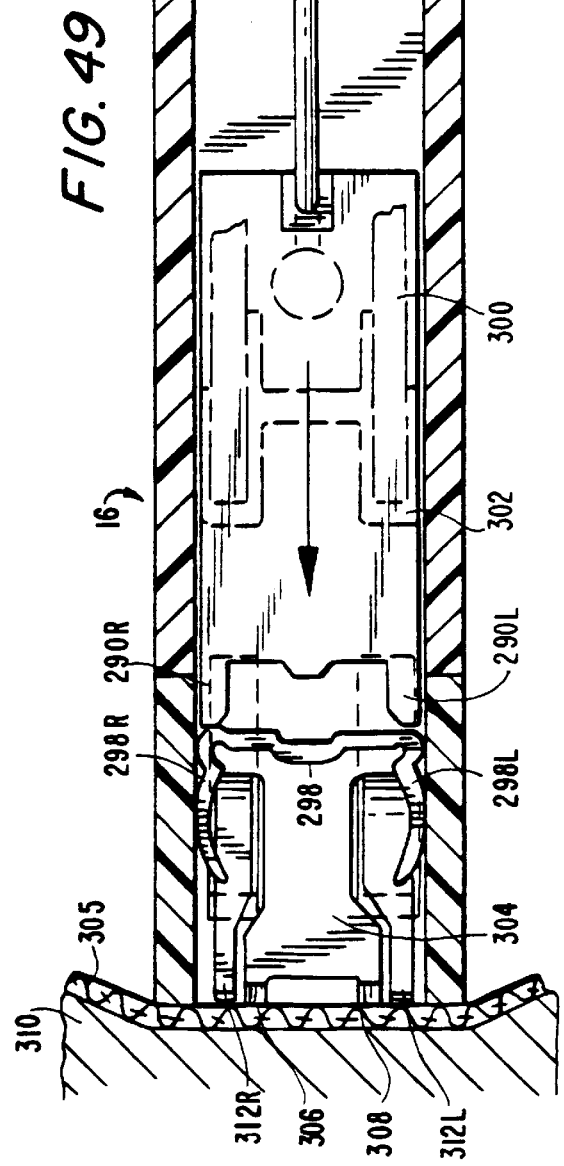

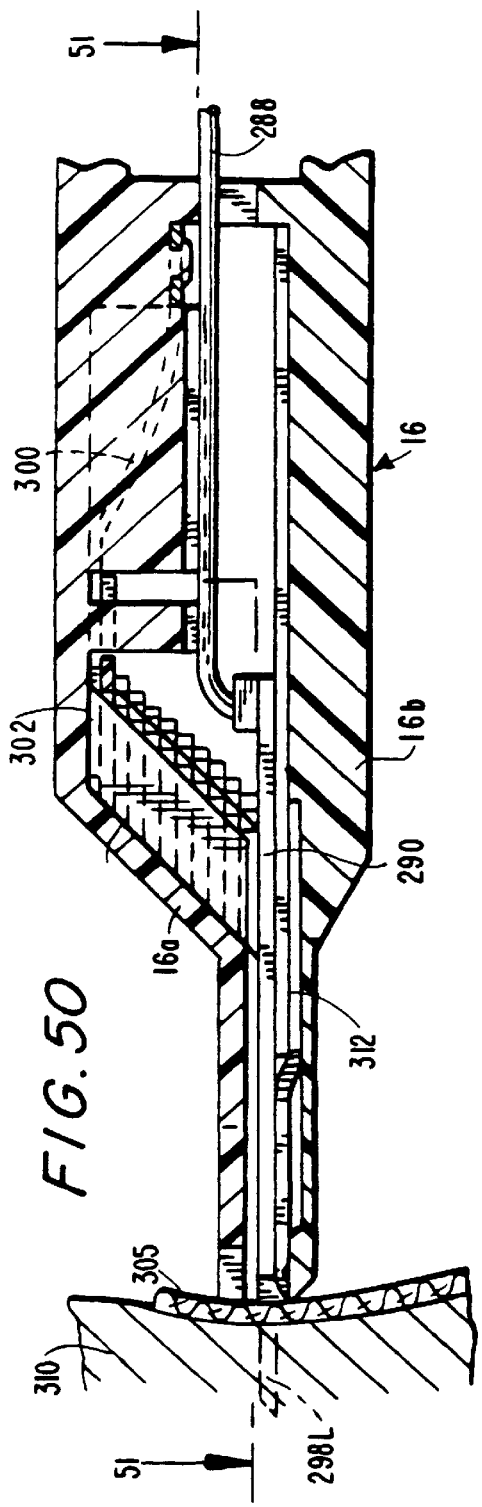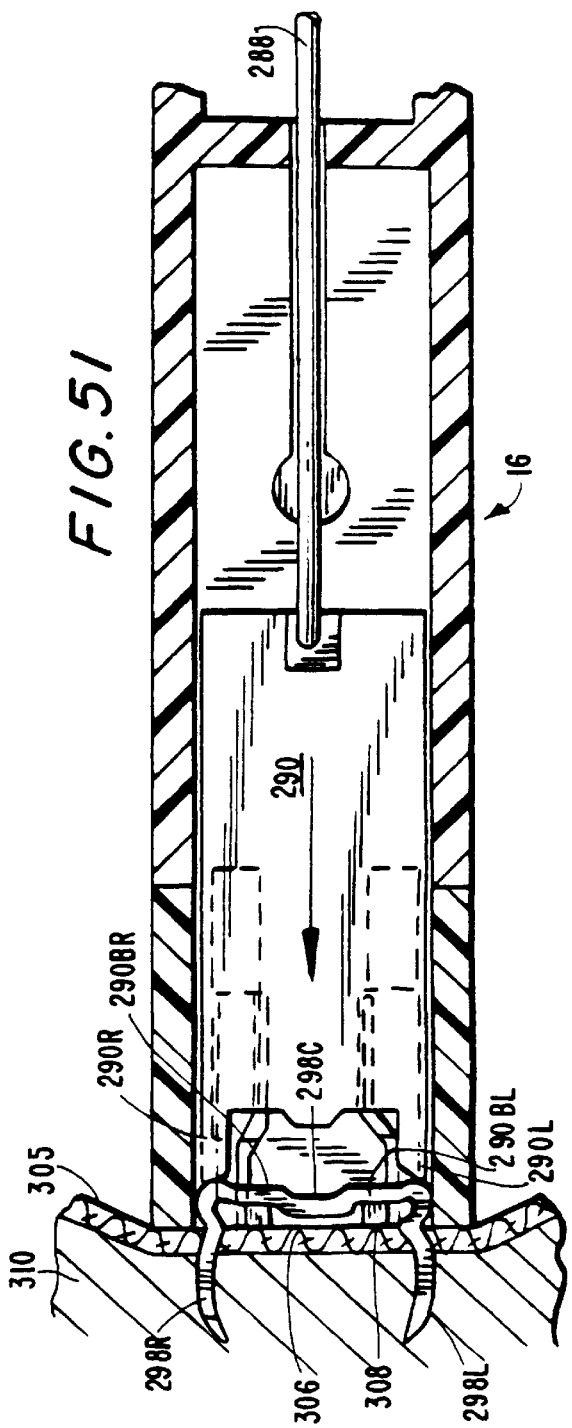

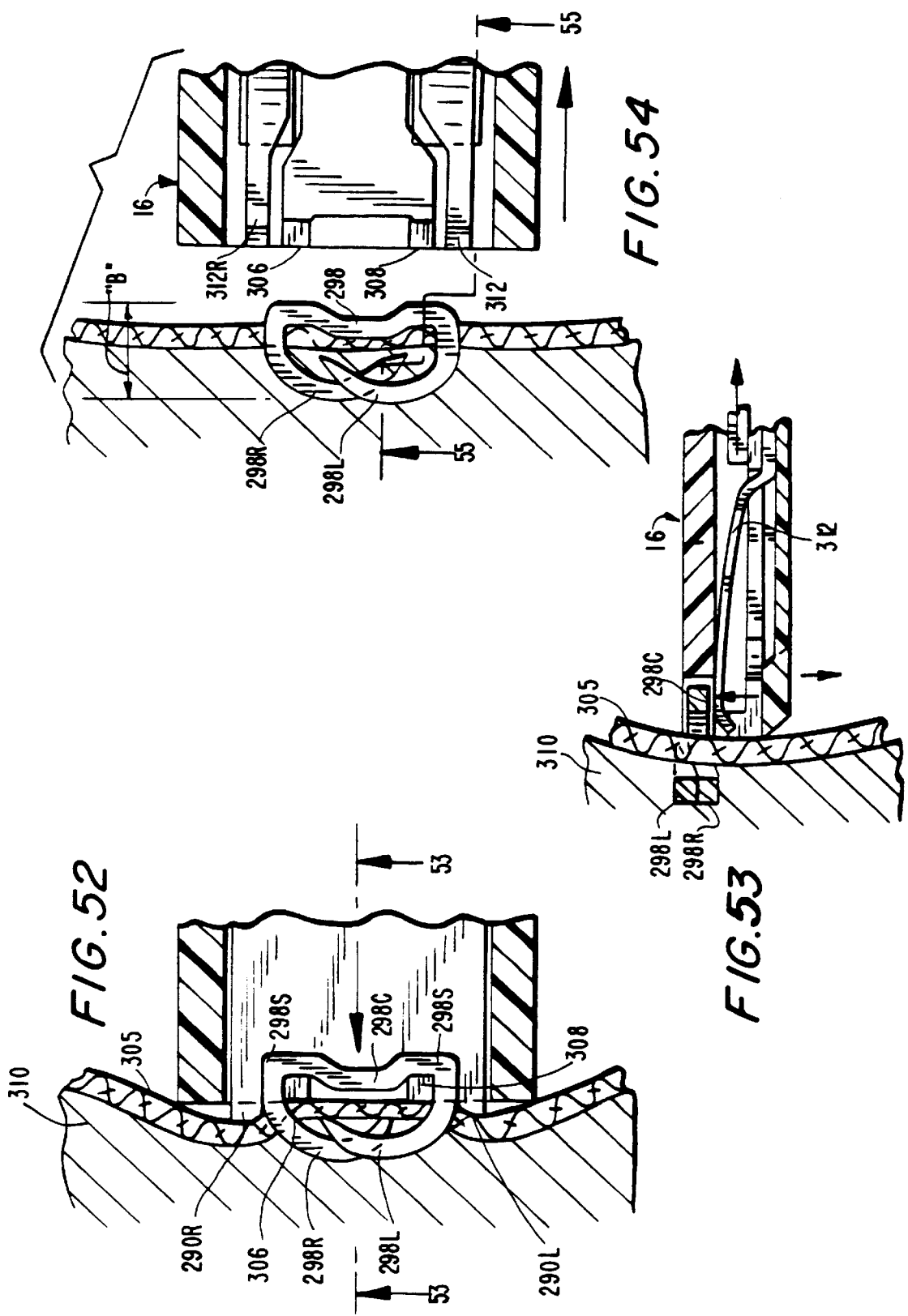

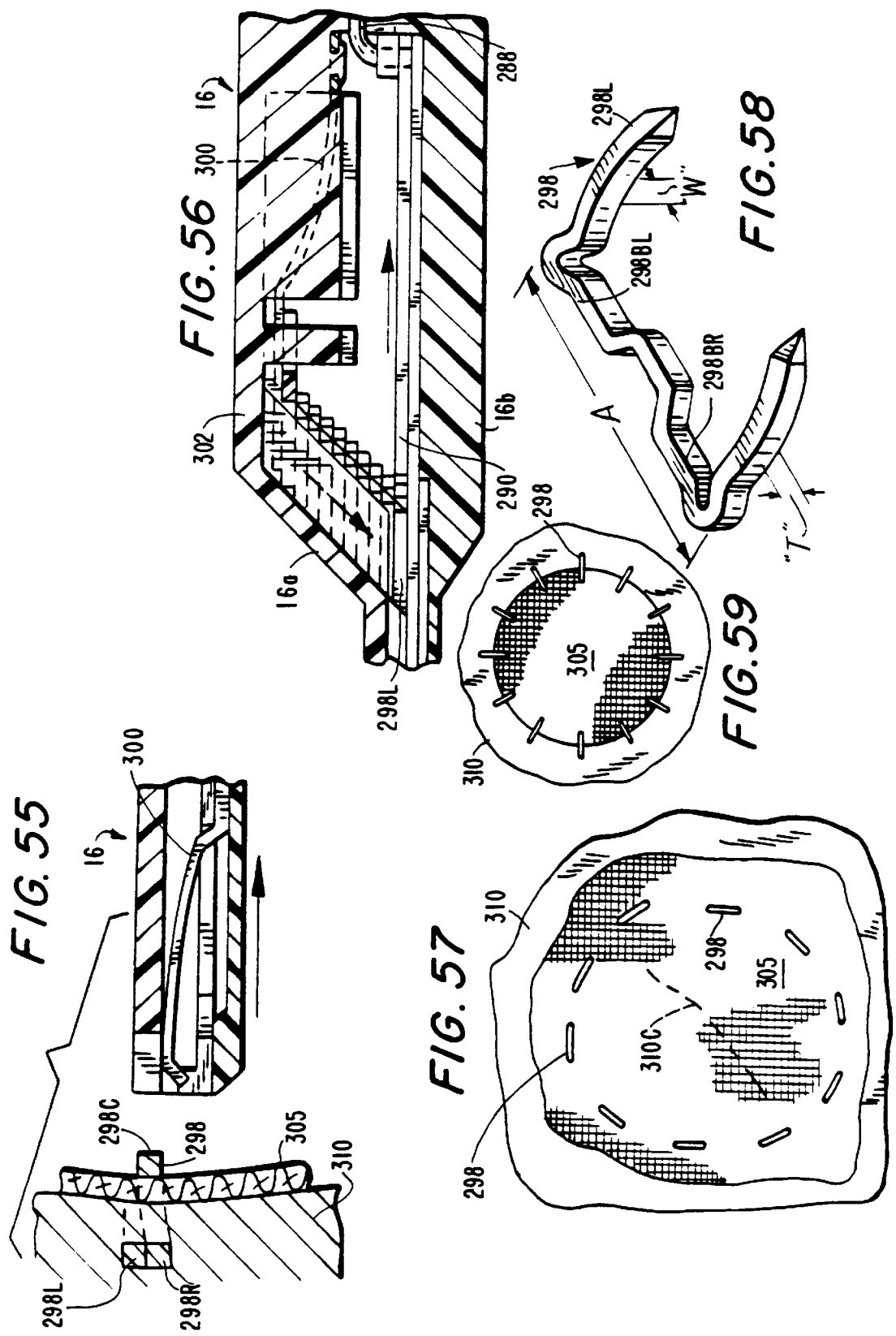

GAS POWERED APPARATUS FOR APPLYING SURGICAL FASTENERS TO BODY TISSUE

This is a continuation of application Ser. No. 08/136,653 filed on Oct. 14, 1993, now abandoned.

BACKGROUND OF THE INVENTION

1. Field of the Invention

The present invention relates to an apparatus and method for applying surgical staples to body tissue. More particularly, this invention relates to a laparoscopic or endoscopic surgical stapling apparatus which is at least partially powered by a low pressure pneumatic system.

2. Background of the Invention

In laparoscopic procedures, surgery is performed in the interior of the abdomen through a small incision. In endoscopic procedures, surgery is performed in any hollow viscus of the body through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues and vessels far removed from the incision, thereby requiring that any instruments being used in such procedures be long and narrow while being functionally controllable from one end of the instrument, i.e. the proximal end.

Examples of surgical instruments having laparoscopic and/or endoscopic application are disclosed in commonly assigned U.S. Pat. No. 5,040,715 to Green et al., U.S. Pat. No. 5,071,430 to de Salis et al., U.S. Pat. No. 5,084,057 to Green et al. and U.S. Pat. No. 5,100,420 to Green et al. The instrument disclosed in the '715 patent to Green et al. is adapted to place one or more rows of staples endoscopically to perform gastrointestinal anastomosis. The instrument disclosed in the '430 patent to de Salis et al. endoscopically drives fasteners into body tissue for ablation of organs. The instruments disclosed in the '057 and '420 patents to Green et al. are adapted to surgically apply clips to body tissue in endoscopic procedures.

While the above developments represent major advances in endoscopic and laparoscopic instrumentation, the present invention is directed to further improvements whereby the handle section incorporates a pneumatic system to alleviate the degree of manually applied force required to actuate the instrument.

Surgical instruments having handle mechanisms which incorporate pneumatic systems or self contained powered units are described in U.S. Pat. Nos. 3,618,842, 3,643,851, 3,662,939, 3,717,294, 3,815,476 and 3,837,555. Typically, the pneumatic system in these instruments include a replaceable cylinder which supplies gas (e.g., carbon dioxide or nitrogen) at relatively high pressure (e.g., 800 psig.) to power the instrument. The high pressure gas used in these instruments requires the instruments to be of relatively heavy construction in order to solely accommodate the high pressure involved. Consequently, these design requirements preclude the incorporation of such high pressure gas units in endoscopic instrumentation which typically is more delicate in construction and is not capable of withstanding the high pressure delivered by these units.

Therefore, there is a need for a pneumatic system or self-powered gas unit of relatively low pressure that can be incorporated in an actuating or handle mechanism of an endoscopic or laparoscopic instrument, and which is capable of generating the substantial forces required to operate the instrument. Also, although it may be desirable to perform most of the functions of the endoscopic apparatus using the self-powering elements in the apparatus, it may also be desirable for the initial function to be at least partly manual. For example, if the initial function is to advance the staple for pre-positioning, it is preferably initiated manually so that it can be performed slowly and precisely and the results inspected and corrected if necessary before the automatic self-powered portion of the operating sequence begins. See, for example, U.S. Pat. Nos. 4,349,028 and 4,331,277 to Green.

One embodiment of the present invention contemplates an endoscopic apparatus adapted to endoscopically apply staples to attach a surgical mesh to body tissue to reinforce a surgical repair of the body tissue, as in hernia repair.

In hernia surgery a suitable mesh material is generally sutured over the opening in the tissue. The mesh material is often also attached by sutures and left within the opening to act as a reinforcing agent for tissue regrowth in the area of the surgery. One example of a mesh material currently utilized in hernia surgery includes a polypropylene material marketed by the Ethicon Division of Johnson & Johnson, New Brunswick, N.J., under the trademark MARLEX. Another example of a mesh material is a tri-fluoroethylene material marketed by W. L. Gore & Associates, Newark, Del., under the tradename GORE-TEX. Another example is a polypropylene mesh marketed by the assignee under the trademark SURGIPRO™.

U.S. Pat. No. 4,944,443 to Oddsen et al. discloses an instrument and method for applying and forming staples into body tissue to suture a hernial opening. The staple is applied to two pieces of body tissue on opposite sides of the opening which are gripped, approximated and held together by a tissue positioning assembly. U.S. Pat. No. 4,919,152 to Ger relates to a surgical instrument for placing a single clip which is proposed for use in direct hernia repair for closing sacs having narrow neck openings.

Commonly assigned U.S. patent application Ser. No. 07/782,290, filed Oct. 18, 1991, discloses a novel apparatus adapted to endoscopically apply staples for attaching objects such as surgical mesh in a manner which positively secures the object to body tissue without danger of separation thereof after the attachment is completed. This apparatus has proven to be highly effective in performing endoscopic surgical procedures, particularly, hernia repair.

The present invention is related to a novel endoscopic stapler incorporating a low pressure pneumatic system to provide the necessary forces to perform the stapling function. In accordance with the preferred embodiment of the present invention, the apparatus incorporates an initial or a staple-prepositioning function to facilitate proper placement of the staple relative to surgical mesh and body tissue prior to completion of the staple firing stroke.

SUMMARY OF THE INVENTION

An endoscopic surgical stapling apparatus comprises a frame and a generally elongated endoscopic portion connected to the frame and extending distally therefrom. The endoscopic portion includes means for storing a plurality of staples, means for individually advancing the staples for positioning adjacent body tissue and means for at least partially closing each staple. The apparatus further comprises pneumatic means which are disposed within the frame for at least partially activating the staple advancing means. The pneumatic means comprises a pressurized gas supply and pneumatic actuator means including a cylinder in fluid communication with the pressurized gas supply and defining an opening at a distal end thereof, and a piston disposed within the opening and adapted to advance in response to admission of gas therewithin.

The apparatus also comprises first operable means disposed within the frame for distally advancing the staple pusher of the staple advancing means from an initial unadvanced position to a first predetermined position. Preferably, the first operable means is adapted to selectively advance the staple pusher between the initial position and the first predetermined position. The first operable means includes a ratchet and an associated pawl which is adapted to prevent proximal movement of the staple pusher except when the staple pusher is advanced to the first predetermined position whereby the pawl is released so as to permit return of the staple pusher to the initial position. The first operable means may be manually operated by a trigger or a lever mechanism.

The apparatus also comprises second operable means for actuating the pneumatic means to distally drive the staple pusher beyond the first predetermined position to a second advanced position corresponding to at least partially closing each staple by the staple closing means. The second operable means is manually operated by an actuating mechanism which includes a firing button pivotally mounted to the frame and operatively connected to a firing link of the second operable means. The firing link is engageable with the piston of the pneumatic means, whereby pivotal movement of the firing button in one direction causes distal longitudinal movement of the firing link and corresponding distal movement of the piston. Such distal movement of the piston causes release of pressurized gas from the pressurized gas supply in an amount sufficient to establish the force to distally drive the piston to advance the staple pusher means to the second advanced position.

In an alternative preferred embodiment of the apparatus of the present invention, the first operable means is operatively connected to the pneumatic means such that actuation of the first operable means activates the pneumatic means to distally drive the piston and the staple pusher. Upon actuation of the first operable means the staple pusher is advanced to the first predetermined position and prevented from advancing beyond this position by engaging means located within the frame. The second operable means is adapted to release the engaging means to permit continued distal movement of the staple pusher beyond the first predetermined position to a second advanced position corresponding to at least partially closing the staple by the staple closing means.

The present invention is also directed to an apparatus for endoscopic application of surgical staples adapted to attach an object to body tissue. The apparatus comprises a handle member adapted to be gripped by hand and a generally elongated endoscopic portion connected to the handle member and extending distally therefrom. The endoscopic portion includes at least one staple, a staple pusher for individually advancing the one staple distally for positioning adjacent the body tissue and an anvil for closing the staple. The handle member comprises a pneumatic system including a supply of low pressure gas. The pneumatic system is adapted to convert the low pressure gas into a force to advance the staple pusher. The apparatus further comprises a first transmission for distally advancing the staple pusher from an initial position to a first predetermined position and a second transmission connected to the pneumatic system to actuate the pneumatic system to distally drive the staple pusher beyond the first predetermined position to a second advanced position to close the staple about the anvil.

In accordance with an alternative preferred embodiment, the apparatus for endoscopic application of surgical staples adapted to attach an object to body tissue comprises a handle member and a generally elongated endoscopic portion connected to the handle member and extending distally therefrom. The endoscopic portion includes means for storing a plurality of staples, means for individually advancing the staples distally for positioning adjacent the body tissue and anvil means for closing the staple in a manner to encompass at least a portion of the object and to penetrate the body tissue to attach the portion of the object to the body tissue. The handle member comprises a pneumatic system including a supply of low pressure gas. The pneumatic system is adapted to convert the low pressure gas into a force to activate the staple advancing means. The apparatus further comprises transmission means for actuating the pneumatic means to distally advance the staple advancing means, engaging means associated with the staple advancing means for selectively preventing distal movement of the staple advancing means beyond a first predetermined position and release means for releasing the engaging means to permit further advancing movement of the staple advancing means beyond the first predetermined position to a second fully advanced position to close the staple about the anvil means.

BRIEF DESCRIPTION OF THE DRAWINGS

Preferred embodiments of the invention are described hereinbelow with reference to the drawings wherein:

FIG. 1A is a perspective view of the distal end portion of the apparatus of FIG. 1 illustrating an alternative embodiment for pivoting the staple storage magazine;

FIG. 6 is an enlarged cross-sectional view of the pawl and ratchet system in the handle, illustrating the positioning of the system after proximal movement of the staple advancing trigger;

FIG. 7 is a cross-sectional view similar to FIG. 5 with the staple firing button in the depressed advanced position corresponding to firing of the staple;

FIG. 19 is a cross-sectional view similar to FIG. 18 with the staple firing button in an advanced position to actuate the pneumatic system to initially advance the staple;

FIG. 38 is an enlarged cross-sectional view taken along lines 38—38 of FIG. 1 illustrating the rotating mechanism for the endoscopic portion and the system for pivoting the staple storage magazine from the proximal end;

FIG. 39 is a cross-sectional view taken along lines 39—39 of FIG. 38;

FIG. 40 is a cross-sectional view taken along lines 40—40 of FIG. 38 illustrating the system for providing pivotal motion of the staple storage magazine located at the distal end;

FIG. 46 is a cross-sectional view taken along lines 46—46 of FIG. 1 illustrating the distal end of the instrument including the pivotal staple magazine at three positions;

FIG. 47 is a cross-sectional view taken along lines 47—47 of FIG. 46 illustrating the staple next in line and the pusher plate provided for advancing the staple toward a staple closing anvil;

FIG. 48 is a cross-sectional view of the distal end of the instrument shown in engagement with a surgical mesh positioned against body tissue prior to firing the staple;

FIG. 49 is a cross-sectional view taken along lines 49—49 of FIG. 48;

FIG. 50 is a cross-sectional view similar to FIG. 48 of the distal end of the instrument during the firing of the staple and after penetration into the mesh and body tissue, but prior to closure;

FIG. 51 is a view similar to FIG. 49, taken along lines 51—51 of FIG. 50;

FIG. 52 is a cross-sectional view of the distal end of the instrument after closure of the staple to attach the surgical mesh to the body tissue;

FIG. 53 is a cross-sectional view taken along lines 53—53 of FIG. 52 illustrating the staple ejection system for releasing the closed staple from the anvils after firing;

FIG. 54 is a cross-sectional view similar to FIG. 52 illustrating the staple after closure about the surgical mesh and body tissue and the distal end of the instrument withdrawn from the surgical mesh;

FIG. 55 is a cross-sectional view taken along lines 55—55 of FIG. 54;

FIG. 56 is a cross-sectional view of the distal end portion of the staple storing magazine of the instrument after firing a staple;

FIG. 57 is a frontal view of a repair in body tissue illustrating one example of an arrangement of staples of the invention for attachment of reinforcing surgical mesh to the tissue;

FIG. 58 is a perspective view of a staple constructed according to the invention for attaching surgical reinforcing mesh to body tissue over a surgical repair; and FIG. 59 is another example of arranging the staples for attachment of the reinforcing surgical mesh to the body tissue in the area of a hernia repair.

DETAILED DESCRIPTION OF THE PREFERRED EMBODIMENTS

Although the principles of the invention are applicable to various types of surgical fastener instruments, the invention will be fully understood from the following illustration of its application in a surgical fastener instrument for hernia repair disclosed in commonly assigned U.S. patent application Ser. No. 07/782,290, filed Oct. 18, 1991, application Ser. No. 07/861,065, filed Mar. 31, 1992, which is a continuation-in-part of application Ser. No. 7/782,290 and application Ser. No. 07/950,425, filed Sep. 23, 1991, which is a continuation-in-part of application Ser. No. 07/861,065, the contents of each application being incorporated herein by reference.
General Following a general description of the instrument, the description will be divided into separate sections to describe the structure and the desired movements produced thereby. Those sections include the handle system, the staple storage magazine pivoting system, the endoscopic section and staple firing system, the staple storage magazine, the staple closing system and the staple. Also a kit for attaching objects such as surgical mesh is described.
The Instrument Referring initially to FIG. 1, there is illustrated in perspective view the apparatus 10 incorporating the novel handle system of the present invention and particularly adapted for endoscopic application of surgical staples to attach surgical mesh to body tissue during hernia repair. Except where noted otherwise, the materials utilized in the components of the apparatus generally include such materials as polycarbonate for housing sections and related components, and stainless steel for such components which transmit forces. One preferred polycarbonate material is LEXAN brand polycarbonate available from General Electric Company. Other specific preferred materials such as nylon or glass filled nylon (for strength) are also utilized. However, equivalent alternative materials will readily come to the mind of those skilled in the art.

Figure 1:
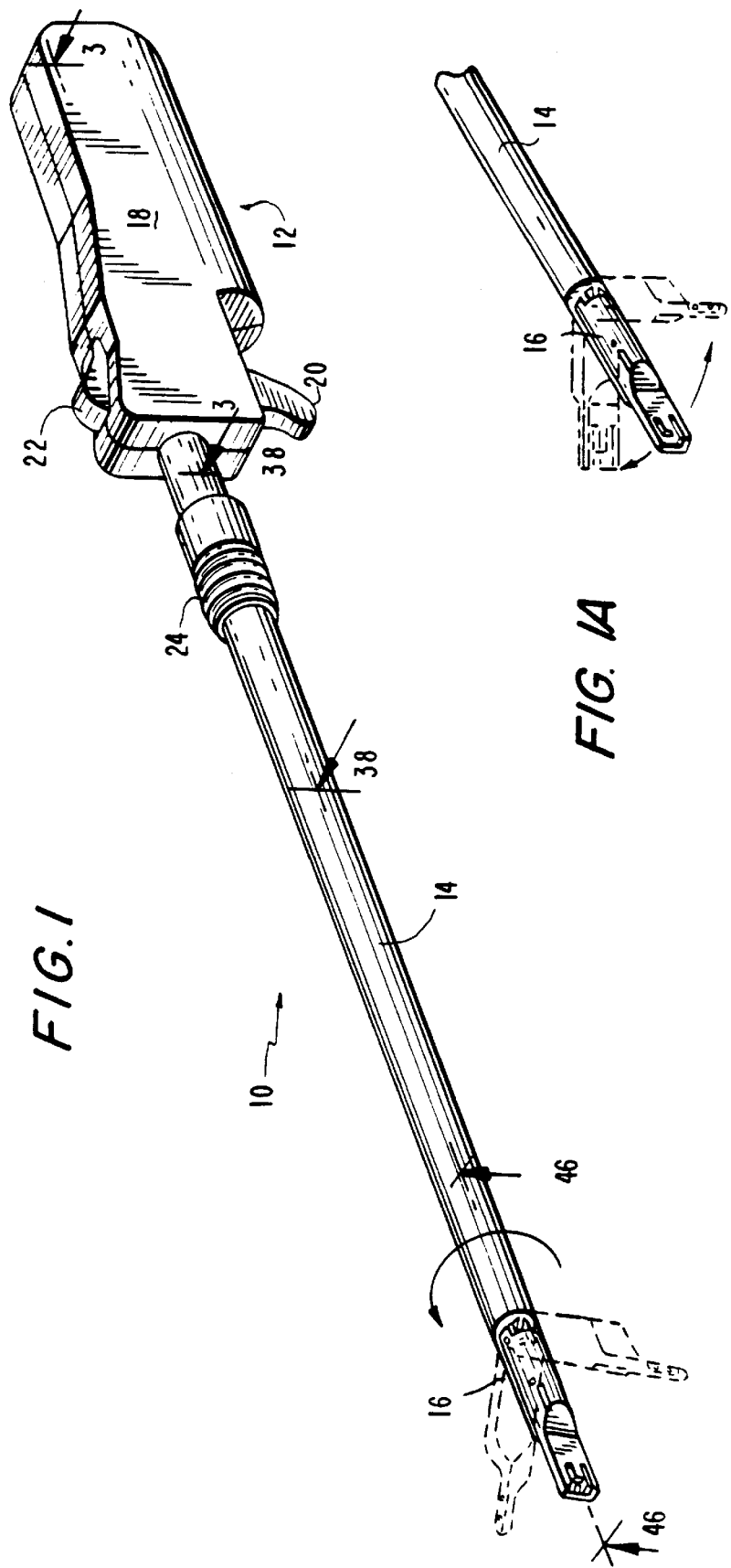
FIG. 1 is a perspective view of an apparatus incorporating the novel handle and pneumatic system of the present invention and adapted to apply surgical staples to attach objects to body tissue.

Apparatus 10 includes a handle portion 12 and an endoscopic section 14 having at its distal end portion a staple storage magazine 16 which pivots with respect to at least one side of the longitudinal axis extending centrally through the endoscopic section as shown in FIG. 1A. Generally, staple storage magazine 16 will selectively pivot up to about 45 degrees with respect to the aforesaid longitudinal axis. In the illustration of FIG. 1 the staple storage magazine 16 is shown in general alignment with the longitudinal axis of the endoscopic section and in phantom to illustrate a range of movement. The total range of pivotal motion of the staple storage magazine 16 as shown is approximately 90 degrees, i.e. 45 degrees to each side of neutral.

Referring generally to FIG. 1, the handle 12 of instrument 10 includes frame 18, staple prepositioning trigger 20 which is slidably mounted to the frame and firing button 22 which is pivotally mounted to an upper portion of the frame. Trigger 20 is proximally moved towards the main portion of frame 18 to initially selectively position the staple in a slightly advanced position prior to firing. Firing button 22 is pivoted towards frame 12 to actuate a pneumatic system to fire the staple.

A double knurled finger operative collar 24 is rotatable and adapted to rotate the entire endoscopic section 14 a full 360 degrees as will be described hereinbelow, while proximal movement of the operative collar 24 produces pivotal motion of the staple storage magazine to one of the positions shown in phantom in FIG. 1. To achieve the other position shown in phantom in FIG. 1, the collar 24 may be simply rotated 180 degrees thereby rotating the entire endoscopic section and causing the position of the magazine 16 to be reversed as shown to the other position shown in phantom. Thus, it can be seen that the combination of full rotation of the endoscopic section and the pivotal movement of the staple storing magazine facilitates a wide range of articulation of the distal end of the staple magazine 16, thus facilitating application of staples over a wide range of locations (±180 degrees) and in any of a plurality of orientations. In the embodiment of the invention shown in the Figures, when the collar 24 is moved to its proximalmost position the staple magazine is in one of the positions shown in phantom in FIG. 1, i.e. at an angle with respect to the longitudinal axis of the instrument. When the collar 24 is advanced to the distalmost position the staple magazine assumes the position shown in FIG. 1, i.e. in alignment with the longitudinal axis of the instrument.

Thus, in the preferred embodiment of FIG. 1, it can be seen that the full 90 degrees of movement of the magazine may be achieved simply by longitudinal movement of collar 24 in combination with full rotation of the endoscopic section. The longitudinal movement of collar 24 causes pivotal movement of the staple storing magazine to 45 degrees in one direction and rotation of the endoscopic section provides completion of the articulation of the magazine. Both of these movements in combination, facilitate a wide range of maneuverability of the distal end of the staple magazine 16, thus facilitating application of staples over a wide range of locations (±180 degrees) and in any of a plurality of orientations.

Alternatively, the positions of the staple storing magazine 16 may be achieved as shown in FIG. 1A, i.e. by movement of the magazine between zero degrees and about 45 degrees on either side of the longitudinal axis. In such arrangement, to achieve the positions shown in phantom in FIG. 1A, the collar 24 is moved distally and proximally, equal distances on either side of a neutral detent. Movement in one direction would pivot the magazine to one side and movement in the other direction would cause pivotal movement of the magazine in the opposite direction. The directions selected would be arbitrary. However, in this last described embodiment the orientation of the magazine would be the same throughout the 90 degree pivoting range, whereas in the preferred embodiment of FIG. 1, the orientation of the magazine when on one side is opposite the orientation when on the other. Further, in this embodiment the endoscopic section will be somewhat longer to accommodate the additional movement of collar 24.

The Handle Section

Figure 2:
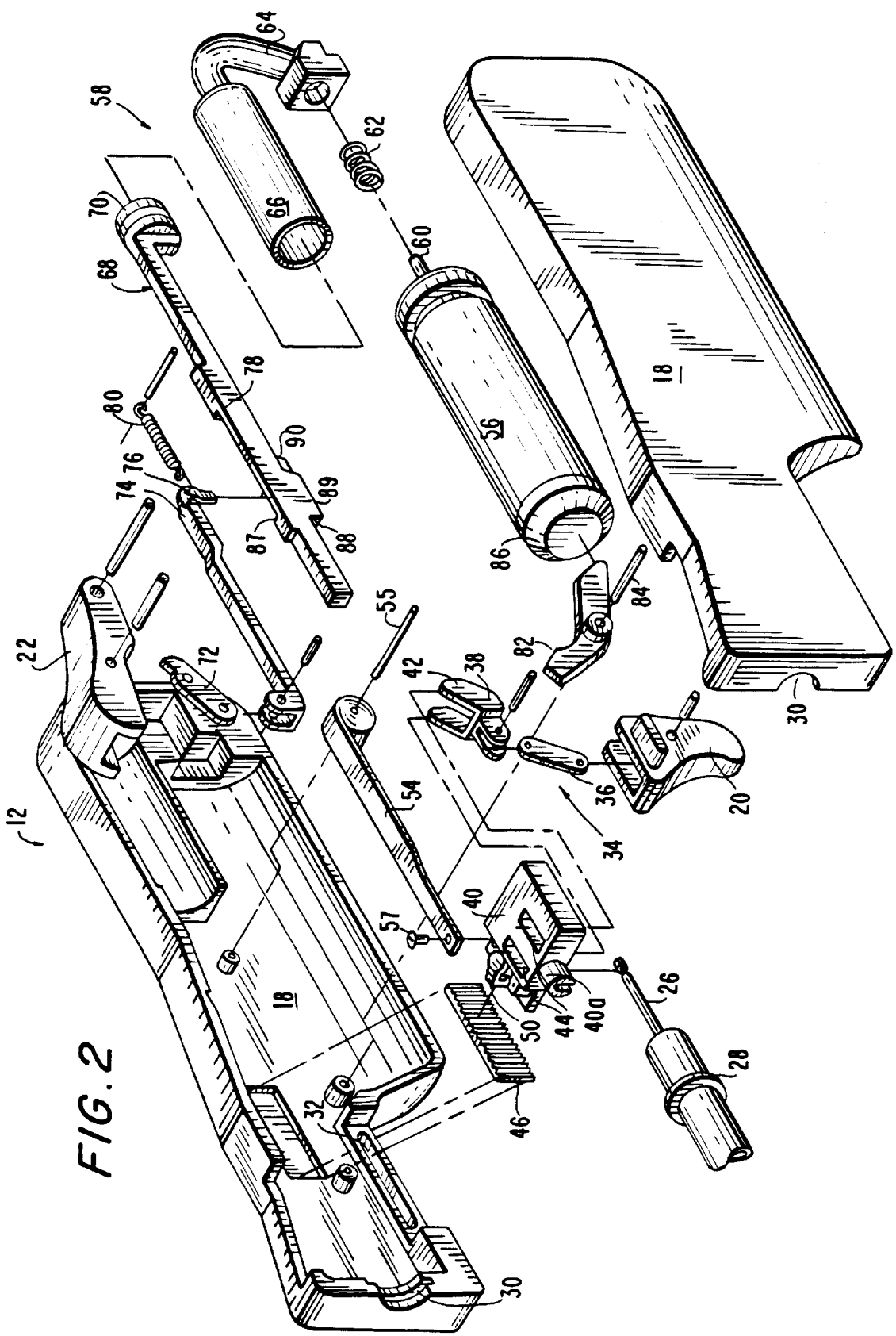
FIG. 2 is an exploded perspective view with parts separated of the handle and pneumatic system of the apparatus of FIG. 1.
Figure 3:
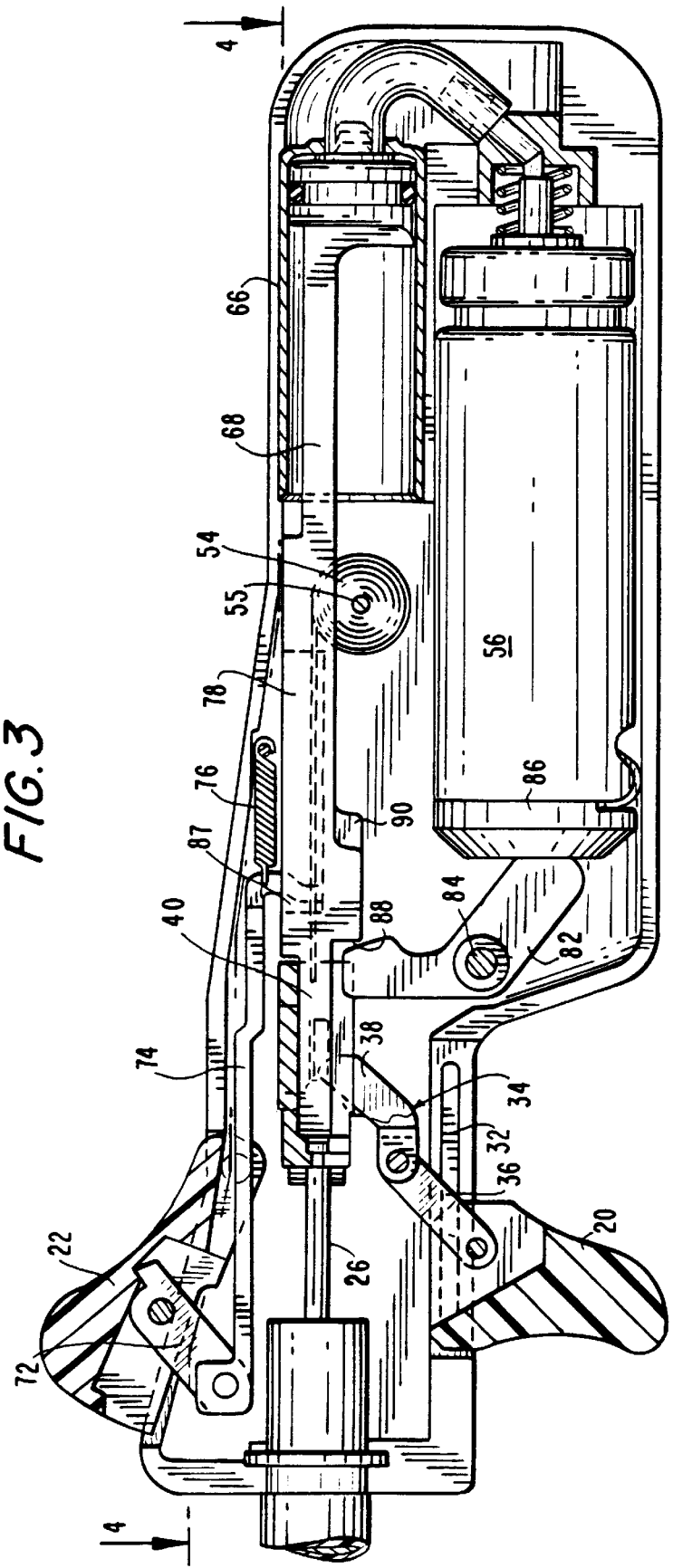
FIG. 3 is a cross-sectional view taken along lines 3—3 of FIG. 1, illustrating the handle system of the apparatus in the initial position.

Referring to FIG. 2, there is shown an exploded perspective view with parts separated, of the novel handle system 12 of the instrument with associated components. The handle system 12 incorporates a pneumatic system which powers the staple firing stroke of the instrument. As previously noted, the handle is comprised of an outer frame or housing 18 preferably formed of separate sections as shown, of polycarbonate material. The separate parts shown are attached by welding, adhesives, etc. FIG. 3 illustrates a cross-sectional view of the handle mechanism taken along lines 3—3 of FIG. 1.

The ultimate purpose of the handle system 12 is to provide distal movement to the pusher rod 26 which extends through the endoscopic section 14 and ultimately fires the staples. In the embodiment shown, the endoscopic section is intended to be permanently and rotatably attached to the instrument via rim 28 formed on a proximal end of endoscopic section 14 which is received within correspondingly positioned and dimensioned arcuate recesses 30 formed in each part of frame 18 during assembly. Other conventional means for rotatably connecting endoscopic section 14 to handle 12 can readily be determined by one skilled in the art.

Handle 12 is contemplated to be entirely disposable. However, it is also contemplated and within the scope of the invention to construct the endoscopic section to be selectively detachable whereby the handle may be sterilized and reused, or the endoscopic section can be sterilized, and the staple storage magazine re-loaded with staples for re-use. Alternatively a replacement staple magazine, and optionally a replacement endoscopic section, may be detachably secured to a disposable handle for multiple use during a single surgical procedure. Thus, any combination of alternatives may be incorporated within the scope of the present invention.

Referring now to FIG. 2 in conjunction with FIG. 3, the novel handle system 12 will be described in detail. Handle 12 includes a staple positioning mechanism operable by single finger trigger 20 which initially advances or "prepositions" a staple prior to firing and a firing mechanism operable by firing button 22 which actuates the pneumatic system to fire the staple. The staple positioning mechanism enables the operator to selectively advance a staple so that the staple legs protrude from the staple magazine. This initial advancement of the staple facilitates attachment of the mesh to the staple and positioning of the staple relative to the body tissue.

Trigger 20 is mounted for longitudinal movement within channel 32 of frame 18 and is operatively connected to pusher rod 26 through a linkage mechanism, identified generally as reference numeral 34, to produce corresponding longitudinal movement to the pusher rod 26. Linkage mechanism 34 includes trigger link 36, U-shaped driving link 38 connected to the trigger link and pusher housing 40. U-shaped driving link 38 includes a pair of upwardly extending members 42 which are received within correspondingly dimensioned and positioned elongated apertures 44 formed in pusher housing 40 to operatively connect the two components.

Figure 5:
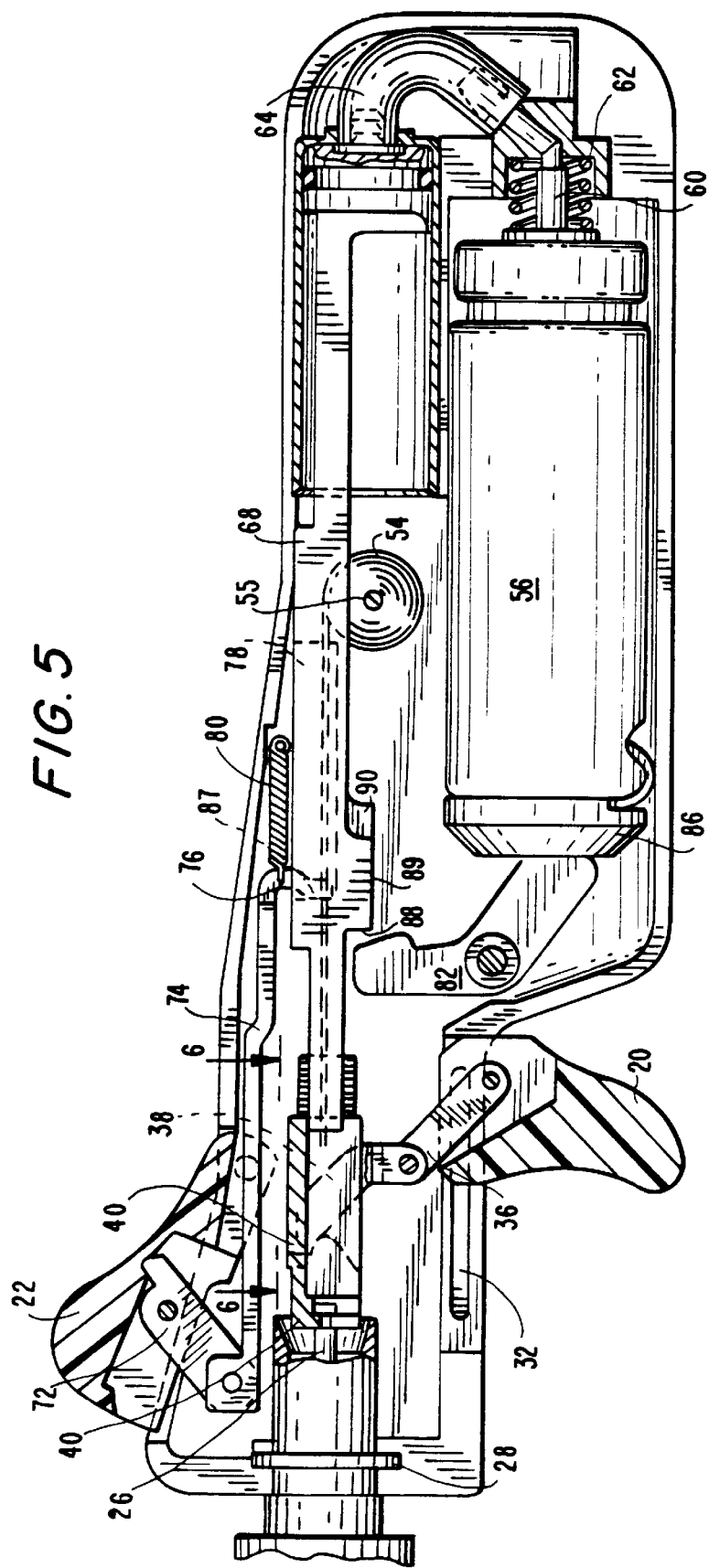
FIG. 5 is a cross-sectional view similar to FIG. 3 with the staple advancing trigger in the full proximal position to selectively partially advance a staple prior to firing.

Pusher housing 40 includes a pusher rod receiving portion 40a which receives the proximal end portion of pusher rod 26 to connect the housing to the rod. Pusher housing 40 advances distally in response to proximal movement of trigger 20 to advance pusher rod 26 towards staple cartridge 16 to position the staple in an advanced position partially exposed from the distal end of staple magazine 16. FIG. 5 illustrates the corresponding movement of pusher housing 40 and pusher rod 26 when trigger 20 is moved proximally.

Figure 4:
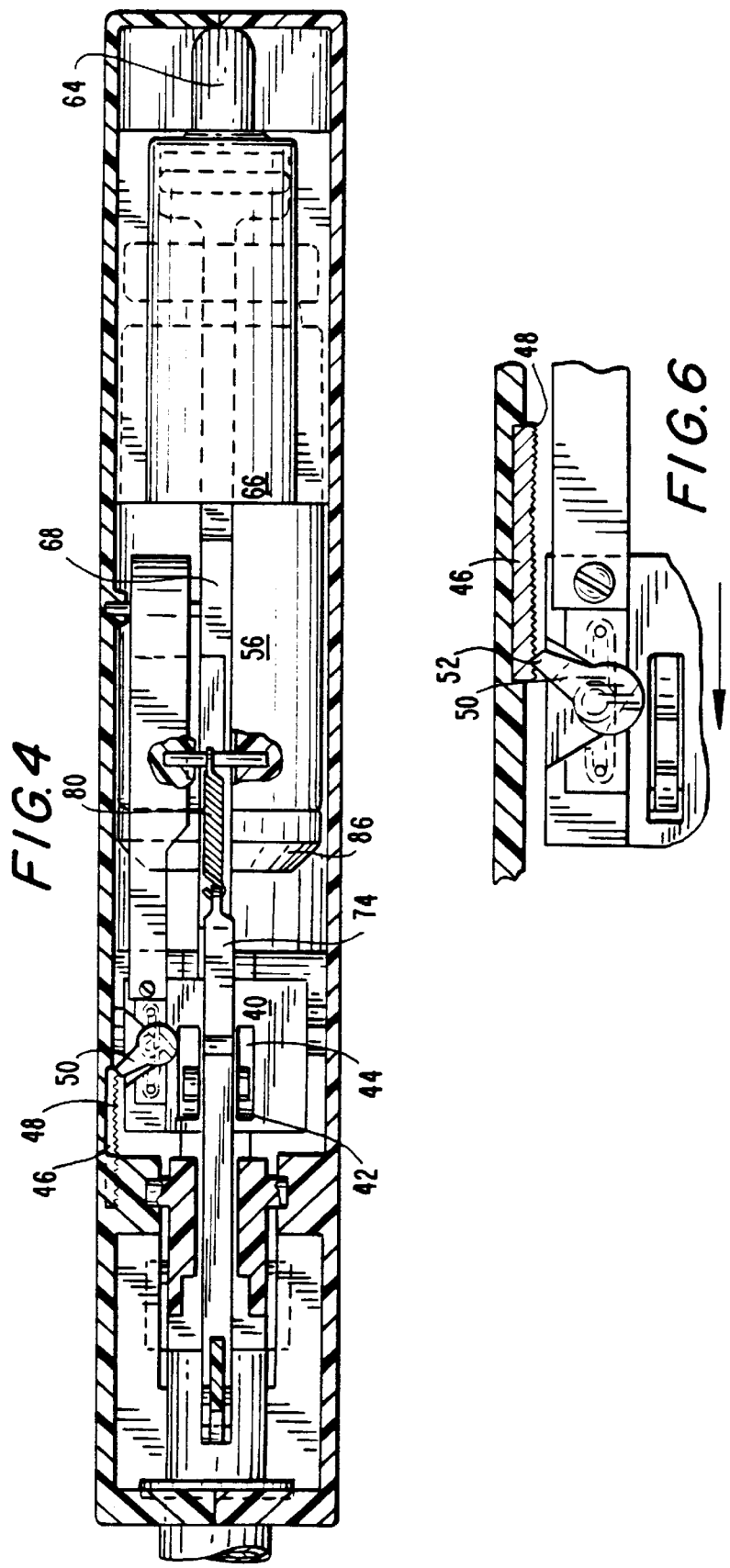
FIG. 4 is a cross-sectional view taken along lines 4—4 of FIG. 3 illustrating the mechanism for providing distal movement to advance and to close staples at the distal end.

Referring now to FIGS. 2, 4 and 6, the structure and function of the uni-motion clutch mechanism will be described. This clutch mechanism prevents proximal movement of pusher housing 40 in the event trigger 20 is released after squeezing motion of the trigger has begun but before the full stroke is completed. The clutch mechanism is self-releasing when pusher housing 40 reaches the distalmost position, thus permitting the entire pusher housing to return to the pre-advanced, or proximalmost condition, and trigger 20 to also return to the initial position.

A ratchet plate 46 is fixed to frame 18 and possesses a surface defined by a plurality of triangular shaped parallel ridges 48 as best shown in FIG. 6. Pawl 50 is rockably mounted for distal and proximal movement with pusher housing 40 through frame 18, and is biased toward ratchet plate 46 by a resilient wire spring or the like. The location of pawl 50 shown in FIG. 4 corresponds to the initial condition of the apparatus prior to proximal movement of trigger 20 with the pawl 50 located proximal of ratchet plate 46. Pawl 50 is preferably of stainless steel while ratchet plate 46 is made of brass or other compatible material.

While trigger 20 is squeezed or moved proximally producing distal motion to pusher rod 26, pawl 50 engagably slides distally past the ratchet surface 48 of ratchet plate 46 as shown in FIG. 6 such that one corner of the tip 52 of the pawl 50 sequentially engages each right angled ridge of ratchet plate 46 to thereby prevent proximal movement of the pusher rod 26 in the even trigger 20 is released by the operator. The engagement of pawl 50 with ratchet plate 46 provides audible confirmation that pusher housing 40 and pusher rod 26 are moving distally since the user will hear a series of progressive audible clicks. This action continues with the tip 52 of pawl 50 sliding past the ratchet surface of the ratchet plate 46 until the pawl is positioned distally of the distalmost tooth. Preferably, trigger 20 is in its distalmost position as shown in FIG. 6 when pawl 50 clears ratchet surface 48.

Upon clearing ratchet surface 48, the pawl 50 moves proximally with pusher rod 26 as described under the action of negator spring 54 which is attached to pusher housing 40. The end portion 52 of pawl 50 which is now free, engages the distal end of the ratchet plate 46 causing the pawl to rock to a reverse direction so as to slide proximally past ratchet surface 48 of ratchet plate 46 without interference to the proximal movement of the pusher rod 26. Thus, it can be seen that the clutch mechanism as described will effectively permit squeezing trigger 20 while maintaining all positions midway through the stroke, and while permitting return motion thereof after the trigger has moved to its distalmost position or upon completion of the firing stroke as will be appreciated from the description below. The clutch mechanism allows the operator to selectively advance the staple beyond the distal end of staple magazine. The operator may then turn full attention to locating the prepositioned staple in the desired target location, at which point the pivoting of the trigger mechanism may be resumed and the cycle completed or the pneumatic system actuated to fire the staple. This staple prepositioning feature greatly facilitates staple placement within the surgical mesh and body tissue. In the embodiment of FIG. 1, the staple prepositioning feature is mechanically actuated through trigger 20. Trigger 20 constitutes the "first means" or "first transmission" for distally advancing the staple rod 26 from an initial position to a first predetermined position.

Referring now to FIGS. 2, 3 and 5, negator spring 54 is formed of a resilient flat spring material and is coiled about rotational bar 55. The free end of negator spring 54 is attached to pusher housing 40 via anchor pin 57 as shown, while the spring 54 is normally biased toward the coiled configuration shown in FIG. 3. It can therefore be appreciated that upon firing the instrument negator spring 54 assumes control and returns pusher rod 26 to the initial proximal location by the automatic winding action of the negator spring to its original unloaded configuration. The constant force of negator spring 54 uniquely prevents the natural tendency of the user to rotate the hand as with springs which increase in force when progressing through a full spring cycle.

Referring again to FIGS. 2 and 3, the staple firing mechanism will now be described. The staple firing mechanism provides the power stroke to ultimately fire the staple for attachment to the body tissue and incorporates a pneumatic system having a container 56 of relatively low pressure gas and a pneumatic actuator identified generally by reference numeral 58. Container 56 is adapted for slight reciprocal longitudinal movement within frame 18 and includes a stem valve 60 at one end which releases the gas during proximal movement of the container 56. Container 56 is normally distally biased by spring 62 which is positioned about valve 60 between the container and a bearing wall of gas tube 64. Container 56 dispenses the relatively low pressure gas through stem valve 60 and tube 64 when firing button 22 is depressed.

The pressure of the gas in container 56 during operation of the apparatus is typically less than about 200 psig and preferably in the range from about 80 psig to about 160 psig. Any suitable non-toxic gas can be used including but not limited to halogenated hydrocarbons which are gaseous at room temperature, e.g., fluorinated hydrocarbons such as Freon 12 or chlorinated hydrocarbons such as Freon 15234.

Pneumatic actuator 58 includes pneumatic cylinder 66 and pneumatic piston 68 disposed within the cylinder 66. Cylinder 66 receives the gas emitted from container 56. Piston 68 is pneumatically sealed to cylinder 56 by "O" ring 70 and is mounted for reciprocal motion in the cylinder in response to admission of gas therewithin. Distal longitudinal movement of piston 68 advances pusher rod 26 as will be described in greater detail below.

Referring still to FIGS. 2 and 3, firing button 22 of the staple firing mechanism is operatively connected to a firing rod 74 via intermediate link 72, which rod 74 extends longitudinally from the firing button towards the proximal end of the apparatus. Firing rod 74 includes a transverse portion 76 on its proximal end which is received within a correspondingly positioned channel 78 formed in piston 68. Channel 78 is sufficient in length to accommodate transverse portion 76 of firing rod 68 during the full power stroke of piston 68.

A coiled spring 80 affixed to the proximal end of firing rod 74 normally biases the firing rod in the proximal direction. It can therefore be appreciated that after the pivotal motion of firing button 22 towards frame 18 from the position shown in FIGS. 3 or 5 to the position shown in FIG. 7 to advance firing rod 74, coiled spring 80 will return the firing rod 74 and the firing button 22 to its initial position of FIG. 3.

Referring again to FIGS. 2 and 3, a rocking lever 82 is pivotally mounted about pin 84 in the general midportion of frame 18. The upper portion of the rocking lever 82 is in engaging contact with bearing surface 88 of piston 68 while the lower portion of the rocking lever is in engaging contact with pusher disk 86 affixed to the distal end surface of container 56. Rocking lever 82 pivots in response to distal movement of piston 68.

Referring now to FIG. 7, depression of firing button 22 towards frame 18 advances firing rod 74 distally whereby the transverse portion 76 of the firing rod engages forward bearing surface 87 defined by recess 78 of piston 68 (FIG. 5) to cause corresponding advancing movement of the piston. Distal longitudinal movement of piston 68 causes counterclockwise pivotal movement of rocking lever 82 which causes the lower portion of rocking lever 82 to move gas container 56 in the proximal direction. Proximal movement of container 56 effects depression of valve 60 to thereby cause release of gas from container 56 and into cylinder 66 to drive piston 68 distally. Container 56 continues to release gas into cylinder 66 until the upper portion of rocking lever 82 clears bearing surface 89 defined on the lower side of piston 68. It is to be appreciated that the gas released by container 56 during the power stroke is sufficient to drive piston 68 into pusher housing 40 and to advance housing 40 and pusher rod 26 to fire a staple from staple magazine 16. The dimension or length of bearing surface 89 may be adjusted to control the amount of gases released by container 56.

After completion of the power stroke, piston 68 returns to its initial position under the influence of spring 54. During the return movement of piston 68, camming surface 90 formed in piston 68 causes the upper portion of rocking lever 82 to move transversely out of engagement with the piston to permit the piston 68 to assume its initial position. In the embodiment of FIG. 1, the staple firing mechanism is pneumatically actuated by movement of firing button 22 which causes the dispensing of pressurized gas and consequent moving of the staple pusher rod 26. Firing button 22 constitutes the "second means" or "second transmission" for distally advancing the staple pusher rod 26 to the second position.

Figure 8:
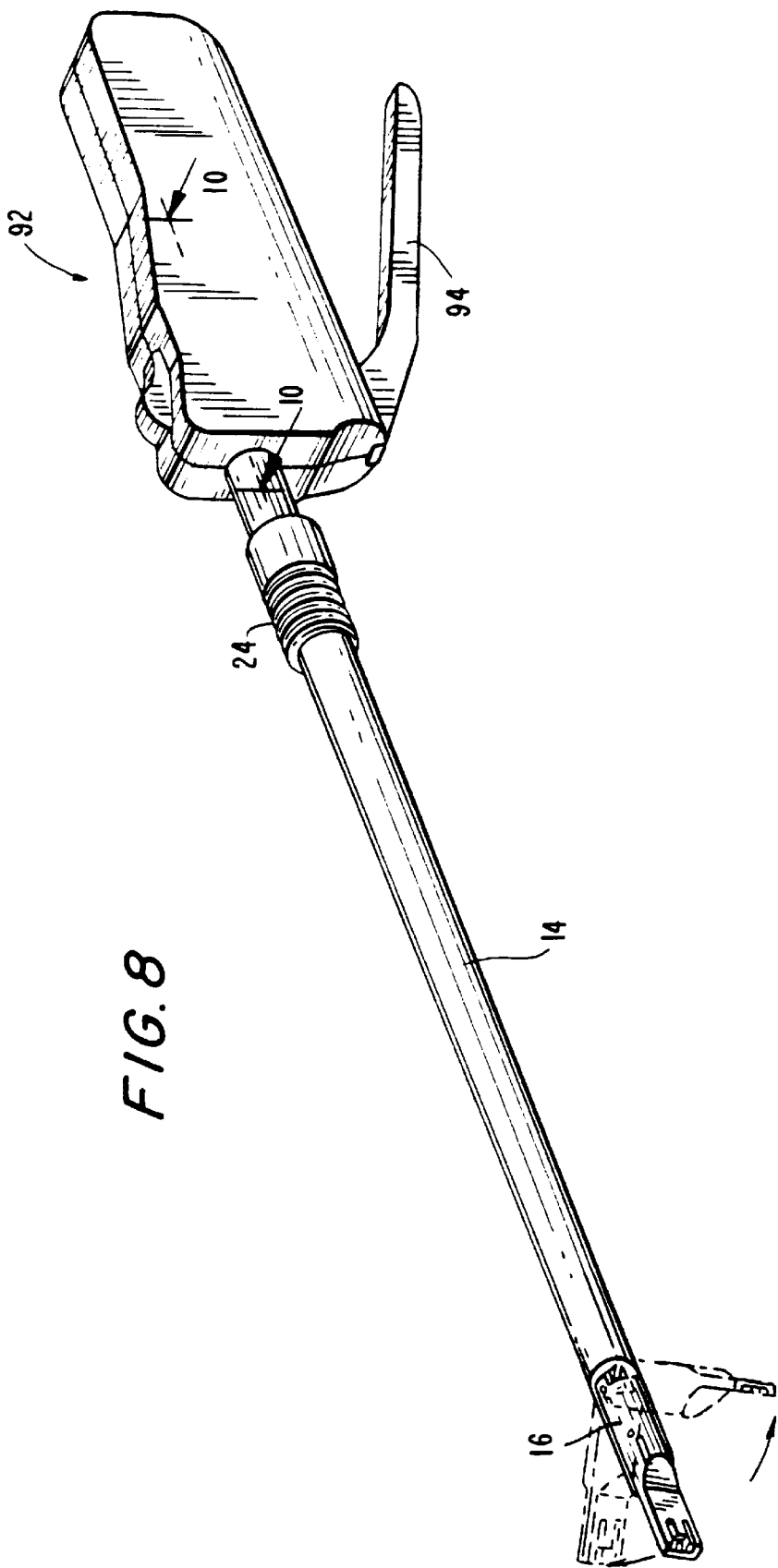
FIG. 8 is a perspective view of an alternative embodiment of the handle and pneumatic system to be used with the apparatus of FIG. 1.

Referring now to FIG. 8, there is illustrated an alternative embodiment of the handle system of the present invention. Handle 92 is similar in most respects to the handle of FIG. 1 except that the staple positioning mechanism has been modified. In particular, elongated lever 94 replaces the trigger 20 of the embodiment of FIG. 1. Lever 94 facilitates manipulation by the user by reducing the amount of force required to preposition the staple.

Figure 9:
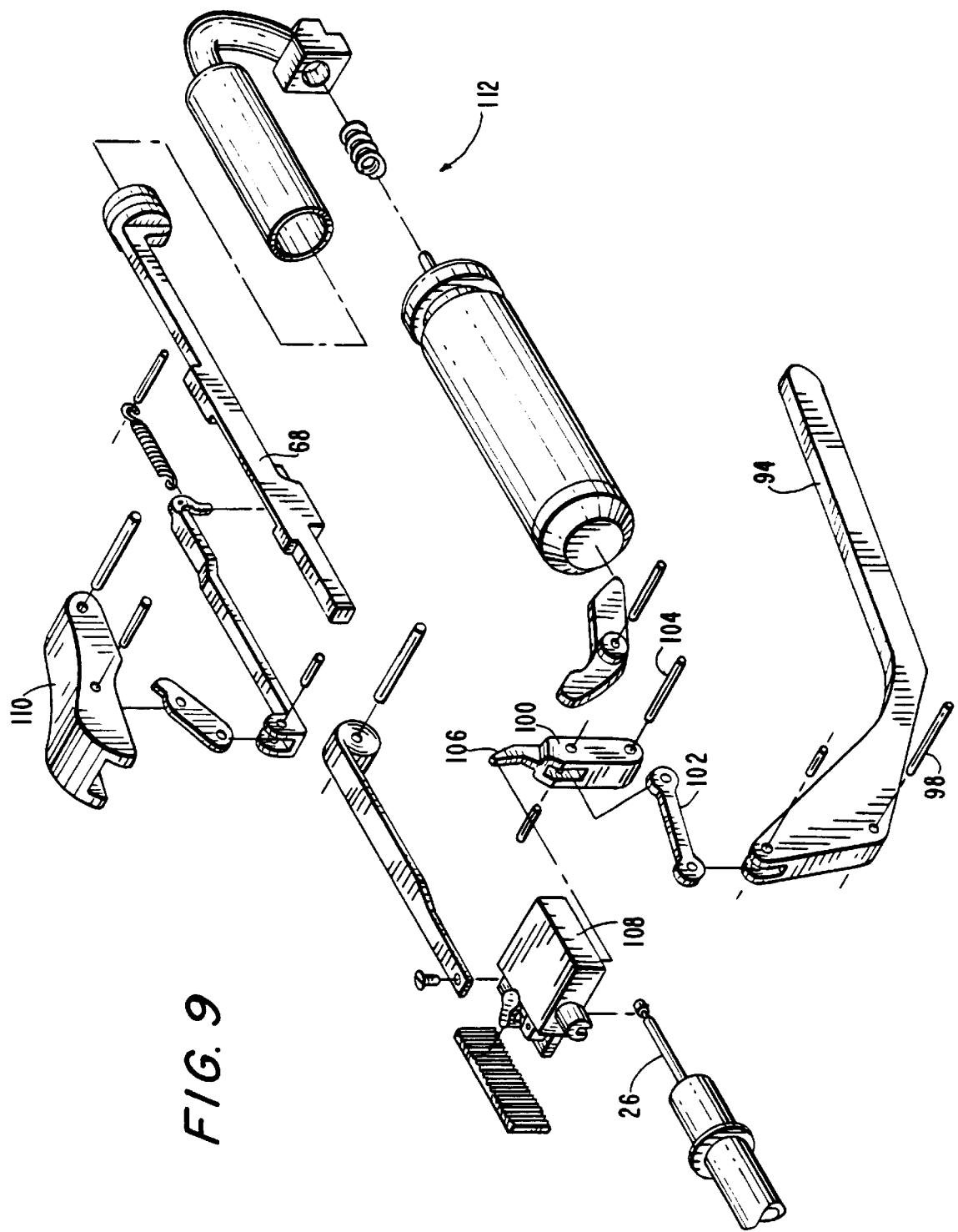
FIG. 9 is an exploded perspective view with parts separated of the handle and pneumatic system of FIG. 8.
Figure 10:
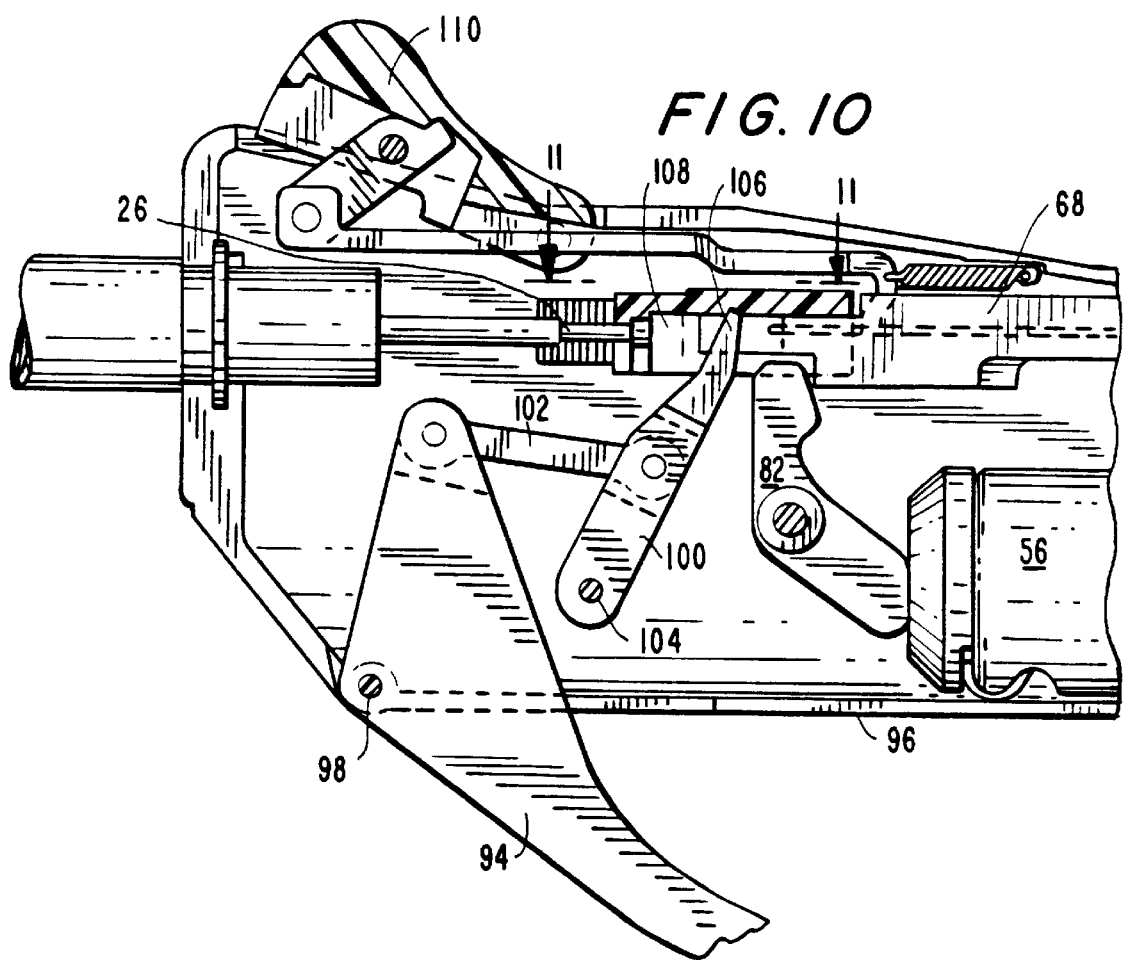
FIG. 10 is a cross-sectional view taken along the lines 10—10 of FIG. 8 illustrating the initial position of the handle system.

Referring now to FIGS. 9 and 10, lever 94 is pivotally mounted to frame 96 by mounting pin 98 and is operatively connected to driving link 100 by connecting link 102. Driving link 100 is pivotally mounted about pin 104 and pivots from the position shown in FIG. 10 to the position shown in FIG. 12 in response to movement of lever 94 towards frame 96. Driving link 100 includes an upstanding projection 106 which operatively engages a bearing wall defined within the interior of pusher housing 108 (See FIG.

Figure 12:
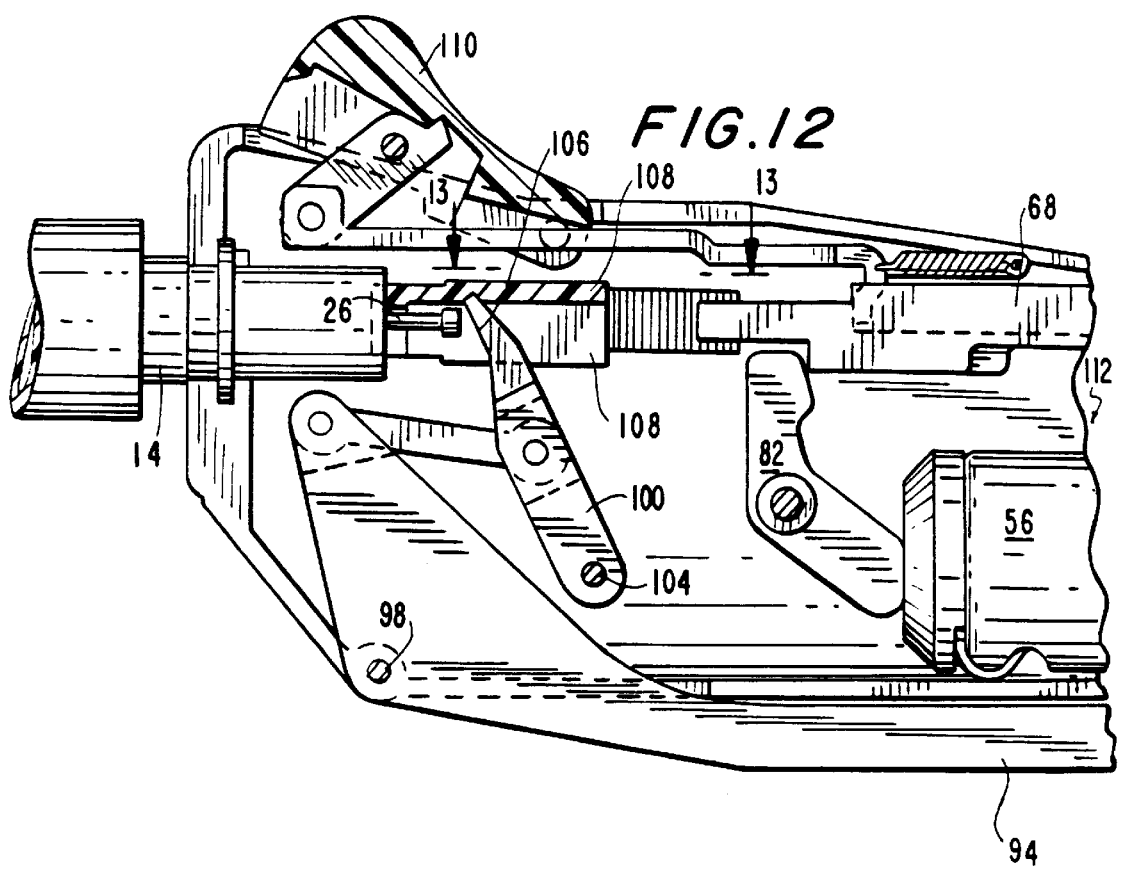
FIG. 12 is a cross-sectional view similar to FIG. 10 with the staple advancing lever in the fully pivoted position to selectively partially advance the staple prior to firing.

15) to cause corresponding advancing movement of the housing and pusher rod 26 to initially advance or preposition the staple. FIG. 12 illustrates lever 94 in a pivoted position adjacent frame 96, which position corresponds to the staple prepositioning stroke of the apparatus. In the embodiment of FIG. 8 the staple prepositioning feature is mechanically actuated through lever 94. Lever 94 constitutes the "first means" or "first transmission" for distally advancing staple rod 26 from an initial position to a first predetermined position.

Figure 14:
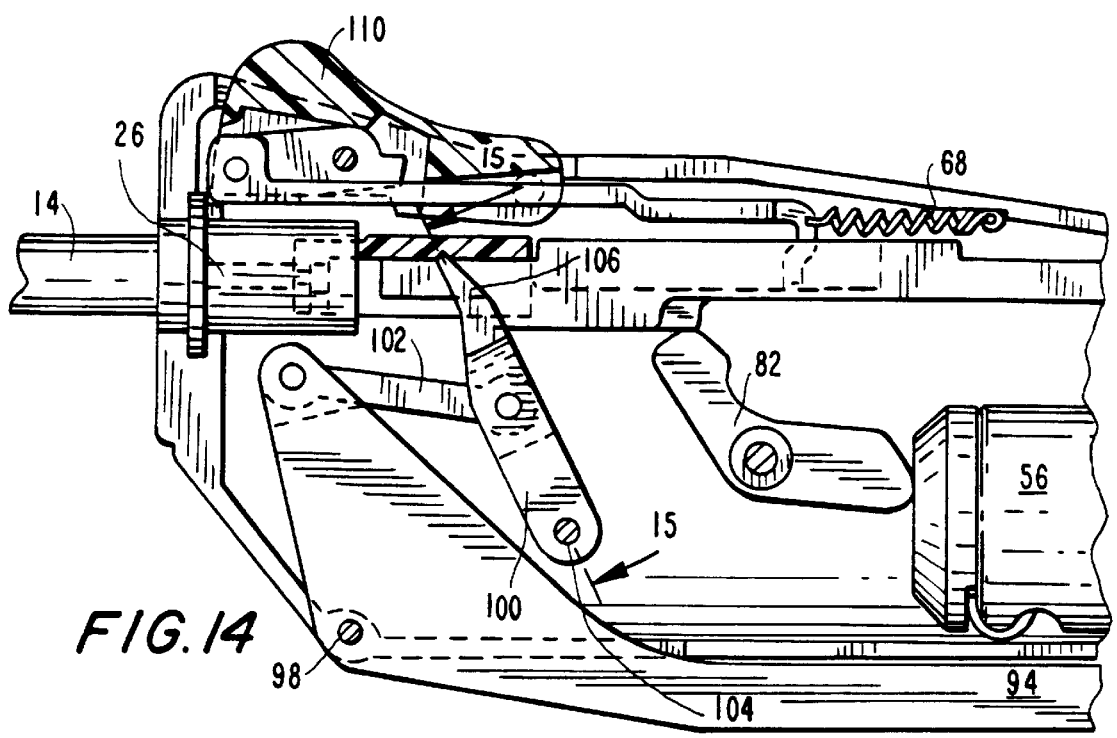
FIG. 14 is a cross-sectional view similar to FIG. 12 with the staple firing button in the depressed advanced position corresponding to firing of a staple.
Figure 15:
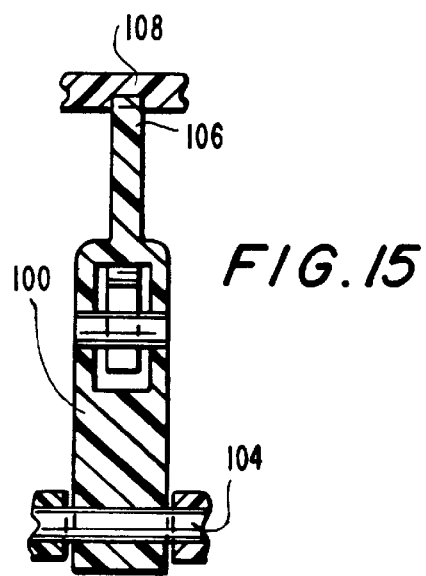
FIG. 15 is a cross-sectional view taken along lines 15—15 of FIG. 14 illustrating the relationship of the pivoting lever with the staple advancing mechanism.

Referring now to FIG. 14, the staple is ultimately fired by depressing firing button 110 to actuate the pneumatic system to provide the required force and desired movements of the staple firing mechanism. The components of the staple firing mechanism and pneumatic system 112 are structurally and functionally equivalent to their corresponding components described in the embodiment of FIG. 1.

Figure 11:
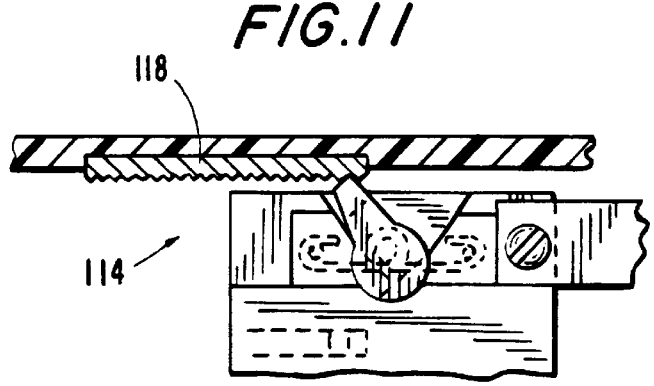
FIG. 11 is a cross-sectional view taken along lines 11—11 of FIG. 10 illustrating the positioning of the pawl and ratchet system prior to pivotal movement of the staple advancing lever.
Figure 13:
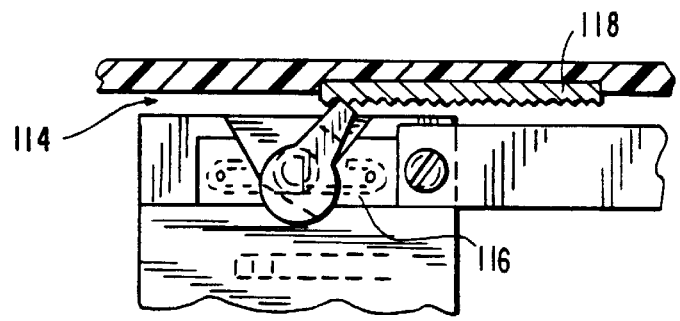
FIG. 13 is a cross-sectional view taken along lines 13—13 of FIG. 12 illustrating the positioning of the pawl and ratchet system after the initial advancement of the staple.

Handle 92 also includes a clutch mechanism, identified generally as reference numeral 114, including pawl 116 and ratchet plate 118 as shown in FIGS. 11 and 13. Clutch mechanism 114 is structurally and functionally similar to the clutch mechanism described in the embodiment of FIG. 1 and serves in preventing proximal movement of pusher housing 108 in the event lever 94 is released after squeezing motion of the lever has began but before the full stroke is completed. FIG. 11 shows pawl 116 in its proximalmost position relative to ratchet plate 118 prior to squeezing of lever 94 towards frame 96. FIG. 13 shows pawl 116 in its distalmost position after movement of lever 94 towards frame 96. In the embodiment of FIG. 8, the staple firing mechanism is pneumatically actuated by movement of firing button 110 which causes the dispensing of pressurized gas and consequent movement of the staple pusher rod 26. Firing button 110 constitutes the "second means" or "second transmission" for distally advancing the staple pusher rod 26 to the second position.

Figure 16:
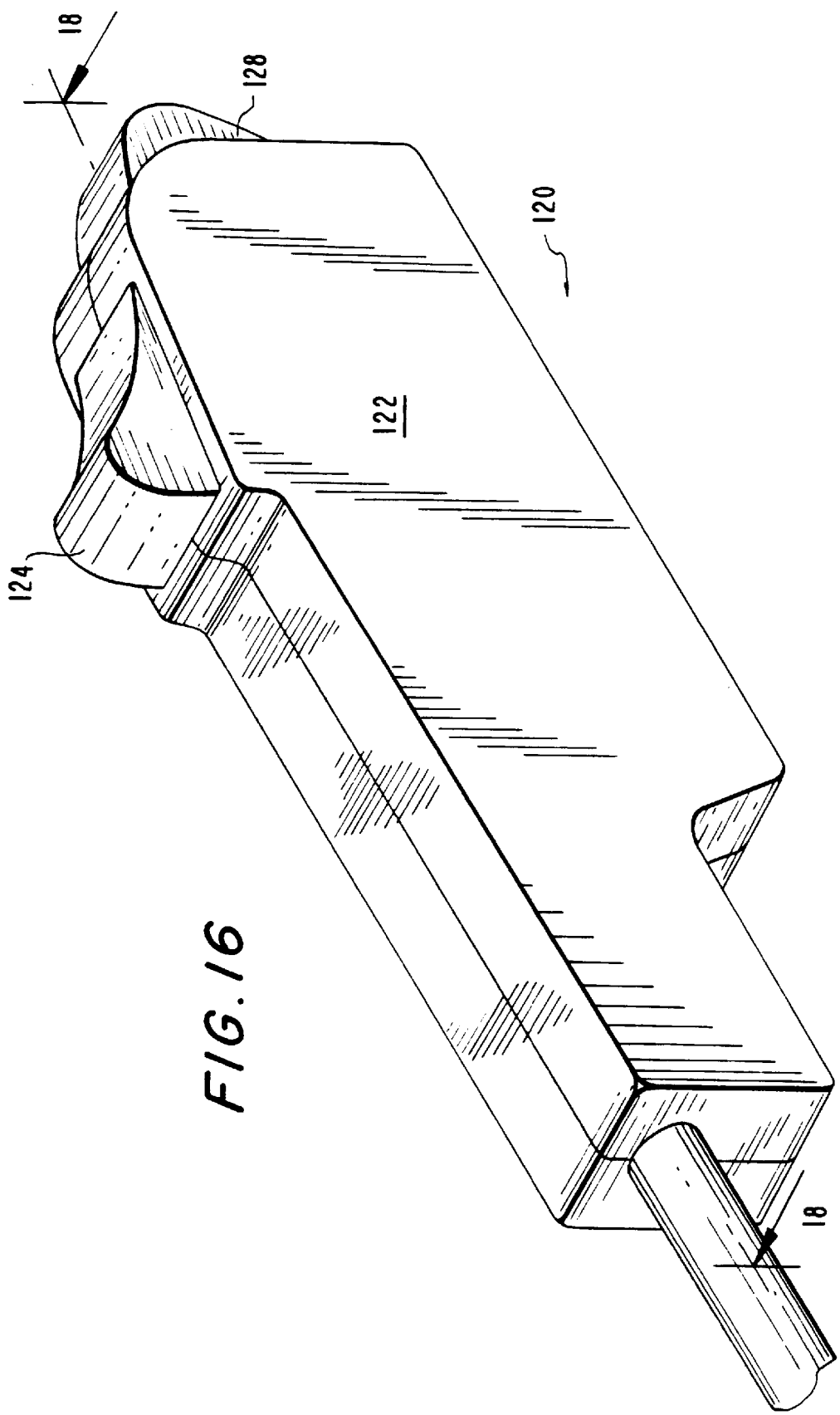
FIG. 16 is a perspective view of another embodiment of the handle and pneumatic system of the present invention.

Referring now to FIG. 16, there is illustrated in perspective view another alternative embodiment of the handle system of the present invention. In accordance with this embodiment, the staple prepositioning stroke or function is powered by the pneumatic system.

Figure 17:
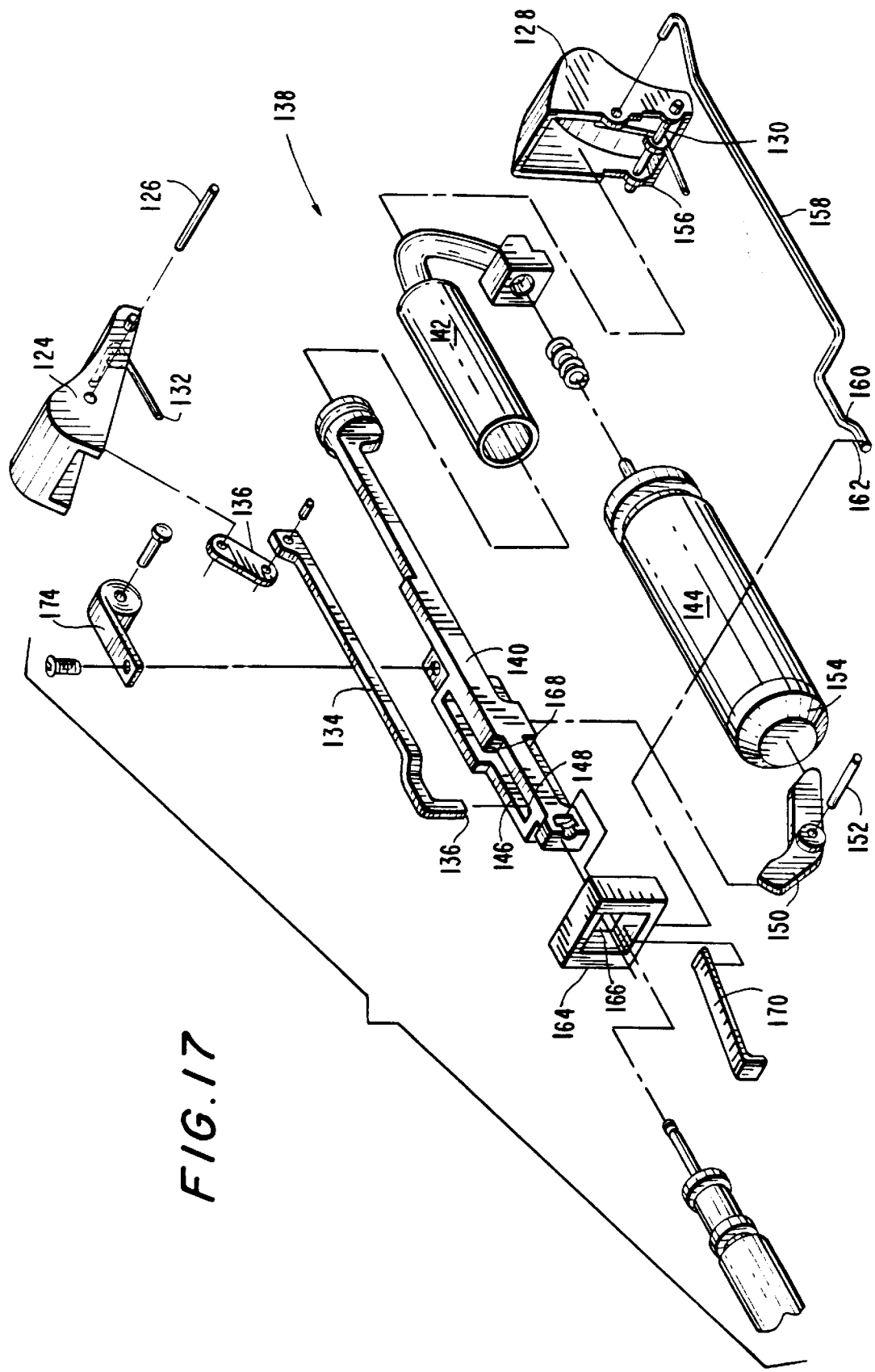
FIG. 17 is a perspective view with parts separated of the handle and pneumatic system of FIG. 16.
Figure 18:
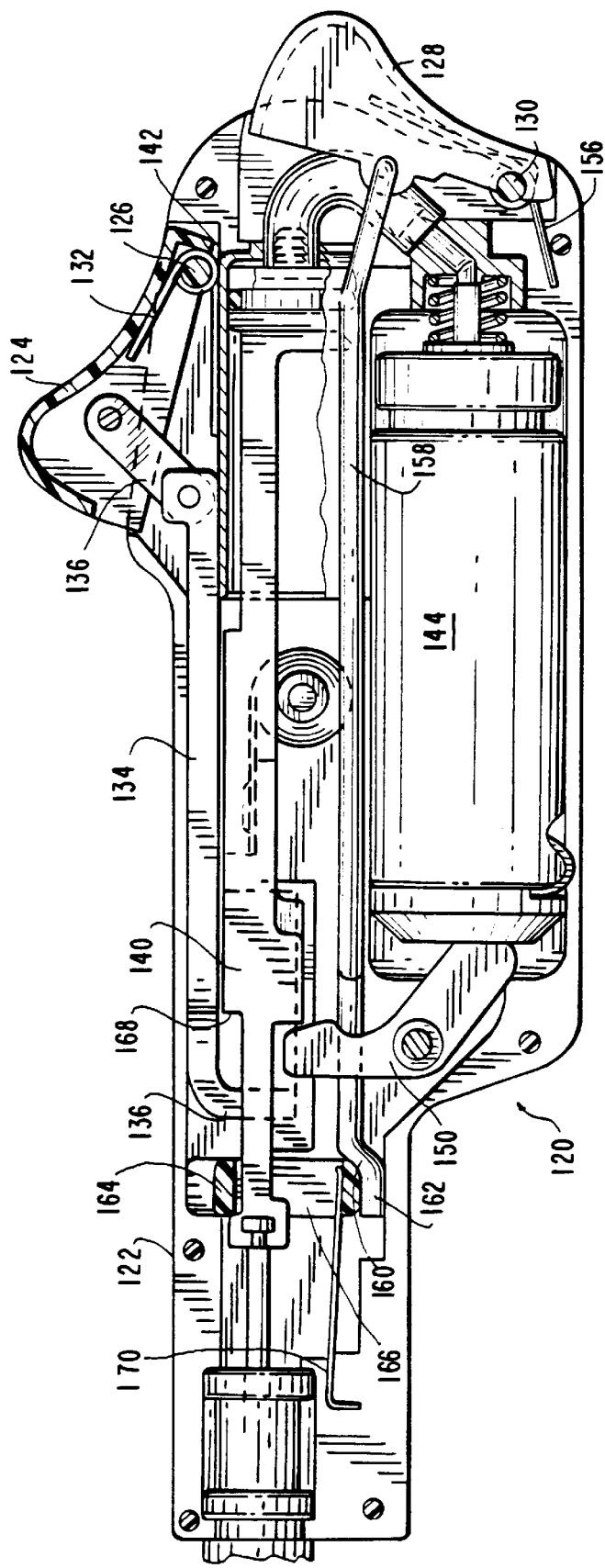
FIG. 18 is a cross-sectional view taken along the lines 18—18 of FIG. 16 illustrating the handle in the initial position.

Referring initially to FIGS. 16, 17 and 18, handle 120 includes frame 122 having firing button 124 pivotably mounted to the upper surface portion of the frame about pin 126 and release button 128 pivotally mounted about pin 130. As will be appreciated from the description below, firing button 124 initiates the power stroke provided by the pneumatic system and functions in positioning the staple in a slightly advanced position to facilitate attachment to the surgical mesh and subsequent placement of the staple in the body tissue. Release button 128 releases the pneumatic piston of the pneumatic system to permit full completion of the power stroke to fire the staple.

Firing button 124 is biased to its upward preactuated position by spring 132 which is wrapped about mounting pin 126. Firing button 124 is operatively connected to firing link 134 via intermediate link 136. Firing link 134 extends longitudinally within frame 122 and includes a downwardly extending projection 136 at its distal end which is operatively connected to the pneumatic system, identified generally as reference numeral 138, as will be described.

Pneumatic system 138 is substantially similar in structure and function to the pneumatic system described in connection with the two previous embodiments and includes piston 140 reciprocally movable in cylinder 142 in response to release of gas from container 144. Piston 140 includes a partial channel 146 formed in its upper surface to receive downwardly extending projection 136 of firing link 134 to connect the firing link with the pneumatic system. Partial channel 146 defines a forward bearing surface 148 which is engaged by downwardly projecting member 136 of firing link 134 during distal longitudinal movement of the firing link 134 to thereby cause corresponding longitudinal movement of piston 140 as shown in FIG. 19. Piston 140 is directly connected to pusher rod 26 at its distal end portion by conventional means.

Referring particularly to FIGS. 17 and 18, rocking lever 150 mounted about pin 152 operatively engages piston 140 at an upper end portion of the lever and engages pusher disk 154 affixed to container 144 at a lower portion of the lever. Rocking lever 150 pivots in response to longitudinal movement of piston 140.

Release button 128 is biased in the proximal direction by spring 156 and is operatively connected to release rod 158 which extends longitudinally within frame 122 beneath piston 140. Release rod 158 is adapted for reciprocal longitudinal movement in response to corresponding pivotal movement of release button 128. The distal end portion of release rod 158 includes a sloped portion 160 which defines a lower bearing surface portion 162 on which a rectangular piston stop 164 rests.

Figure 22:
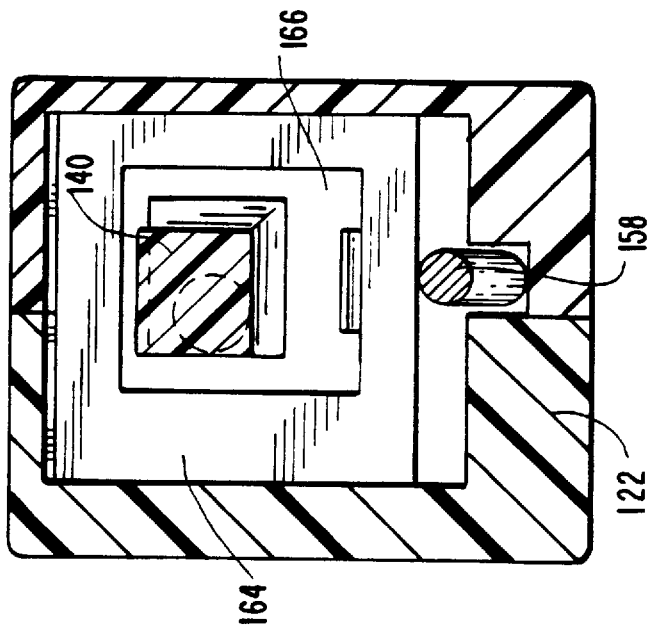
FIG. 22 is an enlarged cross-sectional view taken along lines 22—22 of FIG. 21 illustrating the piston in alignment with the piston stop to permit further advancing movement of the piston.
Figure 20:
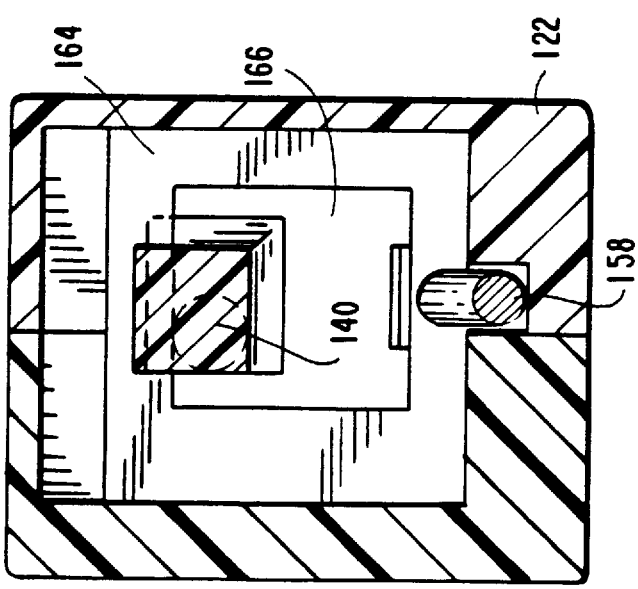
FIG. 20 is a cross-sectional view taken along the lines 20—20 of FIG. 19 illustrating the abutting relationship of the piston and piston stop prior to pivotal movement of the piston stop release button.
Figure 21:
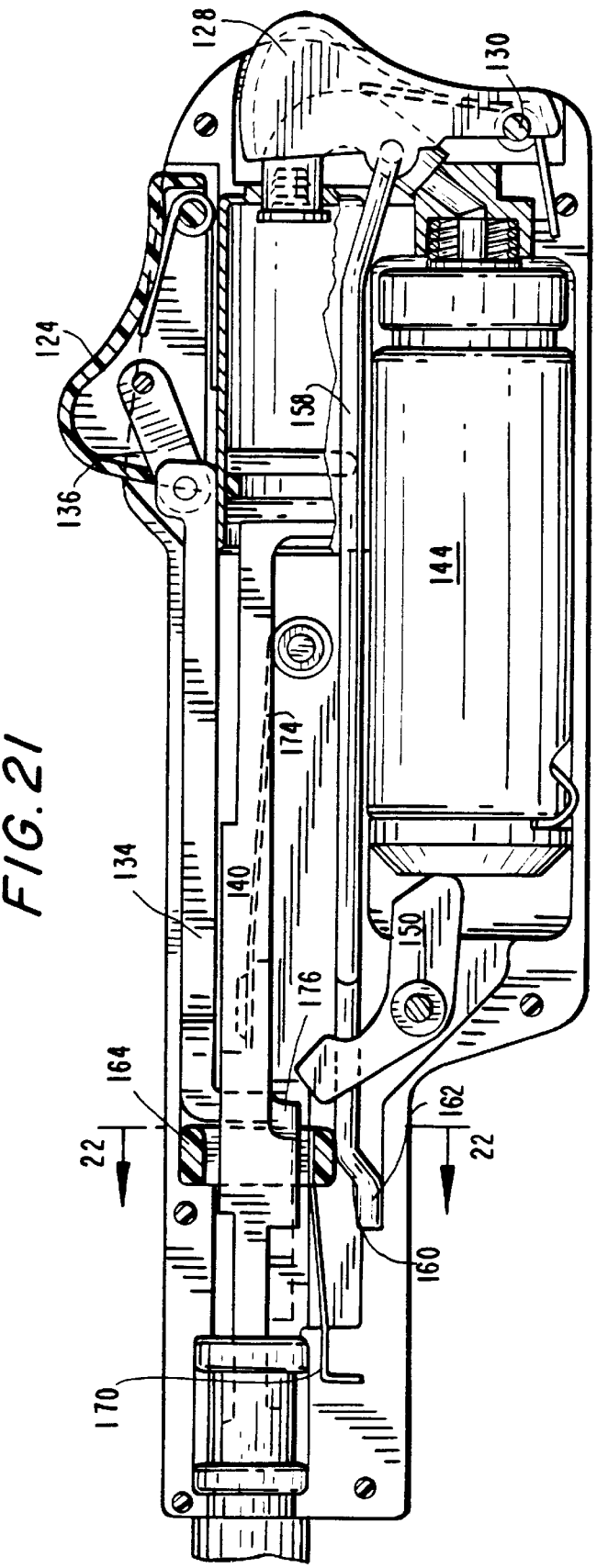
FIG. 21 is a cross-sectional view similar to FIG. 19 illustrating the stop release button in the depressed position corresponding to release of the piston to complete the firing of the staple.

Piston stop 164 defines a generally rectangular aperture 166 which receives the distal end portion of piston 140. Piston stop 164 is reciprocally vertically movable between a lower piston engaging position (FIGS. 19 and 20) and an upper piston non-engaging position (FIGS. 21 and 22). As shown in FIGS. 19 and 20, in the engaging position, piston 140 and aperture 166 of piston stop 164 are misaligned such that an upper transverse bearing surface 168 of the piston 140 engages an upper surface of piston stop 164. In the non-engaging position shown in FIGS. 21 and 22, piston 140 and aperture 166 of piston stop 164 are in general alignment to permit continual distal advancement of the piston. Piston stop 164 is normally biased in the lower engaging position by resilient lever 170.

In use, firing button 124 is depressed as shown in FIG. 19 which effects longitudinal distal movement of firing link 134. During longitudinal movement of firing link 134, projecting member 136 of the firing link engages forward bearing surface 148 defined by channel 146 in piston 140 to advance the piston. Advancing movement of piston 140 causes rotation of rocking lever 150 about pin 152, which causes proximal movement of container 144 and, accordingly, release of gases from the container. The released gases drive piston 140 in the distal direction. Piston 140 continues in the distal direction until outer bearing surface 168 of the piston engages piston stop 164 as shown. In this position of piston 140, the pusher rod 26 is advanced sufficiently to partially expose a staple from staple magazine 16 to thereby preposition the staple to facilitate staple placement in the surgical mesh and/or body tissue. In the embodiment of FIG. 16, the staple prepositioning feature is pneumatically actuated through movement of firing button 124 which causes the dispensing of pressurized gas and consequent movement of the pusher rod 26. Firing button 124 constitutes the "first means" or "first transmission" for distally advancing the pusher rod 26 from the initial position to the first predetermined position.

As piston 140 moves distally, rocking lever 150 remains in a pivoted engaged position with container 144 by contact with lower bearing surface 172 of the piston. Accordingly, this ensures movement of container 144 to its proximalmost position, thus ensuring sufficient release of gas from the container and sufficient gas build-up in the cylinder to complete the firing stroke. It is to be appreciated that the dimension of bearing surface 172 may be varied to control the amount of rotational movement of rocking lever 150, and, thus the amount of gases released by container 144. Once the piston 140 advances to a position where lower bearing surface 172 clears rocking lever 150, the release of gas from container 144 is stopped.

Referring now to FIG. 21, release button 128 is depressed which effectuates corresponding distal movement of release link 158. As release link 158 advances distally, piston stop 164 slides along sloped portion 160 of the release link to assume an elevated position as shown. In this position, aperture 166 of piston stop 164 is in alignment with piston 140 (See also FIG. 22) to permit continued distal movement of the piston and corresponding movement of pusher rod 26 to thereby fire a staple from staple magazine. As previously mentioned, the gas build-up in cylinder 142 is sufficient to drive piston 140 to fire a staple once the piston is disengaged from piston stop 164. In the embodiment of FIG. 16, staple pusher rod 26 moves to its second position through movement of release button 128 which causes piston 140 to be released from its engagement with piston stop 164 thereby permitting further distal movement of the pusher rod 26. The release button 128 constitutes the "second means" or "second transmission" for distally advancing the staple pusher to the second position to close the staple.

Referring again to FIG. 21, release of release button 128 upon completion of the power stroke effects return of piston 140 to its initial position under the influence of negator spring 174. During the return movement of piston 140, camming surface 176 formed in piston 140 causes the upper portion of rocking lever 150 to move transversely out of engagement with the piston to permit the piston to assume its initial position.

Figure 23:
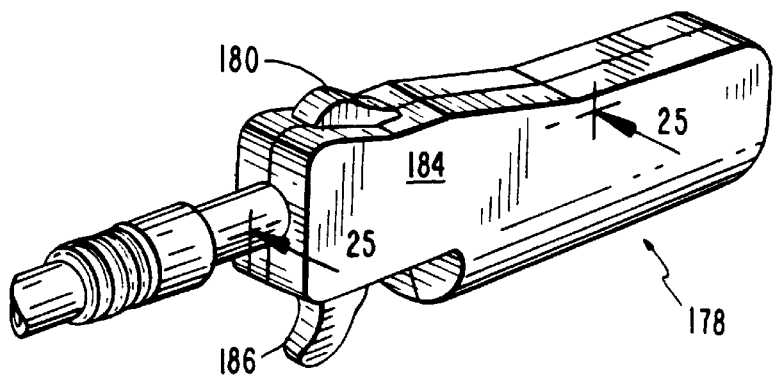
FIG. 23 is a perspective view of another alternative embodiment of the handle and pneumatic system of the present invention.
Figure 24:
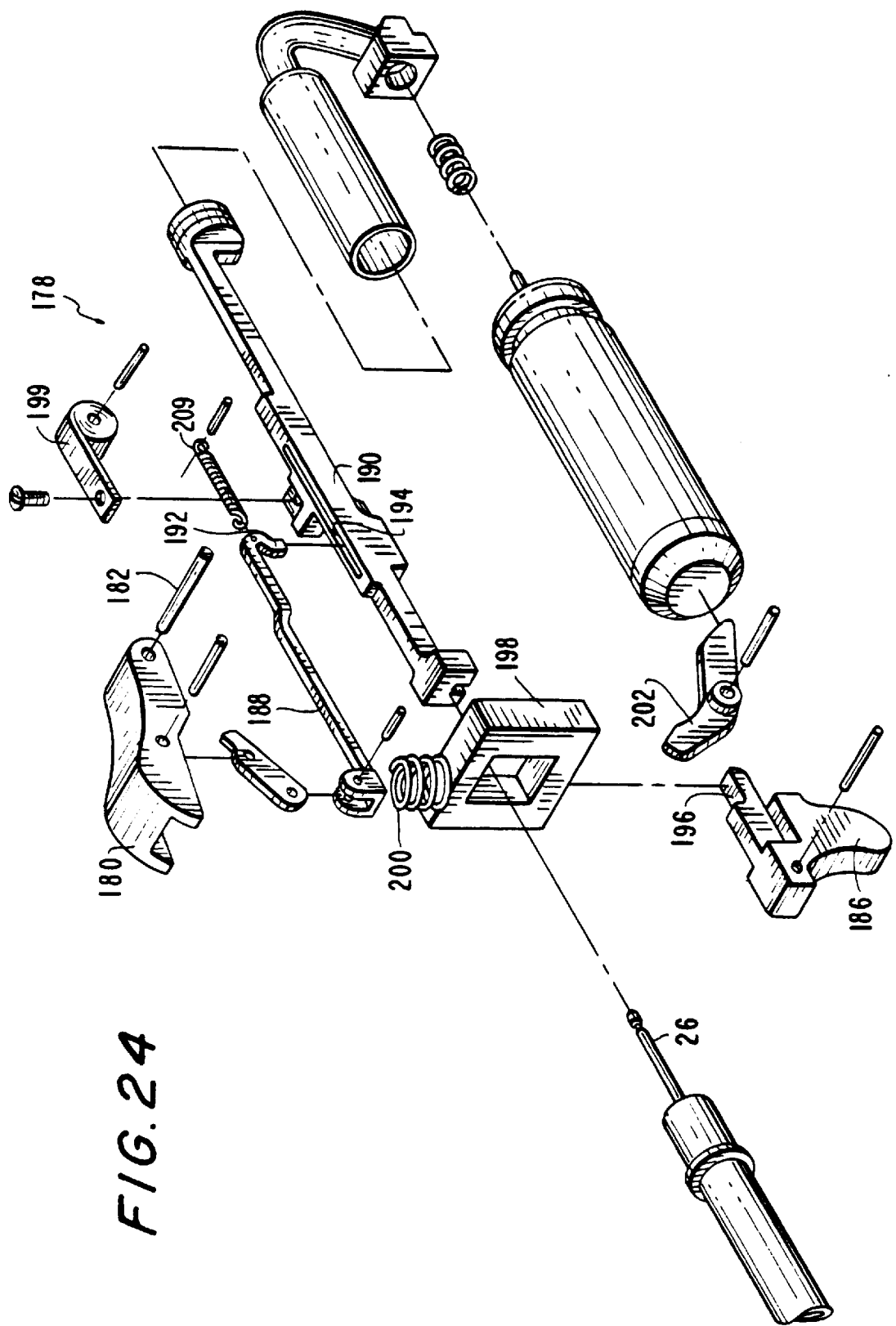
FIG. 24 is an exploded perspective view with parts separated of the handle and pneumatic system of FIG. 23.
Figure 25:
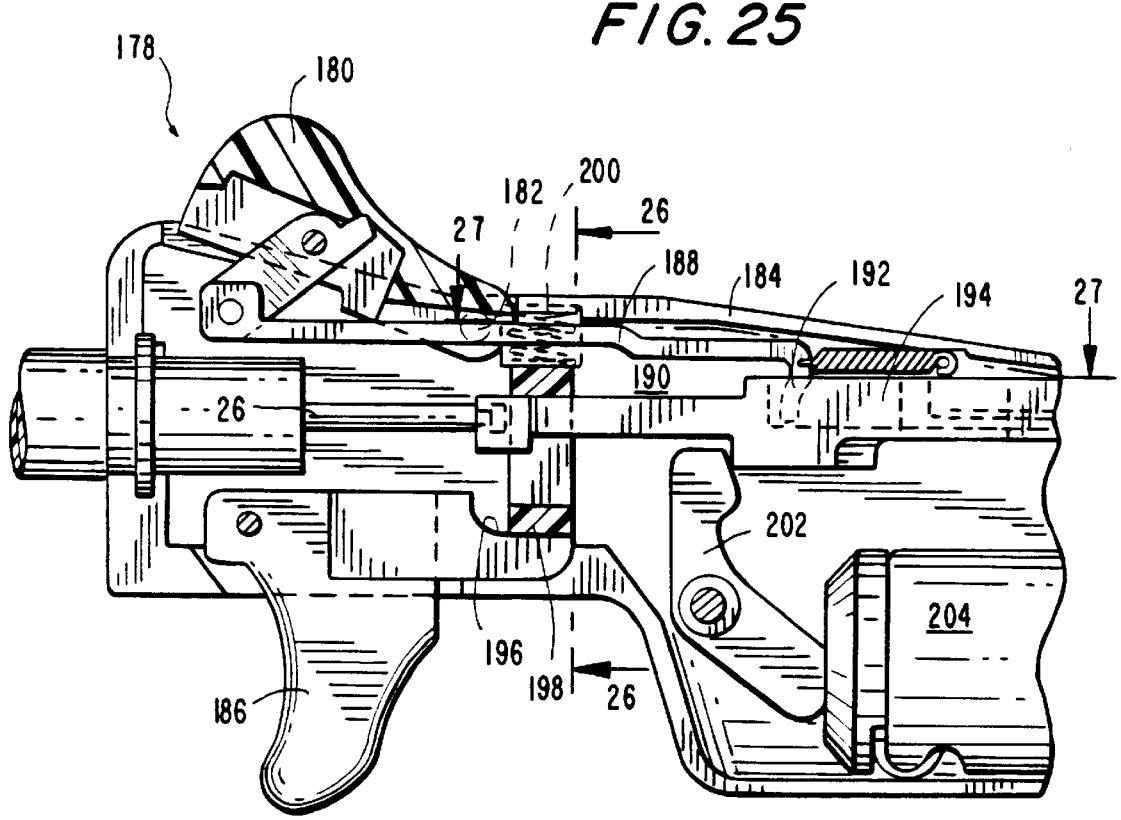
FIG. 25 is a cross-sectional view taken along lines 25—25 of FIG. 23 illustrating the handle of the apparatus in the initial condition.

Referring now to FIGS. 23, 24 and 25, there is illustrated another embodiment of the handle system of the present invention. Handle system 178 is similar in most respects to the embodiment of FIG. 16 and includes firing button 180 pivotally mounted about pin 182 in the forward portion of frame 184 and release trigger 186 pivotally mounted to the lower surface portion of the frame. Firing button 180 is operatively connected to firing link 188, which link 188 is operatively connected to piston 190 of the pneumatic system. In particular, downward extending projection 192 of firing link 188 is received within channel 194 formed in piston 190.

Figure 26:
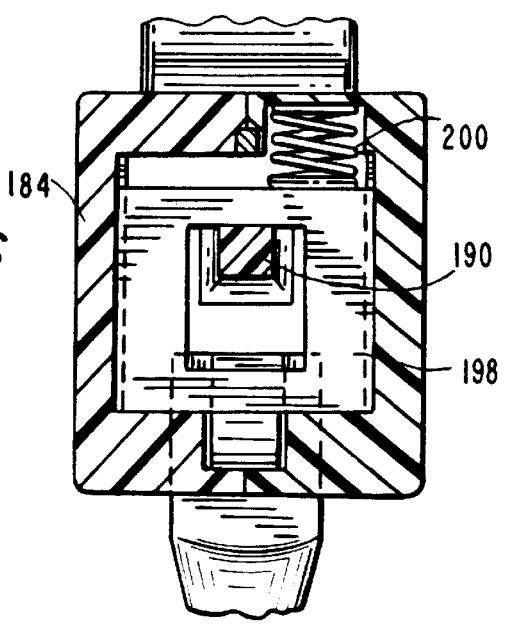
FIG. 26 is a cross-sectional view taken along lines 26—26 of FIG. 25 illustrating the piston of the pneumatic system received within the piston stop and the relative positioning of the piston stop prior to pivotal movement of the firing button.

Release trigger 186 includes a horizontal bearing surface 196 at its proximal portion on which piston stop 198 rests. Piston stop 198 is adapted for transverse movement between a downward piston engaging position (FIGS. 28 and 29) and an upward piston disengaged position (FIGS. 30 and 31) in response to pivotal movement of release trigger 186. Piston stop 198 is normally biased to the downward piston engaging position by coil spring 200 which is in engaging contact with the upper surface of the piston stop 198 as shown in FIG. 26.

Figure 28:
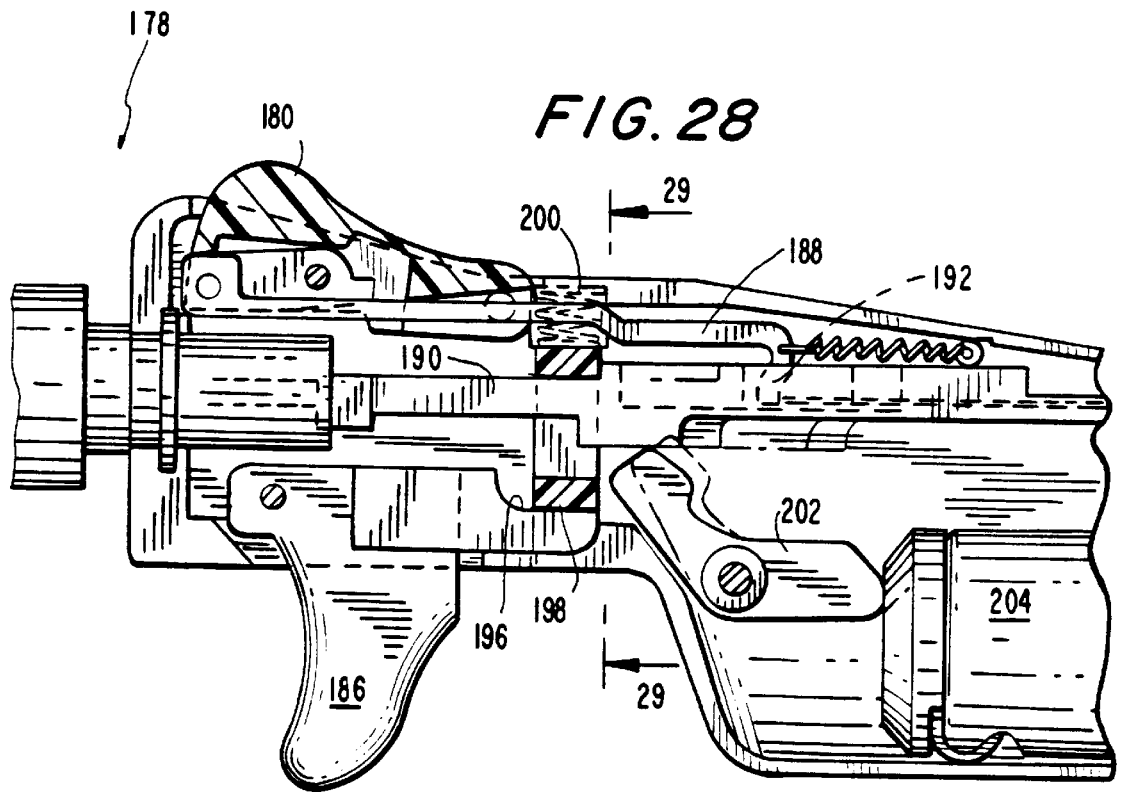
FIG. 28 is a cross-sectional view similar to FIG. 25 illustrating the staple firing button in an advanced depressed position corresponding to firing of the staple.
Figure 29:
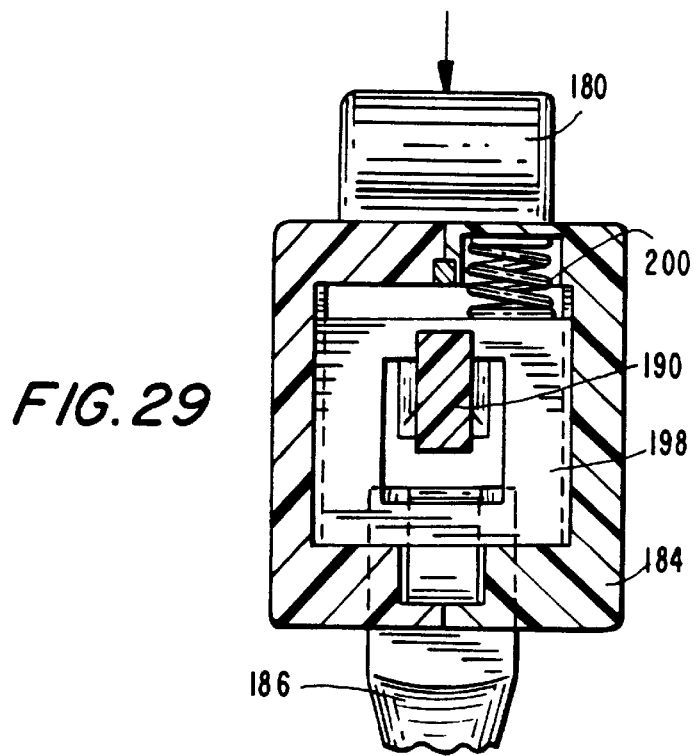
FIG. 29 is a cross-sectional view taken along lines 29—29 of FIG. 28 illustrating the abutting relationship of the piston and piston stop prior to pivotal movement of the stop release trigger.
Figure 30:
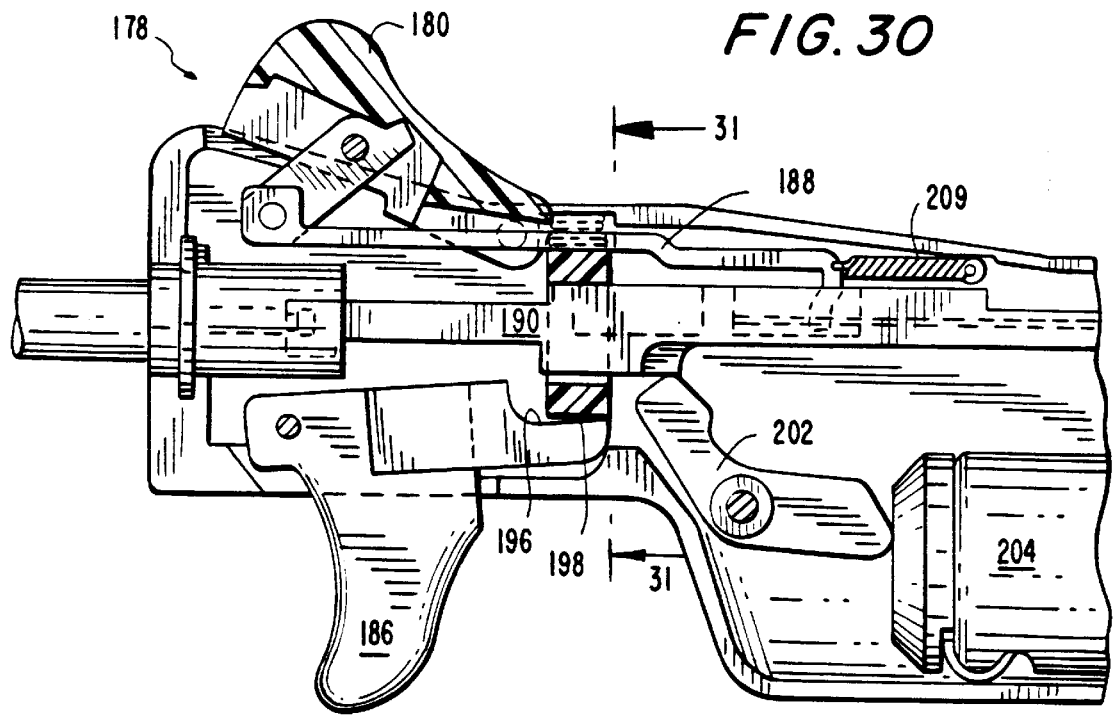
FIG. 30 is a cross-sectional view similar to FIG. 28 illustrating the stop release trigger in a pivoted proximal position corresponding to release of the piston from the piston stop to complete firing of the staple.
Figure 31:
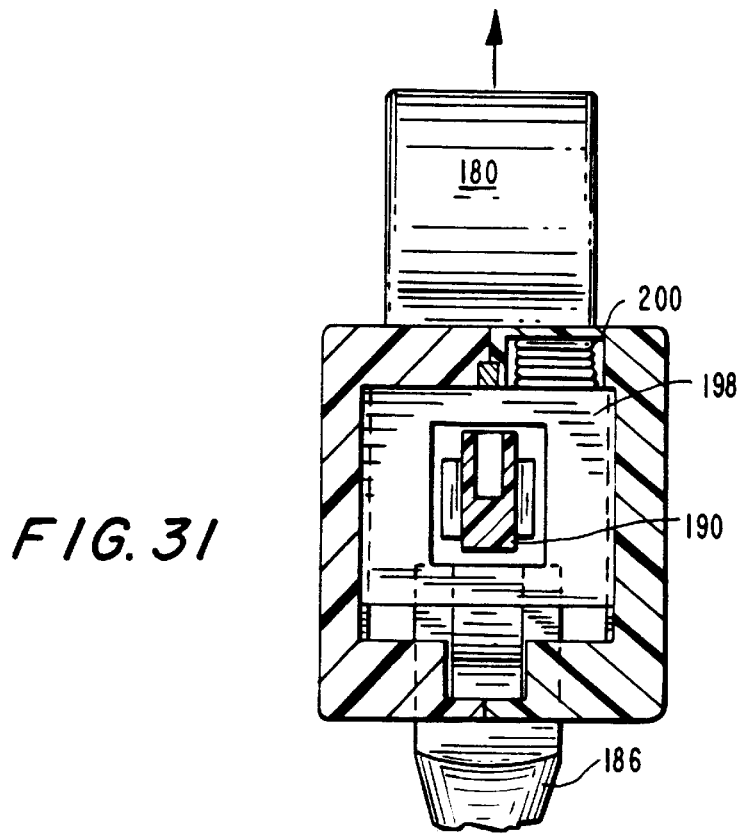
FIG. 31 is an enlarged cross-sectional view taken along lines 31—31 of FIG. 30 illustrating the piston in alignment with the piston stop to permit advancing movement of the piston.

In use, depression of firing button 180 causes advancing movement of firing link 188 and piston 190 and rotation of rocking lever 202 to thereby effect release of gases from container 204 to drive piston 190 to the advanced position shown in FIG. 28 in engagement with piston stop 198. In this position, a staple is slightly advanced from cartridge 16 to pre-position the staple for subsequent placement to the surgical mesh and/or body tissue. In the embodiment of FIG. 23, the staple prepositioning feature is pneumatically actuated through movement of firing button 180 which causes the dispensing of pressurized gas and consequent movement of the pusher rod 26. Firing button 180 constitutes the "first means" or "first transmission" for distally advancing the pusher rod 26 from the initial position to the first predetermined position. Thereafter, trigger 186 is squeezed to elevate piston stop 198 and align the aperture of the piston stop with piston 190 as shown in FIGS. 30 and 31. Accordingly, piston 190 is released from its engagement with the piston stop 198 so as to be driven by the gaseous build up in the cylinder to complete the power stroke and fire the staple. It is to be appreciated that in the alternative, the apparatus may be adapted such that further advancing movement of piston 190 after release of piston stop 198 may cause further rotational movement of rocking lever 202 and release of additional gases from the gas container to assist in driving the piston. In the embodiment of FIG. 23, staple pusher rod 26 moves to its second position through movement of release trigger 186 which causes piston 190 to be released from its engagement with piston stop 198 thereby permitting further distal movement of the pusher rod 26. The release trigger 186 constitutes the "second means" or "second transmission" for distally advancing the staple pusher to the second position to close the staple.

Figure 27:
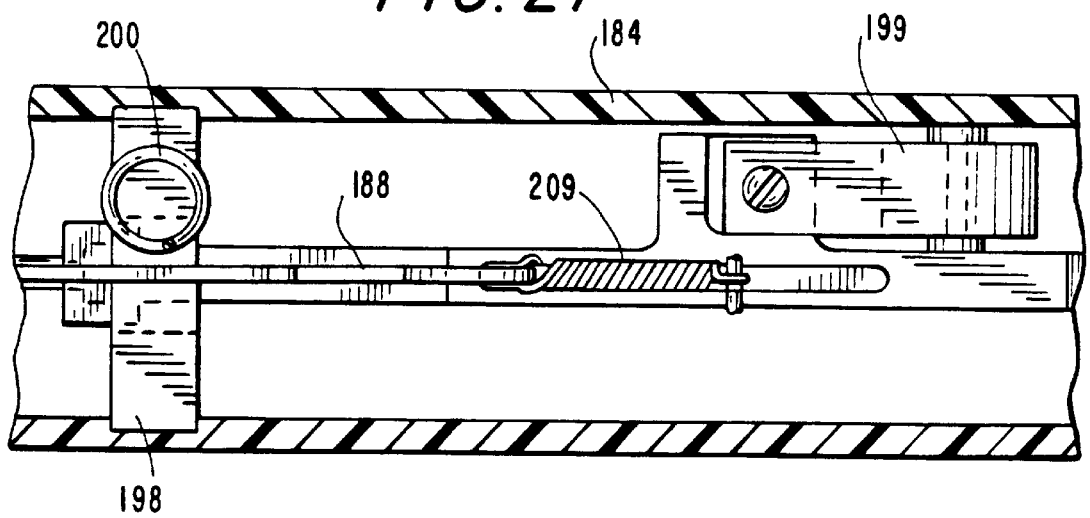
FIG. 27 is a cross-sectional view taken along lines 27—27 of FIG. 25 illustrating the firing link operatively connected to the piston of the pneumatic system.

Upon completion of the power stroke, firing link 188 is returned to its initial unadvanced position by coil spring 209 which is affixed to the proximal end of the link. Similarly, piston 190 is returned to its initial position by negator spring 199 (FIG. 27) and piston stop 198 is returned to its downward piston engaging position by coil spring 200.

Figure 32:
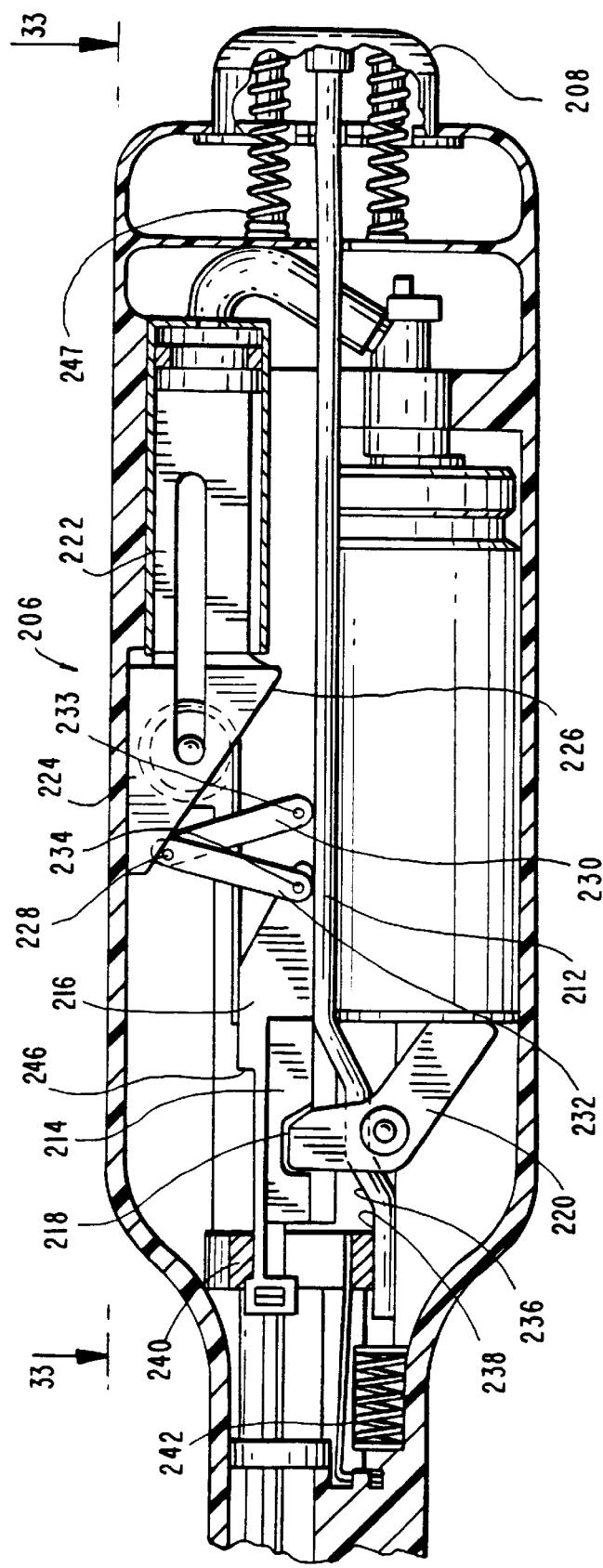
FIG. 32 is a cross-sectional view of another alternative embodiment of the handle of the present invention illustrating the initial unadvanced position of the apparatus.
Figure 33:
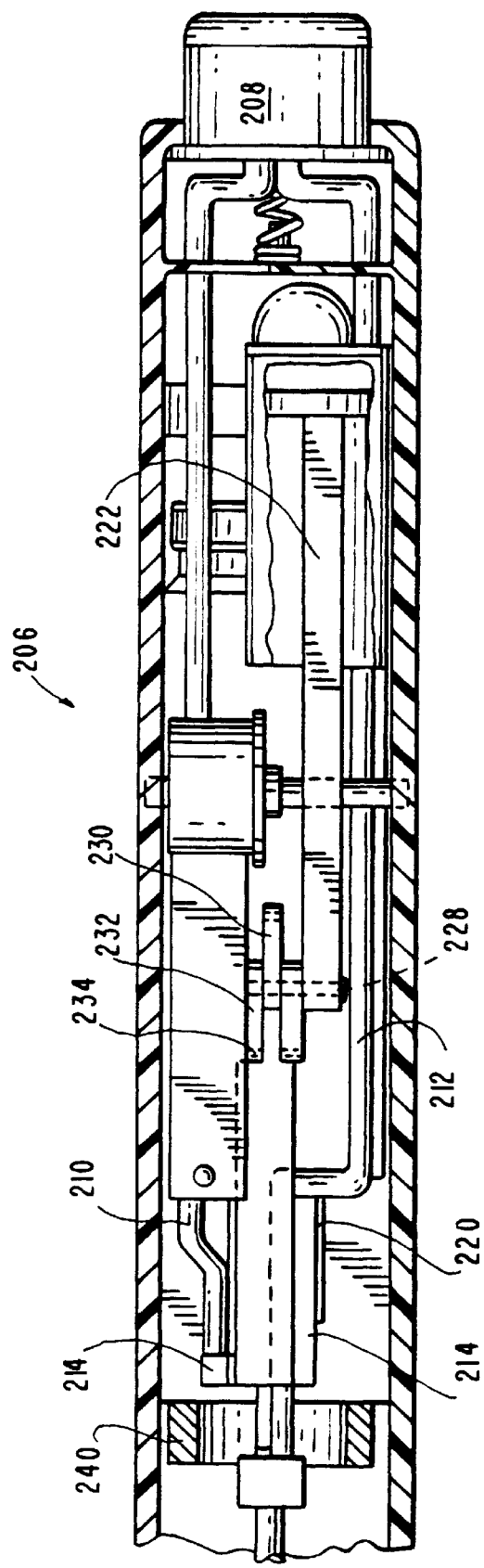
FIG. 33 is a cross-sectional view taken along the lines 33—33 of FIG. 32 illustrating the mechanisms for advancing and closing the staples.

Referring now to FIGS. 32 and 33, there is illustrated another alternative embodiment of the handle system of the present invention. Handle system 206 is similar to the handle system described in connection with the embodiments of FIGS. 16 and 23 except that the current handle 206 is provided with a single actuating button 208 to perform both the staple prepositioning function, i.e., to actuate the pneumatic system to initially advance the staple, and the release function, i.e., to release the pneumatic piston to permit full completion of the power stroke to fire the staple.

Actuating button 208 of handle 206 is operatively connected to two link members namely, firing link 210 and release link 212, which extend longitudinally within the handle section. The firing link 210 is operatively connected at its forward end portion to a reciprocating slide 214 which is mounted for reciprocal movement on a lower surface portion of an actuating rod 216 and moves independently relative to the rod. Reciprocating slide 214 moves in a distal direction in response to distal movement of firing link 210, which link 210 moves distally by initial depression of actuating button 208. A recess 218 is formed in reciprocating slide 214 and is dimensioned to receive the forward end portion of rocking lever 220.

Piston 222 of the pneumatic system includes a forward camming portion 224 defining camming surface 226. Camming surface 226 contacts pin 228 which connects rear and forward link members 230, 232 respectively. A portion of camming pin 228 extends beyond one of the front link members 232 in position to be engaged by camming surface 226. Rear link 230 is mounted at its lower portion to the frame of handle 206 by stationary mounting pin 233. Front link 232 is operatively connected to actuating rod 216 via connecting pin 234. As will be appreciated from the description provided below, distal movement of piston 222 advances actuating rod 216 in the distal direction due to coordinating movement of front and rear links 230, 232.

Release link 212 includes a sloped portion 236 at its distal end which defines a lower bearing surface portion 238 on which rectangular piston stop 240 rests.

Handle 206 also includes a coiled spring 242 disposed adjacent the distal bearing surface 244 of release link 212. As will be appreciated from the description provided hereinbelow, spring 242 provides a tactile feel to the user that the prepositioning stage of the stapler has been obtained.

Figure 34:
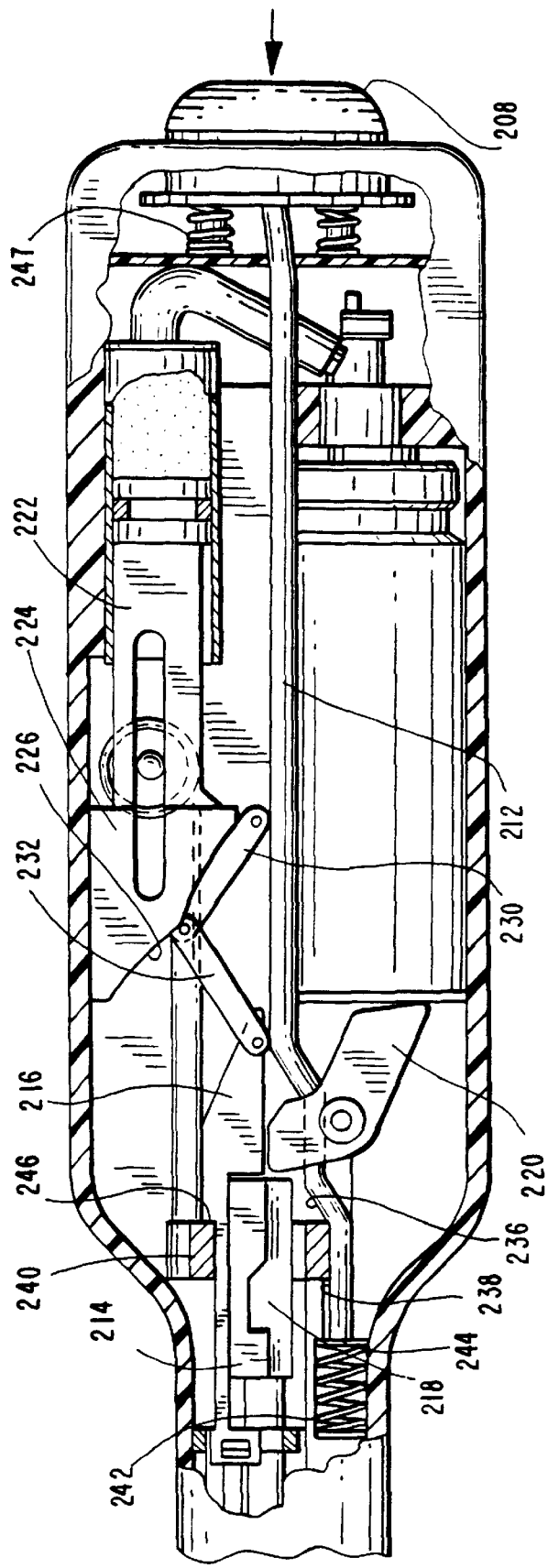
FIG. 34 is a cross-sectional view similar to FIG. 32 illustrating the actuating button in a first depressed position corresponding to the partially advanced position of the staple.

In use, actuating button 208 is depressed a first distance as shown in FIG. 34 which effects longitudinal distal movement of both firing link 210 and release link 212. Focusing initially on firing link 210, longitudinal movement of the firing link causes reciprocating slide 214 to move distally due to its interconnection with the firing link. Distal movement of reciprocating slide 214 effects rotation of rocking lever 220, due to the engagement of the rocking lever with recess 218 of the slide, which thereby releases gas from the container in the same manner described in connection with the embodiments of FIGS. 16 and 23. FIG. 34 shows the condition of handle 206 upon completion of the first or prepositioning stage. In the embodiment of FIG. 32, the staple is prepositioned pneumatically by movement of actuating button 208 which releases the pneumatic gases of the pneumatic system to drive the pusher rod 26 distally to its first position. The firing link 210 which is moved by the actuating button 208 to activate the pneumatic system constitutes "first means" or "first transmission" for distally advancing the pusher 26 to the first predetermined position to preposition the staple. As shown in FIG. 34, after release of slide 214 with rocking lever 220, slide 214 returns to an initial proximal position relative to actuating rod 216. Such return of slide 214 is effected by a return spring (not shown) disposed within the body of the slide 214.

It is to be appreciated that during initial movement of reciprocating slide 214 actuating rod 216 remains stationary. The released gases drive piston 222 in the distal direction which causes camming surface 226 of camming portion 224 to engage camming pin 228 and force the pin 228 to move along the camming surface 226. As camming pin 228 moves along camming surface 226, the front link members 232 move distally, which drives actuating rod 216 distally where bearing surface 246 (FIG. 32) of the actuating rod engages actuating stop 240 as shown in FIG. 34. Such advanced position of piston 222 and actuating rod 216 corresponds to the prepositioned stage of the apparatus where the staple is slightly advanced for positioning adjacent the body tissue.

During the initial depression of actuating button 208, release link 212 also advances as previously mentioned. In particular, release link 212 moves distally until distal bearing surface 244 of the release link 212 engages coiled spring 242. It is to be noted that in this position of release link 212, firing link 210 has been advanced to the position where it actuates the pneumatic system to preposition the staple. Upon engagement with spring 242, the surgeon is tactilely made aware that the prepositioning stage of the apparatus has been achieved due to the restraining force provided by spring on release link 212.

Figure 35:
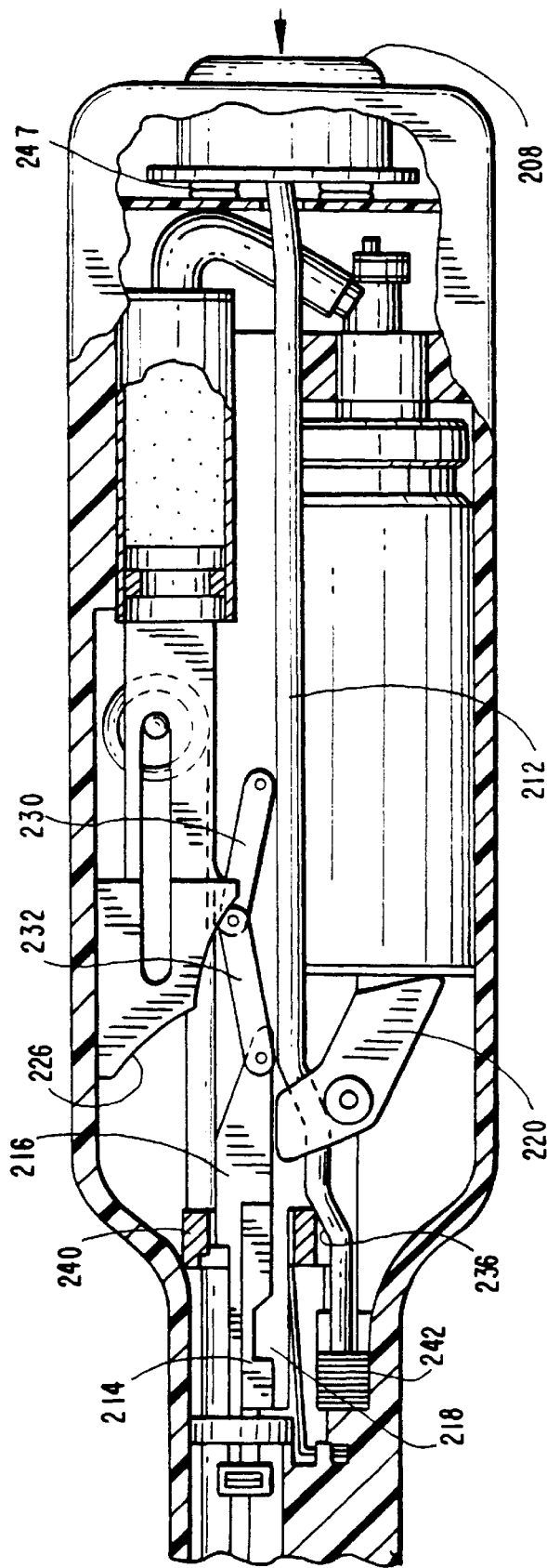
FIG. 35 is a cross-sectional view similar to FIG. 34 illustrating the actuating button in a second depressed position corresponding to firing of the staple.

To complete the firing of the staple, the surgeon further depresses button 208 against the resisting force provided by coil spring 242 to the position shown in FIG. 35, which causes release link 212 to further advance distally. The distal movement of release link 212 is resisted by coil spring 242 which indicates to the surgeon that firing of the staple is imminent. As release link 212 advances, actuating stop 240 slides along sloped portion 236 of the release link 212 to assume the elevated position shown in the Figure. In this position, the aperture of actuating stop 240 is in alignment with actuating rod 216 to permit continued movement of the actuating rod 216 and the pusher rod to complete the firing of the staple in a similar manner described in connection with the embodiments of FIGS. 16 and 23. After the firing cycle is completed, actuating button 208 is returned to its initial proximalmost position by return spring 247. In the embodiment of FIG. 32, the firing stroke is completed through continued movement of the actuating button 208 which causes release of the actuating rod 216 with actuating stop 240 to permit distal movement of the piston rod 26. The actuating rod 216 which is moved by the actuating button constitutes the "second means" or "second transmission" for distally advancing the staple pusher to the second position to close the staple.

Figure 36:
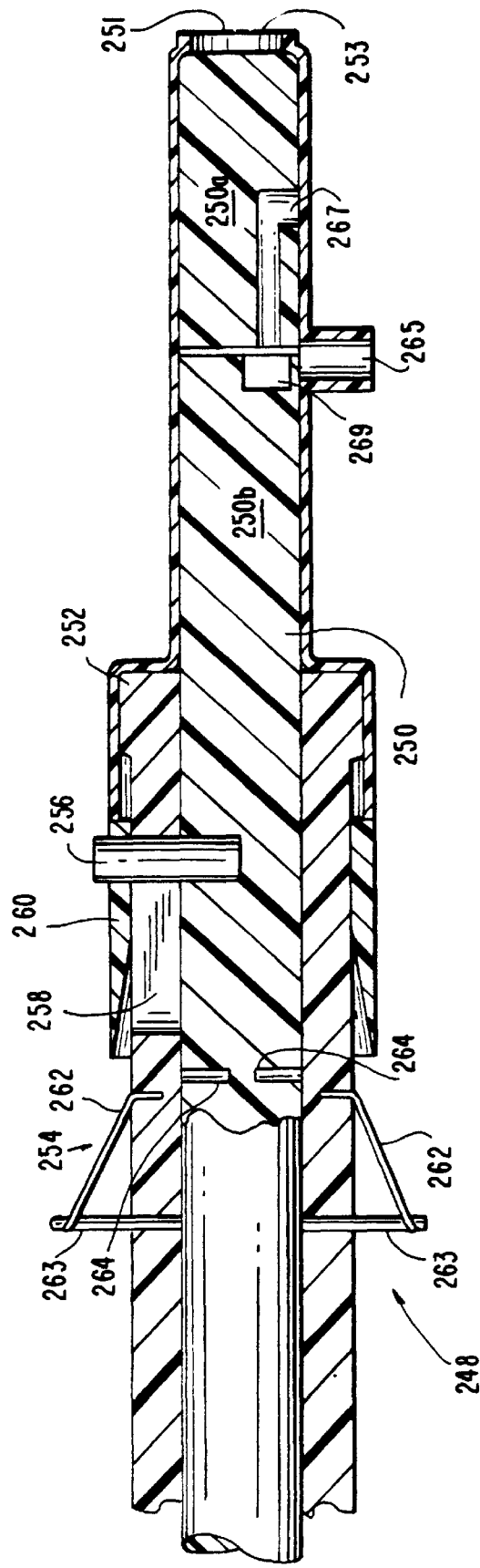
FIG. 36 is a cross-sectional view of an alternative two-part pneumatic piston which may be incorporated with the handle systems of FIGS. 3, 8, 16, 23 and 32, illustrating the piston in an initial unadvanced position.

Referring now to FIG. 36, there is illustrated in cross-section an alternative embodiment of a pneumatic piston which may be readily incorporated in the pneumatic systems of the prior handle systems of FIGS. 3, 8, 16 and 23. Piston 248 includes an inner rod 250 concentrically received within a bore defined in outer tubular member 252 as shown. Inner rod 250 includes two separate sections, namely, proximal section 250a and distal section 250b. During the prepositioning stage of the instrument, gas is released into inlet 251 and directed against surface 253 of proximal section 250a, which drives the proximal and distal sections of inner rod 250 distally to the position shown in FIG. 37. During such distal movement of inner rod 250, outer tubular member 252 remains stationary. This position of inner rod 250 corresponds to the prepositioning stage of the apparatus where the staple is slightly advanced and exposed from the staple cartridge. Also, in such position of inner rod 250, the distal section 250b of inner rod 250 becomes engagingly connected to outer tubular member 252 via an engaging mechanism identified generally as reference numeral 254.

Figure 37:
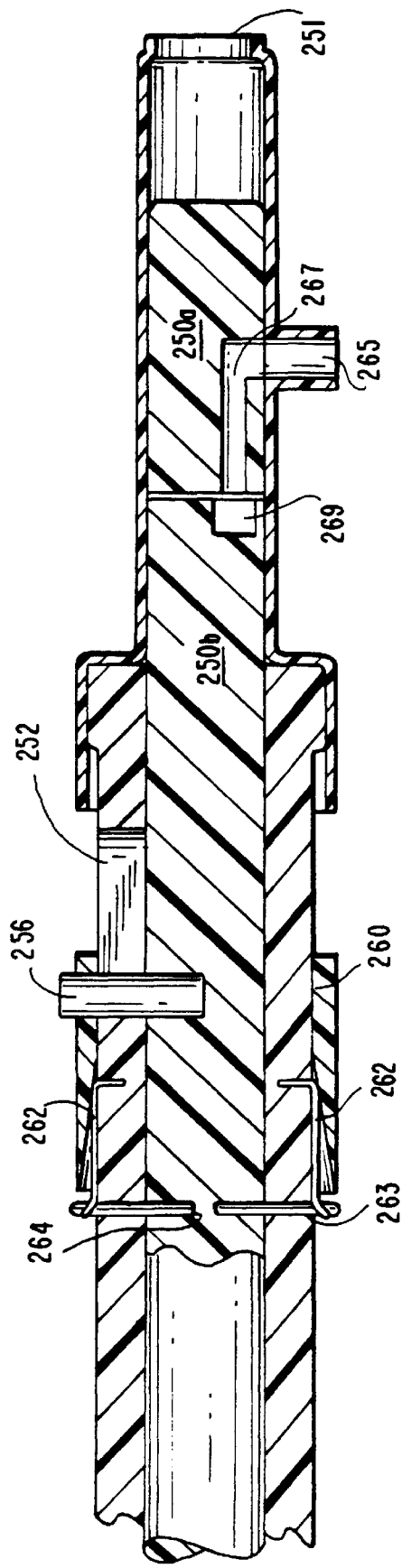
FIG. 37 is a cross-sectional view of the pneumatic piston of FIG. 36, illustrating the piston in a first advanced position corresponding to at least partially advancing the staple.
Figure 42:
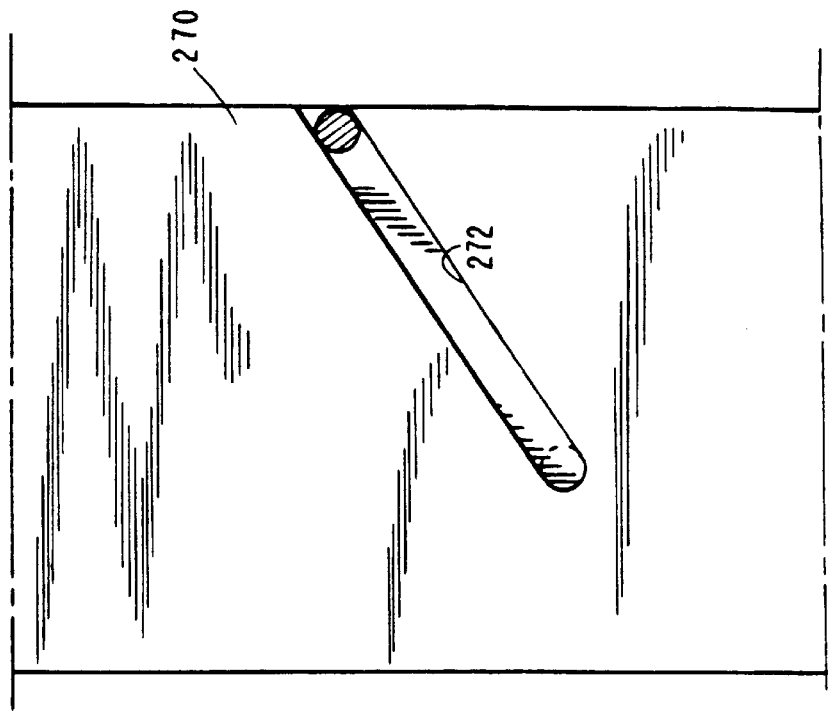
FIG. 42 is a view of the interior surface of the inner sleeve of the manually operable collar of FIGS. 38–41, projected as a flat surface to illustrate the helical groove provided for coaction with a pin to provide pivotal motion for the staple magazine at the distal end.

Referring again to FIG. 36, in conjunction with FIG. 37, engaging mechanism 254 includes transverse member 256 which is securely mounted at one end portion to distal section 250b of inner rod 250. The second end portion of transverse member 256 is received within a groove 258 formed in tubular member 252 where it is connected by conventional means to a hollow cylindrical sleeve 260 disposed about the outer tubular member 252. Also provided as part of the engaging mechanism is a pair of outwardly biased opposed springs 262 connected to outer tubular member 252 as shown. Springs 262 each have a transverse connecting member 263 which is received within a correspondingly dimensioned slot 264 formed in the distal section 250b to connect the outer tubular member to the distal section of the inner rod. In particular, during the prepositioning stage of the apparatus, cylindrical sleeve 260 advances with inner rod 250 and engages springs 262 to collapse the springs. The transverse connecting member 263 aligns with the correspondingly dimensioned slots 264 formed in distal section 250b and are received therewithin as shown in FIG. 37 to connect the distal section 250b of inner rod 250 with outer tubular member 252.

A significant advantage of having inner rod 250 move independently from outer tubular member 252 during the prepositioning stage of the apparatus is to reduce the gas requirements during this stage. In particular, minimal force is required to move the pusher rod to initially advance the staple during the prepositioning stage. Therefore, in an effort to conserve the amount of gas released by the gas container, only the inner rod 250 is required to advance so as to longitudinally move the pusher rod. The inner rod provides sufficient mass to move the pusher rod to initially preposition the staple. However, increased mass is required to create the forces sufficient to close the staple about the anvil. Therefore, in accordance with this embodiment, the inner rod 250 is connected to the outer tubular member 252 after the prepositioning stage of the apparatus to satisfy the mass requirements to close the staple.

Referring again to FIG. 37, once the piston 248 is advanced to the position corresponding to the prepositioned stage of the apparatus and the locking mechanism 254 is engaged to connect the distal portion 250b of the inner rod 250 with the outer tubular member 252, a second gaseous release is directed into inlet 265 and through channel 267 formed in proximal section 250a of rod 250. Channel 267 directs the gases into an inlet opening 269 and against a bearing surface (not shown) of distal section 250b, which drives the distal section 250b and connected outer tubular member 252 distally to advance the pusher rod to close the staple.

It is envisioned that one skilled in the art could readily modify the pneumatic systems and linkage mechanisms disclosed in the prior embodiments to operative with piston 248. For example, it is possible to incorporate a valve mechanism to control the direction of the gas flow from the gas container between the inlet opening 251 and the inlet opening 265. Further, the piston 248 may be interconnected to the rocking lever in a manner readily determined by one skilled in the art to cause the first and second gaseous releases from the pneumatic container.

The Staple Storage Magazine Pivoting System

Referring to FIGS. 38–44, the system for pivoting the staple storage magazine located at the distal end of the endoscopic section 14 will now be described. FIG. 38 illustrates double knurled finger operable collar 24 which is mounted for rotation with the endoscopic section 14 by inwardly extending pin 266 which is slidably positioned within longitudinal groove 268 in the outer housing half section 14a of endoscopic section 14, as shown in further detail in FIG. 38. Thus, collar 24 is readily slidable distally and proximally while pin 266 slides within groove 268. Thus while permitting slidable movement of collar 24, pin 266 prevents independent rotation of collar 24 relative to the endoscopic section 14. Accordingly, when collar 24 is gripped between the user's fingers and rotated, the endoscopic section 14 rotates with the collar.

Figure 41:
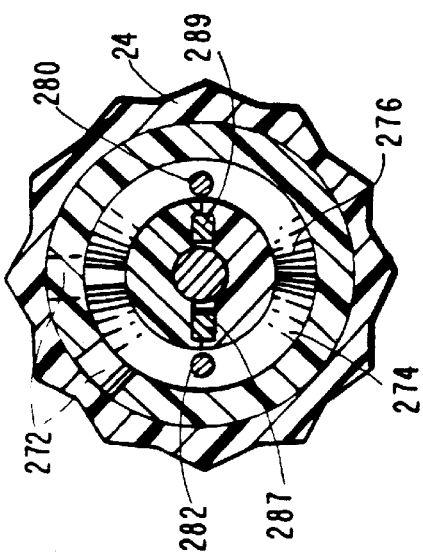
FIG. 41 is a cross-sectional view taken along lines 41—41 of FIG. 39 illustrating further details of the system for providing pivotal motion to the staple magazine at the distal end.
Figure 43:
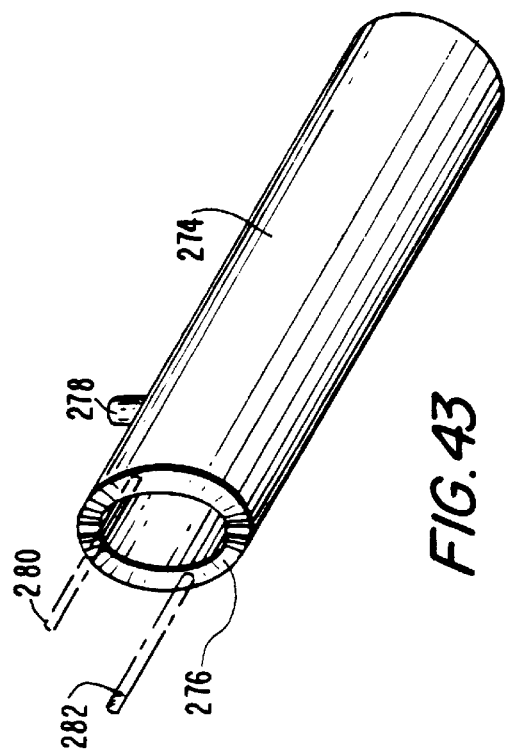
FIG. 43 is a perspective view of an internal sleeve and pin which coacts with the inner sleeve shown in FIGS. 41 and 42 which forms part of the system for pivoting the staple magazine at the distal end.

Positioned within finger operable collar 24 is helically grooved inner sleeve 270 fabricated of a suitable plastic material such as nylon, glass filled for strength. Helically grooved inner sleeve 270 is generally cylindrical in shape and includes a helical groove 272 shown in phantom lines in FIG. 38 and illustrated schematically in the projected frontal view of the sleeve shown in FIG. 42. The sleeve 270 is fixedly attached to outer collar 24 for rotation therewith. In the projected view of FIG. 42, the helical groove appears as a diagonal groove having a linear shape. In FIG. 41, finger operable collar 24 is shown in cross-section and the inner helically grooved sleeve 270 is shown whereby helical groove 272 is represented at two locations as viewed in FIG. 41. In FIG. 41, the cross-section of groove 272 at the 10 o'clock position (where lines 41–41 are located in FIG. 39) is just distal of the cross-section of groove 272 shown in phantom at the 12 o'clock position.

Referring now to FIG. 38 in conjunction with FIGS. 39–43, elongated internal cylindrical sleeve 274 is positioned partially within inner helically grooved sleeve 270 and collar 24 when collar 24 is in the distalmost position, as shown in FIG. 38; however, when collar 24 is withdrawn to the proximalmost position as shown in phantom lines in FIG. 38, the major portion of internal cylindrical sleeve 274 is positioned within collar 24 as shown. Internal sleeve 274 is preferably of nylon (preferably glass filled for strength) and defines a distal face 276 which is generally oriented at an acute angle with respect to the longitudinal axis of the instrument as shown clearly in FIGS. 38 and 43. The sleeve 274 contains pin 278 extending radially outwardly from the outer surface as shown. Pin 278 is preferably of steel or it may be formed of nylon integral with sleeve 274. Pin 278 is positioned for slidable movement within the helical groove 272 of inner sleeve 270 of collar 24 such that proximal movement of collar 24 will cause pin 278 to follow the groove 272 causing sleeve 274 to rotate in one direction. Similarly, distal movement of collar 24 to the position shown in phantom lines in FIG. 38 will cause pin 278 to traverse groove 272 in the opposite direction thereby causing sleeve 274 to rotate in the opposite direction.

The significance of the rotational motion of sleeve 274 as it pertains to the pivotal motion of staple storing magazine 16 will be described in further detail hereinbelow. At this stage, however, it is sufficient to state that the obliquely oriented distal face 276 of sleeve 274 engages the proximal ends of a pair of longitudinally extending push rods 280, 282 shown in phantom lines in FIG. 43 and more clearly in FIG. 44 such that when collar 24 is moved distally or proximally, inner sleeve 274 also rotates and the rods 280, 282 respectively move in equal and opposite directions by the engagement with different portions of oblique distal face 276 with these rods. In essence, one rod is engaged by a surface portion distal of the surface portion on the side of face 276 which engages the other rod. Thus, when the sleeve 274 is rotated in one direction, rod 282 moves in the distal direction while rod 280 withdraws proximally the same distance, and when sleeve 274 is rotated in the opposite direction, rod 280 moves in the distal direction and rod 282 moves proximally the same distance.

Collar 24 contains rotary ridges 24a in the distal half and longitudinal ridges 24b in the proximal half, and is thus conveniently movable longitudinally and rotatably by the user when the appropriate knurled portion is gripped between the user's fingers. However, the operator need not grip the collar 24 at any specific locations. The ridges may be formed integral by molding procedures or alternatively may be in the form of knurled surfaces. The rotary ridges respectively permit collar 24 to be finger movable distally and proximally, while the longitudinal ridges assist in rotation of collar 24 by hand. Rotational motion of the collar causes the endoscopic portion 14 to rotate while proximal movement of the collar in a preferred embodiment causes staple storing magazine 16 to pivot up to about 45 degrees in one direction with respect to the longitudinal axis of the instrument as shown in FIG. 1. Distal movement of the collar 24 to the distalmost position shown in FIG. 38, causes staple storing magazine 16 to withdraw to the original orientation shown in FIG. 1 which is generally in line with the endoscopic section. Thus, by pivoting the staple storing magazine up to 45 degrees and by rotating the endoscopic portion 14, the total range of movement of the staple storing magazine is 45 degrees to either side of the endoscopic section traversing a total of 90 degrees of effective pivotal movement. With respect to movements of collar 24, the direction which produces pivotal motion of staple storage magazine 16 away from the longitudinal axis or toward the axis is clearly a matter of choice and would be determined by the respective configurations of the coacting components.

In the alternative embodiment shown in FIG. 1A, the internal sleeve 274 and forward face 276 are configured such that collar 24 may be positioned midway between proximal and distal positions. The mid-position will correspond to the staple storage magazine being at zero degrees with respect to the longitudinal axis. Collar movement in one direction from neutral will produce up to 45 degrees of pivotal movement of magazine 16 and collar movement in the other direction on the side of neutral will produce pivotal movement of the magazine 16 up to 45 degrees in the other direction. A major distinction in this embodiment is that the actual orientation of the magazine with respect to the longitudinal axis will differ on either side of neutral.

Figure 45:
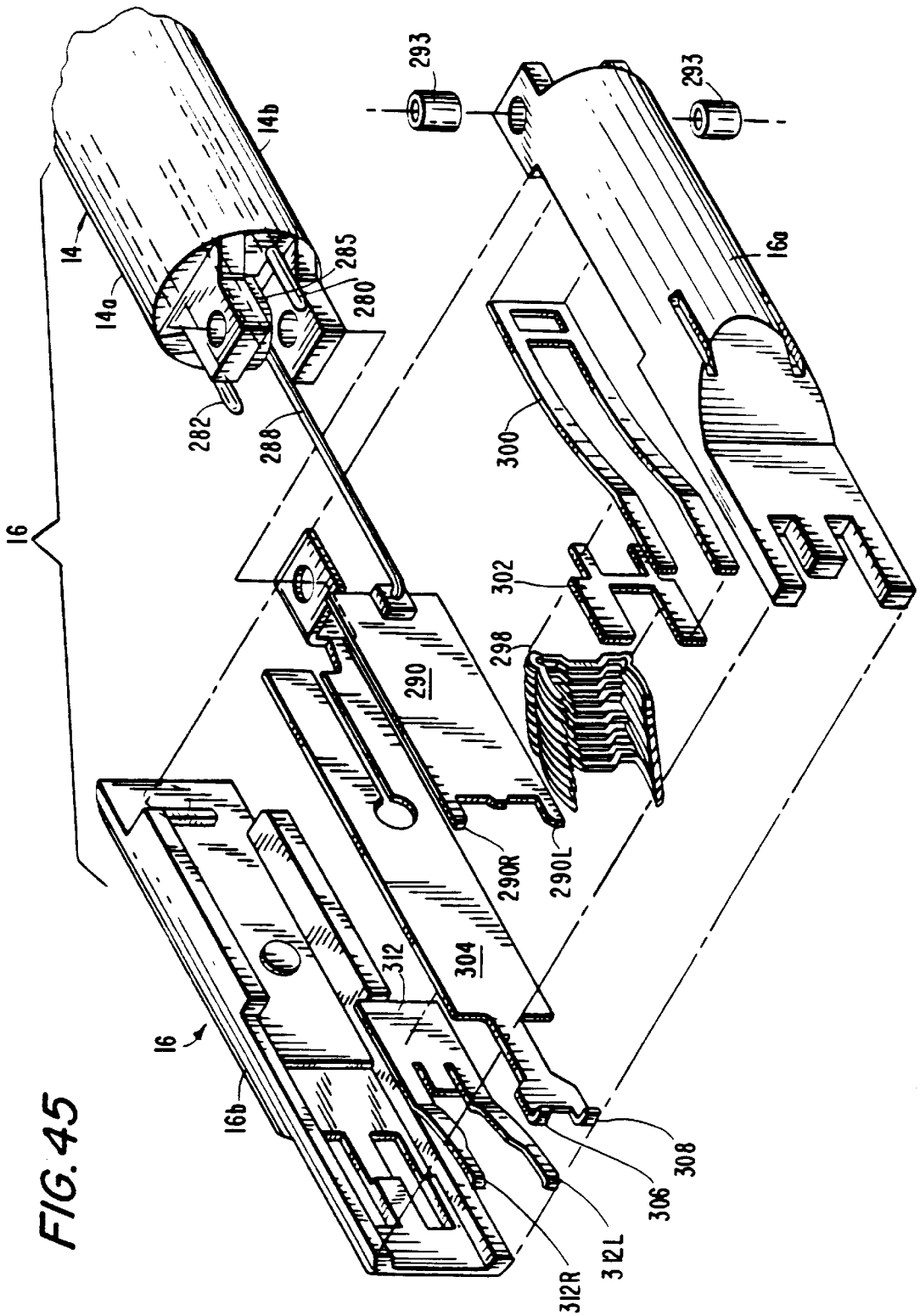
FIG. 45 is an exploded perspective view with parts separated, of the staple storage magazine which is controllably pivotally mounted at the distal end portion of the endoscopic section.

Referring now to FIGS. 45 and 46, the system for providing pivotal motion to the staple storing magazine 16 is illustrated at the distal end of the instrument. In FIG. 46 the staple storage magazine 16 is shown in the position generally in alignment with the endoscopic section and is shown in phantom lines at the pivoted locations corresponding to plus or minus 45 degrees. The staple storage magazine is formed of an outer housing of a suitable plastic material such as polycarbonate and is comprised of upper housing half section 16a and lower housing half section 16b attached by welding, adhesives, etc. The upper housing half section 16a contains an indentation 284 at the proximal end having a "V-shaped" cross section and the lower housing half section 16b contains a similar indentation 286 also having a "V-shaped" cross section as shown. Both indentations 284, 286 are adapted to respectively engagably receive the distal ends of rods 280,282 (which are rounded) such that when the rods are respectively and alternately moved in the proximal and distal directions as described hereinabove, one rod may advance distally to cause the upper housing to rotate and the other rod withdraws to permit the pivotal motion of the staple magazine. For example, as shown in FIG. 46, when rod 282 moves distally, engagement of the tip of the rod 282 with indentation 284 in upper housing 16a of staple storing magazine causes the staple magazine to pivot downwardly as shown in phantom.

Similarly, equal and oppositely withdrawing rod 280 will accommodate the downward movement of the staple storing magazine 16. In a similar fashion when the collar 24 is moved in the opposite distal direction the movement of each rod is respectively reversed causing rod 280 to move distally and to engage the lower housing 16b of staple storing magazine 16 and rod 282 withdraws to accommodate the pivotal movement of staple storing magazine back to the original (or neutral) position in general alignment with the endoscopic section as shown in FIG. 46.

Alternatively one rod may be provided and connected to the staple storage magazine and adapted to pivot the magazine by causing such rod to move proximally and distally thereby actually pivoting the magazine about the pivot point.

In the alternative, as disclosed in commonly-assigned U.S. patent application Ser. No. 07/950,425, filed Sep. 23, 1992, which is previously incorporated herein by reference, the staple storage magazine may be pivotally movable to positions 32.5° and 65° respectively relative to the longitudinal axis defined by the endoscopic section via a double knurled collar which is similar to collar 24 shown in FIGS. 38–43. Dual detent mechanisms are provided to positively establish the 0°, 32.5° or the 65° positions. Further, in accordance with this embodiment, the staple storage magazine is capable of rotating independent about its own central axis.

The Endoscopic Section and Staple Firing System

Figure 44:
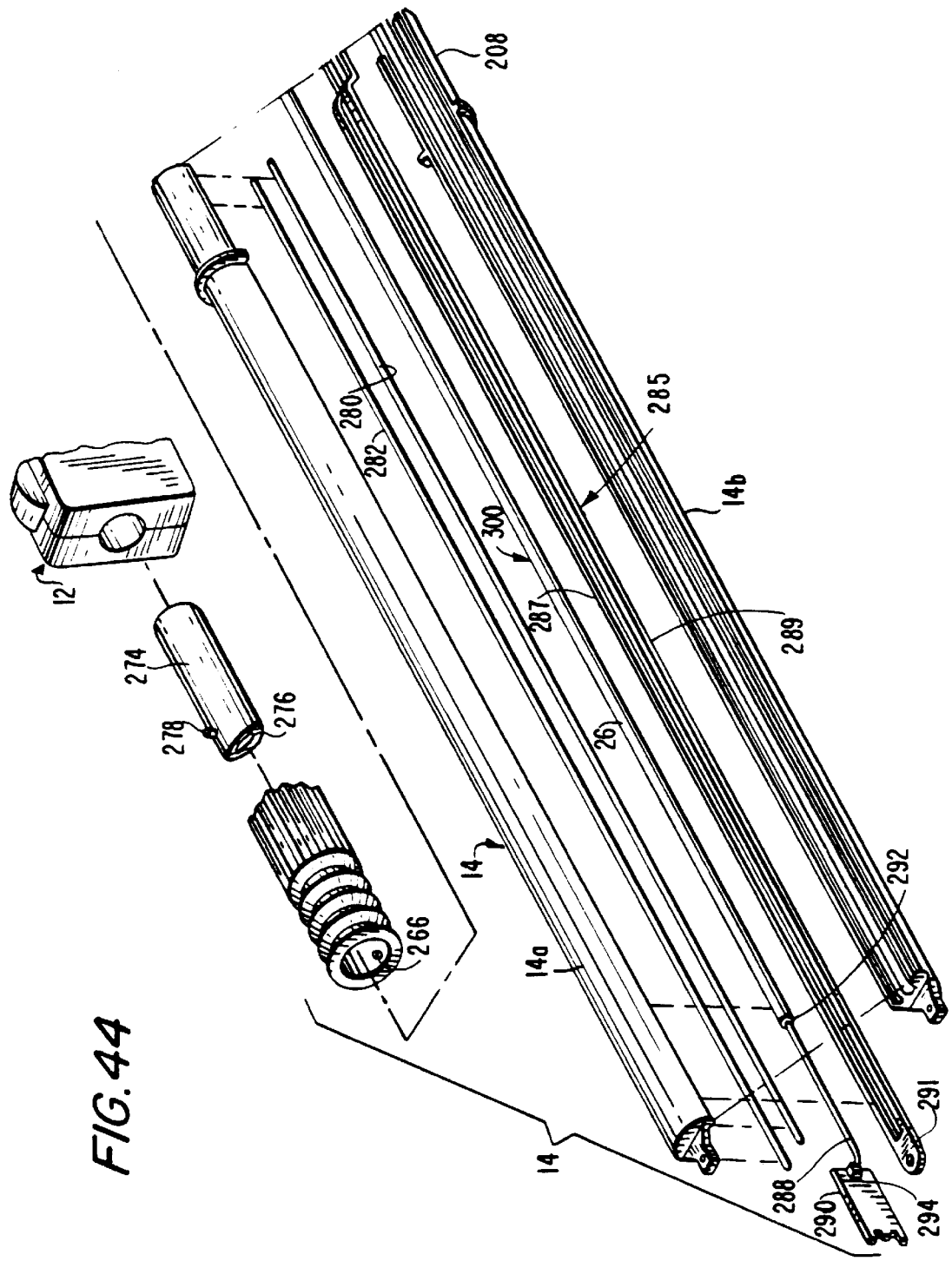
FIG. 44 is an exploded perspective view with parts separated, of the endoscopic section of the instrument of the invention, illustrating the staple advancing system and components thereof.

The endoscopic section 14 is shown clearly in FIG. 44 and is mounted for rotation relative to the handle section 12. As noted above, the endoscopic section may be permanently attached to the handle as shown in a disposable instrument; alternatively as noted above, it may be removably attached to a re-usable handle, or a variety of other combinations or configurations.

Referring again to FIG. 44 the endoscopic section is shown in exploded view with parts separated for convenience of illustration and includes upper housing half section 14a and lower housing half section 14b. The housing half sections are preferably of a polycarbonate material such as LEXAN brand material mentioned previously, and are attached by welding, adhesives, etc. Positioned within the upper and lower housing half sections is the pusher assembly 300 as described in more detail below and anvil extension 285, formed of stainless steel and having a pair of elongated legs 287, 289 which are joined at 291 at the distal end. As shown in FIG. 45, anvil extension 285 is attached at the distal end 291 to the staple storing magazine 16 by pivot pins 293 where the staple storing magazine is pivotally attached. The proximal end of anvil extension 285 is fixedly attached to handle 12 by conventional means.

Anvil extension 285 is fabricated of stainless steel and its purpose is to stabilize the dimension of the endoscopic section 14 to prevent the forces acting on the components from stretching or compressing the upper and lower housing half sections 14a,14b of the endoscopic section which are constructed of a polycarbonate material such as LEXAN brand material. Thus, the steel anvil extension provides dimensional stability to the endoscopic section while the endoscopic section is supporting the components being subjected to forces for supporting, advancing and forming the surgical staples as will be described.

Referring further to FIG. 44, the steel pusher assembly 300 is formed of firing rod 26 connected to flexible elongated firing wire 288 which is in turn connected to pusher plate assembly 290 as shown. The connection between firing rod 26 and firing wire 288 is a crimped or swaged connection at 292, whereas the connection between firing wire 288 and pusher 290 is accomplished by an interference fit between the firing wire 288 and collar 294 which is attached to pusher plate 290. Firing rod 26 and pusher plate 290 are preferably made of stainless steel whereas firing wire 288 is made to be resiliently flexible to accommodate the pivotal movement of the staple storing magazine 16 since firing wire 288 is located within the instrument at the location of staple magazine 16. In particular, firing wire 288 is preferably made of a super elastic metal. One example of such super elastic metal is TINEL brand metal available from Raychem Corporation, Menlo Park, Calif. This material has a reduced tendency to fatigue after a substantial number of cycles of deflection caused by pivoting the staple storage magazine. Other resilient materials are also contemplated for firing wire 288.

An alternative embodiment of the staple storage magazine, which is disclosed in commonly assigned U.S. patent application Ser. No. 07/861,065, filed Mar. 31, 1992, previously incorporated herein by reference, includes a cartridge which is self contained and which is readily insertable at the distal end portion of the endoscopic section. The staple storage cartridge is removably supported on a pivoted support system at the distal end portion of the endoscopic section.

The Staple Storage Magazine

Referring now to FIGS. 45–48 there is illustrated further details of the staple storing magazine 16. As noted previously, the staple storing magazine 16 is comprised of upper housing half 16a and lower housing half 16b suitably attached by welding, adhesives, etc. The magazine is adapted to contain a plurality of surgical staples 298 which are particularly shaped to penetrate and to attach surgical mesh to body tissue. For particular details of the shape of the staples constructed according to the invention, reference is made to FIG. 58.

Referring once again to FIGS. 45–48, a particular feature of the present invention resides in the system of storage of the staples 298 which are positioned in adjacent stacked relation whereby the stack of staples forms an angle with the longitudinal axis of the instrument of approximately 45 degrees as shown in FIG. 48. One purpose of stacking the staples as shown is to provide greater visibility to the user by the fact that the outer surface of the upper housing half section adjacent the stack of staples forms a similar angle and provides visibility to the user at the distal end of the staple storage magazine. Angular stacking of the staples as shown greatly facilitates storage of a plurality of staples in a structure configured and dimensioned for use in endoscopic applications, e.g., for use through a trocar guide tube of diameter of about 36 mm for example. The stack of staples 298 as shown in FIG. 48 is positioned and retained in such position by a resilient spring member 300 having dual resilient legs and whose side profile is curved as shown in FIG. 48.

The distal end of each leg engages the uppermost staple follower 302 in the form of a nylon insert having a general "H-shaped" configuration and dimensioned sufficient to cover the staples as best shown in FIG. 45. The nylon follower is intended to transmit the downward force of the staple retainer spring 300 so as to distribute the force on the stack of staples in a manner to facilitate a constant and uni-directional downward force on the lowermost staple which is positioned for advancement and deformation. It also functions to advance the stack of staples downwardly when the lowermost staple is fired. Steel anvil plate 304 is shown in FIG. 45 and includes upwardly extending feet and 306 and 308 which form anvils at the distal end as shown in FIG. 45, for forming the staple therearound.

Thus, as seen in FIG. 48, the lowermost staple is identified by numeral 298L and is in a position for engagement by pusher plate 290 when the pusher assembly is advanced distally. The pusher plate 290 is shown clearly in FIGS. 45 and 48 and contains distally advancing lands 290R and 290L shown clearly in FIGS. 45 and 49 at the distal end to facilitate transmission of advancing force to the two rounded or arcuate bridge portions of the staple. This relative complementary configuration of the pusher plate 290 and the staple 298 facilitates efficient and uniform distribution of force to the staple when it is deformed about the anvil members as will be described.

The Staple Closing System

Referring now to FIGS. 47–54 there is illustrated the sequential views of the staple advancing and closing system between the initial and fired condition of the staple. In particular, the staple and pusher mechanism are shown in FIG. 47 in the initial condition while the staple shown in FIG. 54 is embedded within the body tissue in a manner to retain the surgical mesh to the body tissue.

In FIG. 47, the staple pusher assembly is positioned proximal of the lowermost staple 298L and pusher plate 290 is correspondingly positioned proximal of the lowermost staple 298L. In FIGS. 48 and 49 the pusher plate 290 has been partially advanced distally by, e.g., the staple prepositioning stroke of the apparatus, and the lowermost staple 298L has been advanced distally of the stack of staples 298 in a manner such that the pusher plate 290 has now replaced lowermost staple 298L thereby preserving the integrity and position of the stack of staples 298. The preservation of the stack of staples 298 is provided by the fact that the thickness of the staple pusher plate 290 is either identical to or slightly less than the thickness of the staples to assume that the plate 290 will engage only one staple at a time.

Referring further to FIGS. 50 and 51, the pusher plate 290 has now advanced distally sufficient to cause the staple to penetrate the surgical mesh 305 and the body tissue 310. As shown in FIGS. 48 and 51, it can be seen that anvil members 306 and 308 are positioned for engagement by the straight sections of bridge portions 298BR and 298BL of the back rib of the staple 298L such that engagement of the staple by pusher plate 290 with the arcuate end corner portions of the staple as shown will cause the staple to deform in a predetermined manner as will be described.

In FIGS. 52–54 the staple 298L is now shown in the deformed condition about the anvil members 306 and 308 and the straight portions 298S of the back rib of the staple 298 are still in engagement with the anvils 306,308. In FIG. 52, the staple has penetrated into the body tissue 310 and has been deformed and in FIG. 54 the staple deformation is completed in a manner to substantially retain the surgical mesh 305 in attached position with respect to the body tissue as shown in FIG. 52. The inwardly projecting central portion or bight, 298C, of staple 298 is shown gripping the mesh and tissue in cooperation with the staple legs as shown in FIG. 54. However, release of the staples from the anvil members 306,308 has not yet been completed.

Release of the staple from the anvil members 306,308 is readily accomplished by ejector spring 312 which is a "U-shaped" resilient spring having upwardly biased legs 310R and 312L each positioned respectively as shown in FIG. 45. When the pusher plate 290 is in the position shown in FIG. 50, the legs 252R and 252L of staple ejector spring 312 are retained in a downward position by lands 290R and 290L of the pusher plate 290. However, when the pusher plate 290 is moved to the distalmost position shown in FIG. 53, the absence of the pusher plate permits staple ejector legs 312R and 312L to resiliently deflect upwardly to their natural configuration thereby creating a vertical separation between the anvil members 306,308 and the deformed staple, thus releasing the deformed staple from the anvil members as shown in FIG. 53. Continued proximal movement of the pusher plate 290 causes withdrawal of the pusher plate to a position entirely proximal of the stack of staples 298 as shown in FIG. 56, causing the stack of staples to move downwardly due to the downward force of resilient staple retainer spring 300 to advance the lowermost staple to the firing position.

Once the staple 298 is applied to the mesh 305 and tissue 310 as shown in FIGS. 52 and 54, the distal end of staple storing magazine 16 is withdrawn as shown in FIG. 54 and preparation is made for application of the next staple. FIG. 55 is a cross-sectional view taken along lines 55—55 of FIG. 54 with the staple storing magazine withdrawn from the surgical mesh 305 and body tissue. Thereafter, the apparatus may be repositioned to apply another staple, or even an array of staples as shown in FIGS. 57 and 59.

Referring once again to FIG. 57, there is illustrated one form of surgical mesh repair of an opening in the body utilizing the apparatus and staple. In the application shown in FIG. 57, a surgical mesh is attached to the body tissue over the opening as illustrated schematically at 310c in FIG. 57, and staples 298 have been applied in a circular array as shown to reinforce the repair. Beneath the mesh 305, the opening 310c may have previously been repaired as well. In FIG. 59 an alternative array of staples to apply mesh material to body tissue is shown. In this embodiment, the mesh material 305 is essentially formed as a circular patch and staples 298 are oriented in a radial direction and are attached around the periphery of the patch such that one leg of the staple pierces the mesh and the other leg pierces body tissue 310. Essentially the staple bridges the periphery of the mesh material as shown. Clearly, alternative forms and arrangements are available to attach mesh or other surgery related objects or prostheses to body tissue as may come to the mind of persons skilled in the art.

It should be further noted that the repair of body tissue utilizing surgical mesh as shown in FIGS. 56 and 58 are exemplary, and that other applications of mesh and staples may be utilized in a manner to either reinforce a surgical repair or to encourage tissue growth. Such mesh materials are typically disclosed in U.S. Pat. Nos. 4,838,884, 4,665,221, 4,452,245, and 4,347,847. It is noted that the staple as shown in FIG. 59 is particularly adapted for attachment of such mesh material to body tissue according to any number of techniques which may readily come to the mind of those skilled in the art. In fact, in some instances the mesh may be formed as a plug for insertion into a surgical opening and then stapled. Moreover, the apparatus and staple may be applied to attach other objects to body tissue as may come to the mind of those skilled in the art.

The Staple

Referring now once again to FIG. 59, there is illustrated staple 298. The staple 298 is particularly shaped as shown, and is preferably formed of a length of wire of titanium. Stainless steel or equivalent material is also contemplated and the staple preferably has a rectangular cross-section as shown. Other cross-sections may be used. Typically, the wire will be about 0.38 mm in width (dimension w) and 0.51 mm in thickness (dimension T). The initial width of the staple before closure (dimension A) is about 4.4 mm and the thickness dimension between the back rib and legs after closure (i.e. dimension B in FIG. 54) is about 3 mm. The staple 298 has a central bight portion 298C and a wire leg member 298R and 298L extending generally perpendicular to the central portion as shown. Each leg member 298R, 298L is connected to the central portion 298C by a bridge portion 298BR, 298BL having an arcuate corner portion as shown. Each leg member has a sharp tip for penetrating mesh and body tissue. Right leg member 298R further possesses a tapered surface 298TR at the tip which is opposite the position of the tapered surface 298TL at the tip of the other leg member 298L as shown in FIG. 58.

When the staple shown in FIG. 58 is advanced toward dual spaced anvils 306,308 as shown in FIG. 52 for example, and staple pusher plate 290 as shown, engages the arcuate portions of the bridge portions 298BR and 298BL, the legs of the staples are made to fold inwardly toward each other as shown for example in FIG. 52, with one leg crossing over the other. The cross-over configuration is automatically assumed by the legs because of the presence of tapered surfaces 298TR and 298TL which act as camming surfaces tending to bias each leg away from the other thereby tending to cross the legs in the manner shown. This structure also prevents interference of the legs when folded toward each other.

Thus, it can be seen that the particular shape of the staple as shown, promotes a unique folding pattern for the legs which achieves the configuration shown in the bent staples of FIGS. 52 and 54. Note in particular that inwardly bent central portion 298C promotes positive attachment of the mesh to the tissue by providing a gripping system between inwardly projecting bight portion 238C and leg members 298R and 298L with mesh and tissue gripped therebetween. This staple shape combines with the arrangement of the anvils and the particularly configured pusher plate 290 to cause the staple to pierce mesh and body tissue up to a predetermined extent. At this point, continued application of force to the staple causes the staple legs to fold upon themselves as shown in the drawings while encompassing a sufficient portion of the mesh to attach the mesh to the body tissue. Thus the staple pieces folds and grips in substantially a single movement.

In practice, the laparoscopic procedures to repair tissue in hernia repair using surgical mesh is similar in some respects to the surgical procedures to gall bladders, appendix, lungs, etc. In particular, the endoscopic tubular section of the apparatus is inserted into the cannula which is positioned within the opening in the body. Provision is made between the cannula and the endoscopic section to seal the connection therebetween and provision may also be provided to seal the actual endoscopic apparatus from leakage of fluids or insufflating gaseous media. An exemplary cannula assembly including seal means is disclosed for example in commonly assigned U.S. Pat. No. 4,943,224, issued Jul. 24, 1990, the disclosure of which is incorporated herein by reference.

The Kit

The present invention is readily adaptable to be provided to surgeons in the form of a kit in which all necessary equipment and accessories are provided in sterile form ready for use in surgery. For example, an apparatus constructed according to the invention can be readily packaged with a supply of staples (i.e. up to 36 or more staples) and sufficient mesh material for completing the hernial repair. The mesh material is typically about 1 mm in thickness. The components may be provided separately as a matched kit, or in a blister type or other package, suitable and ready for use by the surgeon and the surgeon's assistants. The apparatus and staples can be provided in any size matched to meet the apparatus and mesh material in accordance with the particular needs of a contemplated hernial surgical procedure. In addition, the kit can include a matching trocar assembly with appropriate valve assembly to prevent loss of the insufflating gas from the peritoneum between the trocar and the outside surface of the endoscopic section. Since the outer housing of the endoscopic section is substantially closed at the point of attachment of the staple magazine, release of insufflating gases through the staple magazine and the endoscopic section housing is either non existent or minimal. Such trocar assembly is available from United States Surgical Corporation, Norwalk, Conn., under the trademark SURGIPORT brand trocar assembly.

A typical endoscopic section may be a 36 mm diameter with a staple magazine capable of holding up to 10 staples of appropriate size. The length of the endoscopic section is typically 14 to 15 inches. An endoscopic section in the embodiment shown will be about 14 inches. However, if pivotal movement of the staple storage magazine is to be provided between plus 45 degrees and minus 45 degrees solely by distal and proximal movement of collar 24, the endoscopic section will be structured to greater in length, i.e. about 15 inches. The trocar assembly will be of matching size, i.e., 36 mm, to accommodate the endoscopic section and to prevent release of gases thereby. The mesh material provided with the kit will be of mesh size comparable for use with the size of the staples provided in the kit.

Thus by structuring the apparatus to provide such sealing, the endoscopic application of staples to attach objects such as surgical mesh to body tissue can be readily accomplished. Accordingly, the present invention is not only directed to the apparatus for applying such staples to body tissue, but also to a kit in which the apparatus is uniquely combined with a supply of staples, surgical mesh, cannula assembly etc. whereby the surgeon may readily perform the necessary procedures.

What is claimed is:

1. An endoscopic surgical stapling apparatus, which comprises:
   a) a handle adapted to be gripped by a hand of a user;
   b) an endoscopic portion connected to said handle and extending distally from said handle, said endoscopic portion including:
      i) means for storing at least one surgical staple;
      ii) a staple pusher for individually advancing said at least one surgical staple distally for positioning adjacent body tissue; and
      iii) an anvil for at least partially closing said one surgical staple;
   c) said handle including:
      i) a frame;
      ii) a pneumatic system disposed at least partially with said frame and including a supply of pressurized gas and adapted to convert said pressurized gas into a force to distally advance said staple pusher to at least partially close said one surgical staple about said anvil;
      iii) a manually engageable actuating member mounted to said frame and at least partially extending beyond said frame so as to be engaged by the user, said actuating member operatively connected to said pneumatic system, said actuating member movable a first distance from an initial position to a first position thereof to actuate said pneumatic system to distally advance said staple pusher;
      iv) an engaging member disposed within said frame and operatively connected to said actuating member, said engaging member positioned to operatively engage said staple pusher to prevent said staple pusher from advancing beyond a staple prepositioning position of said staple pusher, said staple prepositioning position corresponding to a partially advanced position of said staple pusher wherein said one staple is at least partially exposed from said storing means, said engaging member moveable to a release position in response to movement of said actuating member a second distance from said first position thereof to a second position thereof to operatively release said staple pusher to thereby permit said staple pusher to move distally under the influence of said pressurized gas beyond said staple prepositioning position to a fully advanced position wherein said one staple is at least partially closed about said anvil.

2. Apparatus according to claim 1 further comprising tactile means for providing a perceptible tactile indicator to the user when said staple pusher has been advanced to said staple prepositioning position, said tactile means including a spring member disposed within said frame, said spring member positioned to operatively engage said actuating member upon movement of said actuating member to said first position thereof wherein movement of said actuating member beyond said first position is resisted by said spring member.

3. Apparatus according to claim 1 wherein said staple pusher is biased to an initial proximal position by a constant force resilient member.

4. Apparatus according to claim 1 wherein said pneumatic system includes a piston adapted to advance in response to release of gas from said pneumatic system, said piston being operatively connected to said staple pusher such that distal movement of said piston causes corresponding distal movement of said staple pusher.

5. Apparatus according to claim 4 wherein said piston is connected to an actuating rod disposed within said frame, said actuating rod connected to said staple pusher such that longitudinal movement of said piston and said actuating rod causes corresponding longitudinal movement of said staple pusher.

6. Apparatus according to claim 5 wherein said engaging member is an actuating stop, said actuating stop movable between an engaged position wherein said actuating stop engages said actuating rod at a position corresponding to said staple prepositioning position of said staple pusher and a disengaged position wherein said actuating stop is disengaged from said actuating rod to permit further distal movement of said piston and said actuating rod thereby permitting movement of said staple pusher to said fully advanced position of said staple pusher.

7. Apparatus according to claim 1 wherein said staple storing means is pivotally attached at a distal end portion of said endoscopic portion.

8. Apparatus according to claim 7 including a control member for pivotally moving said staple storing means from a proximal location.

9. Apparatus according to claim 8 wherein said staple storing means is adapted to rotate to predetermined angles with respect to a longitudinal axis defined by said endoscopic portion.

10. Apparatus for endoscopic application of surgical staples to body tissue, which comprises:
    a) a handle member;
    b) a generally elongated endoscopic portion connected to the handle member and extending distally therefrom, the endoscopic portion including:
       i) a staple cartridge having at least one staple positioned therein;
       ii) an anvil; and
       iii) a staple pusher longitudinally distally movable and engagable with the one staple wherein distal movement of the staple pusher advances the one staple to at least partially close the one staple about the anvil; and
    c) the handle member including:
       i) a frame;
       ii) a pneumatic system including a supply of pressurized gas and adapted to convert the pressurized gas to distally advance the staple pusher;
       iii) a moveable member disposed within the frame and connected to the staple pusher, the moveable member distally moveable in response to release of the pressurized gas of the pneumatic system to distally advance the staple pusher;
       iv) an actuating member operatively connected to the pneumatic system and movably mounted to the frame, the actuating member at least partially extending beyond said frame so as to be engaged by a user, the actuating member movable a first distance from an initial position to a first position to activate the pneumatic system thereby causing distal advancing movement of the moveable member and the staple pusher;
       v) a stop disposed within the frame and positioned to engage the moveable member to prevent distal movement of the staple pusher beyond a staple prepositioning position thereof, the staple prepositioning position corresponding to a partially advanced position of the staple pusher wherein the one staple is at least partially exposed from the staple cartridge, the stop operatively connected to the actuating member and movable to a disengaged position disengaged from the moveable member in response to movement of the actuating member a second distance from the first position thereof to a second position thereof, to thereby permit the moveable member and the staple pusher to advance distally under the influence of the pressurized gas beyond the staple prepositioning position to a fully advanced position whereby the one staple is at least partially closed about the anvil.

11. Apparatus according to claim 10 including a release link connected to the actuating member and engageable with the stop, the release link moving the stop to the disengaged position upon movement of the actuating member the second distance from the first position thereof to the second position thereof.

12. Apparatus according to claim 11 including a spring member for providing a perceptible tactile indicator to the user when the staple pusher has been advanced to the staple prepositioning position, the spring member positioned to engage the release link upon movement of the actuating member and the release link to the first position of the actuating member such that movement of the actuating member beyond the first position is resisted by the spring member due to the engagement of the spring member with the release link.

13. Apparatus for endoscopic application of surgical staples to body tissue, which comprises:
   a) a handle member;
   b) a generally elongated endoscopic portion connected to the handle member and extending distally therefrom, the endoscopic portion including:
      i) a staple cartridge having at least one staple positioned therein;
      ii) an anvil; and
      iii) a staple pusher longitudinally distally moveable and engageable with the one staple wherein distal movement of the staple pusher advances the one staple to at least partially close the one staple about the anvil; and
   c) the handle member including:
      i) a pneumatic system including a supply of pressurized gas and adapted to convert the pressurized gas into a force to activate the staple pusher;
      ii) a manually engageable and manipulable actuating member operatively connected to the pneumatic system, the actuating member movable to activate the pneumatic system such that the staple pusher is distally advanced; and
      iii) an engaging member operatively connected to the staple pusher and movable between an engaged position and a disengaged position, wherein, in the engaged position, the engaging member operatively engages the staple pusher upon distal movement of the staple pusher to a first predetermined position thereof to thereby prevent distal movement of the staple pusher beyond the first predetermined position, and wherein, in the disengaged position, the engaging member operatively releases the staple pusher to permit further advancing movement of the staple pusher beyond the first predetermined position to a second fully advanced position to at least partially close the staple about the anvil.

* * * * *